United States Patent
Brines et al.

(10) Patent No.: US 8,404,226 B2
(45) Date of Patent: *Mar. 26, 2013

(54) TISSUE PROTECTIVE CYTOKINES FOR THE PROTECTION, RESTORATION, AND ENHANCEMENT OF RESPONSIVE CELLS, TISSUES AND ORGANS

(75) Inventors: Michael Brines, Woodbridge, CT (US); Anthony Cerami, Somers, NY (US); Carla Cerami, Sleepy Hollow, NY (US)

(73) Assignee: The Kenneth S. Warren Institute, Inc., Ossining, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/520,140

(22) PCT Filed: Jul. 3, 2003

(86) PCT No.: PCT/US03/21350
§ 371 (c)(1),
(2), (4) Date: Jan. 3, 2005

(87) PCT Pub. No.: WO2004/004656
PCT Pub. Date: Jan. 15, 2004

(65) Prior Publication Data
US 2006/0034799 A1 Feb. 16, 2006

Related U.S. Application Data

(63) Continuation-in-part of application No. 10/188,905, filed on Jul. 3, 2002, now abandoned.

(51) Int. Cl.
*A61K 45/00* (2006.01)
*A61K 38/18* (2006.01)
*A61K 38/16* (2006.01)

(52) U.S. Cl. .................. 424/85.1; 514/21.2; 514/7.7
(58) Field of Classification Search .................. None
See application file for complete search history.

(56) References Cited

U.S. PATENT DOCUMENTS

| | | | |
|---|---|---|---|
| 4,343,782 A | 8/1982 | Shapiro | |
| 4,377,513 A | 3/1983 | Sugimoto et al. | |
| 4,658,019 A | 4/1987 | Kung et al. | |
| 4,703,008 A | 10/1987 | Lin | |
| 4,806,524 A | 2/1989 | Kawaguchi et al. | |
| 4,835,260 A | 5/1989 | Shoemaker | |
| 4,992,419 A | 2/1991 | Woog et al. | |
| 5,194,596 A * | 3/1993 | Tischer et al. | 530/399 |
| 5,278,065 A | 1/1994 | D'Andrea | |
| 5,292,654 A | 3/1994 | Yoshimura | |
| 5,350,836 A * | 9/1994 | Kopchick et al. | 530/399 |
| 5,354,934 A | 10/1994 | Pitt et al. | |
| 5,457,089 A | 10/1995 | Fibi et al. | |
| 5,547,933 A | 8/1996 | Lin | |
| 5,571,787 A | 11/1996 | O'Brien et al. | |
| 5,591,713 A | 1/1997 | Igari et al. | |
| 5,604,198 A | 2/1997 | Poduslo et al. | |
| 5,614,184 A | 3/1997 | Sytkowski et al. | |
| 5,618,698 A | 4/1997 | Lin | |
| 5,621,080 A * | 4/1997 | Lin | 530/350 |
| 5,625,035 A | 4/1997 | Clemons | |
| 5,661,125 A | 8/1997 | Strickland | |
| 5,696,080 A | 12/1997 | O'Brien | |
| 5,700,909 A | 12/1997 | O'Brien | |
| 5,714,459 A | 2/1998 | O'Brien | |
| 5,750,376 A | 5/1998 | Weiss et al. | |
| 5,756,349 A | 5/1998 | Lin | |
| 5,763,198 A | 6/1998 | Hirth et al. | |
| 5,767,078 A | 6/1998 | Johnson et al. | |
| 5,773,569 A | 6/1998 | Wrighton et al. | |
| 5,824,672 A | 10/1998 | Simpkins et al. | |
| 5,830,851 A | 11/1998 | Wrighton et al. | |
| 5,835,382 A | 11/1998 | Wilson et al. | |
| 5,856,298 A | 1/1999 | Strickland | |
| 5,888,772 A | 3/1999 | Okasinski et al. | |
| 5,955,422 A | 9/1999 | Lin | |
| 5,997,865 A | 12/1999 | Bennett et al. | |
| 6,048,971 A | 4/2000 | Sytkowski et al. | |
| 6,071,970 A | 6/2000 | Mueller et al. | |
| 6,103,526 A | 8/2000 | Smith et al. | |
| 6,121,246 A | 9/2000 | Isner | |
| 6,153,407 A | 11/2000 | Sytkowski et al. | |
| 6,165,783 A | 12/2000 | Weiss et al. | |
| 6,200,567 B1 | 3/2001 | Lopez et al. | |
| 6,242,570 B1 | 6/2001 | Sytkowski | |
| 6,291,661 B1 | 9/2001 | Graddis et al. | |
| 6,340,742 B1 | 1/2002 | Burg et al. | |
| 6,399,336 B1 | 6/2002 | Paulson et al. | |
| 6,440,932 B1 | 8/2002 | Lehmann et al. | |

(Continued)

FOREIGN PATENT DOCUMENTS

| CA | 2294448 | 12/1998 |
|---|---|---|
| CA | 2353553 | 6/2000 |

(Continued)

OTHER PUBLICATIONS

Brines et al., PNAS USA, Sep. 12, 2000; 97(19):10526-10531.*
Kitajima et al., Rinsho Ketsueki. Jul. 1994 35(7):694-8, Abstract Only.*
Satake et al., Biochimica et Biophysica Acta. 1990;1038:125-129.*
Benjamin et al., 1998, Development 125:1591-1598.*
Vukicevic et al. 1996, PNAS USA 93:9021-9026.*
Massague. 1987, Cell 49:437-8.*
Pilbeam et al., 1993, Bone 14:717-720.*
Steadman's Medical Dictionary, 27th Ed. 2000, Lippincott, Williams, and Wilkins: Trauma and Inflammation.*

(Continued)

*Primary Examiner* — Cherie M Stanfield
(74) *Attorney, Agent, or Firm* — Jones Day

(57) ABSTRACT

Methods and compositions are provided for treating a mammal having inflammation by protecting or enhancing a responsive cell, tissue, organ or body part exhibiting or associated with the inflammation, by systemic or local administration of a composition comprising a tissue protective cytokine. The invention also encompasses combination treatments comprising administering a composition comprising a tissue protective cytokine of the invention and administering at least one anti-inflammatory or least one immunomodulatory agent.

31 Claims, 29 Drawing Sheets

U.S. PATENT DOCUMENTS

| | | |
|---|---|---|
| 6,475,717 B1 | 11/2002 | Enssle et al. |
| 6,489,293 B1 | 12/2002 | Sytkowski et al. |
| 6,521,245 B1 | 2/2003 | Zaharia |
| 6,531,121 B2 * | 3/2003 | Brines et al. .......... 424/85.1 |
| 6,583,272 B1 | 6/2003 | Bailon |
| 6,645,522 B2 | 11/2003 | Naeff et al. |
| 6,673,575 B1 * | 1/2004 | Franze et al. .......... 435/71.1 |
| 6,747,002 B2 | 6/2004 | Cheung et al. |
| 6,784,154 B2 | 8/2004 | Westenfelder |
| 6,855,544 B1 | 2/2005 | Hateboer et al. |
| 6,930,086 B2 | 8/2005 | Tischer |
| 7,053,184 B2 | 5/2006 | Lee |
| 7,087,224 B2 | 8/2006 | Kay et al. |
| 7,091,326 B2 | 8/2006 | Lee et al. |
| 7,098,318 B2 | 8/2006 | Lee et al. |
| 7,214,532 B2 | 5/2007 | Stern et al. |
| 7,220,555 B2 | 5/2007 | Paulson et al. |
| 7,262,166 B2 | 8/2007 | Kinstler et al. |
| 7,297,680 B2 | 11/2007 | Opstelten et al. |
| 7,300,915 B2 | 11/2007 | Campana et al. |
| 7,300,916 B2 | 11/2007 | Yasuda et al. |
| 7,304,031 B2 | 12/2007 | Opstelten et al. |
| 7,309,687 B1 | 12/2007 | Brines et al. |
| 7,345,019 B1 | 3/2008 | Brines et al. |
| 7,410,941 B1 | 8/2008 | Brines et al. |
| 7,504,248 B2 | 3/2009 | Marzio et al. |
| 7,645,733 B2 | 1/2010 | Brines et al. |
| 7,718,363 B2 | 5/2010 | Brines et al. |
| 7,767,643 B2 | 8/2010 | Brines et al. |
| 2002/0052309 A1 | 5/2002 | Anagnostou et al. |
| 2002/0061849 A1 | 5/2002 | Nielsen et al. |
| 2002/0081734 A1 | 6/2002 | Choi et al. |
| 2002/0160460 A1 | 10/2002 | Paulson et al. |
| 2003/0003529 A1 | 1/2003 | Bayer |
| 2003/0040037 A1 | 2/2003 | Bayer |
| 2003/0072737 A1 | 4/2003 | Brines et al. |
| 2003/0089468 A1 | 5/2003 | Kettunen et al. |
| 2003/0104988 A1 | 6/2003 | Brines et al. |
| 2003/0118547 A1 * | 6/2003 | Vandenberg .......... 424/85.4 |
| 2003/0120045 A1 | 6/2003 | Bailon |
| 2003/0134798 A1 | 7/2003 | Brines et al. |
| 2004/0009902 A1 | 1/2004 | Boime |
| 2004/0091961 A1 | 5/2004 | Evans et al. |
| 2004/0122216 A1 | 6/2004 | Nielsen et al. |
| 2004/0209812 A1 | 10/2004 | Farrell et al. |
| 2004/0214236 A1 | 10/2004 | Brines et al. |
| 2005/0106722 A1 | 5/2005 | Jones et al. |
| 2005/0164386 A1 | 7/2005 | Uytdehaag et al. |
| 2005/0170463 A1 | 8/2005 | Bout et al. |
| 2005/0176627 A1 | 8/2005 | Cerami et al. |
| 2006/0099685 A1 | 5/2006 | Yallop et al. |
| 2006/0135754 A1 | 6/2006 | Christensen et al. |
| 2006/0216757 A1 | 9/2006 | Brines et al. |
| 2007/0054394 A1 | 3/2007 | Bout et al. |
| 2007/0117742 A1 | 5/2007 | Opstelten et al. |
| 2007/0129293 A1 | 6/2007 | Coleman et al. |
| 2007/0231860 A1 | 10/2007 | Uytdehaag et al. |
| 2007/0275439 A1 | 11/2007 | Opstelten |
| 2007/0298031 A1 | 12/2007 | Brines et al. |
| 2007/0298464 A1 | 12/2007 | Optelten et al. |
| 2008/0014193 A1 | 1/2008 | Brines et al. |
| 2008/0032922 A1 | 2/2008 | Opstelten et al. |
| 2008/0050403 A1 | 2/2008 | Marzio et al. |
| 2008/0305990 A1 | 12/2008 | Brines et al. |
| 2009/0004202 A1 | 1/2009 | Brines et al. |
| 2009/0136519 A1 | 5/2009 | Brines et al. |
| 2009/0233844 A1 | 9/2009 | Brines et al. |
| 2009/0258821 A1 | 10/2009 | Cerami et al. |
| 2012/0142589 A1 | 6/2012 | Brines et al. |

FOREIGN PATENT DOCUMENTS

| | | |
|---|---|---|
| DE | 198 57 609 | 6/2000 |
| EP | 555880 | 8/1993 |
| EP | 0640619 | 1/1995 |
| EP | 0668351 | 8/1995 |
| EP | 0883343 | 4/1997 |
| EP | 1064951 | 1/2001 |
| EP | 1440157 | 5/2003 |
| EP | 1625858 | 2/2006 |
| EP | 1633383 | 3/2006 |
| EP | 1831381 | 7/2006 |
| EP | 1889627 | 2/2008 |
| FR | 2 823 220 | 10/2002 |
| JP | 05092928 | 4/1993 |
| JP | 5-246885 | 9/1993 |
| JP | 2002-532432 | 10/2002 |
| WO | WO 85/02610 | 6/1985 |
| WO | WO 86/03520 | 6/1986 |
| WO | WO 90/11354 | 10/1990 |
| WO | WO 91/05867 | 5/1991 |
| WO | WO 91/06667 | 5/1991 |
| WO | WO 91/09955 | 7/1991 |
| WO | WO 92/08493 | 5/1992 |
| WO | WO 93/09222 | 5/1993 |
| WO | WO 93/25221 | 12/1993 |
| WO | WO 94/12650 | 6/1994 |
| WO | WO 94/24160 | 10/1994 |
| WO | WO 94/28024 | 12/1994 |
| WO | WO 95/05465 | 2/1995 |
| WO | WO 95/31560 | 11/1995 |
| WO | WO 96/14081 | 5/1996 |
| WO | WO 97/08307 | 3/1997 |
| WO | WO 97/14307 | 4/1997 |
| WO | WO 97/18318 | 5/1997 |
| WO | WO 97/32895 | 12/1997 |
| WO | WO 98/10650 | 3/1998 |
| WO | WO 98/18926 | 5/1998 |
| WO | WO 98/19685 | 5/1998 |
| WO | WO 98/19695 | 5/1998 |
| WO | WO 98/58660 | 12/1998 |
| WO | WO 99/21966 | 5/1999 |
| WO | WO 00/24893 | 5/2000 |
| WO | WO 00/32772 | 6/2000 |
| WO | WO 00/35475 | 6/2000 |
| WO | WO 00/61164 | 10/2000 |
| WO | WO 01/02017 | 1/2001 |
| WO | WO 01/81405 | 11/2001 |
| WO | WO 01/82952 | 11/2001 |
| WO | WO 01/82953 | 11/2001 |
| WO | WO 01/87329 | 11/2001 |
| WO | WO 02/00721 | 1/2002 |
| WO | WO 02/10743 | 2/2002 |
| WO | WO 02/14356 | 2/2002 |
| WO | WO 02/49673 | 6/2002 |
| WO | WO 02/053580 | 7/2002 |
| WO | WO 02/085940 A2 * | 10/2002 |
| WO | WO 03/029291 | 4/2003 |
| WO | WO 03/038100 | 5/2003 |
| WO | WO 03/089468 | 10/2003 |
| WO | WO 2004/003176 | 1/2004 |
| WO | WO 2004/004656 | 1/2004 |
| WO | WO 2004/022577 | 3/2004 |
| WO | WO 2004/087063 | 10/2004 |
| WO | WO 2004/096148 | 11/2004 |
| WO | WO 2004/112693 | 12/2004 |
| WO | WO 2005/025606 | 3/2005 |
| WO | WO 2005/032467 | 4/2005 |
| WO | WO 2005/084364 | 9/2005 |
| WO | WO 2005/117927 | 12/2005 |
| WO | WO 2006/002646 | 1/2006 |
| WO | WO 2006/014349 | 2/2006 |
| WO | WO 2006/014466 | 2/2006 |
| WO | WO 2006/070011 | 7/2006 |
| WO | WO 2006/129755 | 12/2006 |

OTHER PUBLICATIONS

FDA Alert (Nov. 16, 2006, updated Feb. 16, 2006 and Mar. 9, 2007).*
Fukada et al. Blood. Jan. 1989;73(1):84-9, Abstract Only.*
Gunaseker et al., Toxicological Sciences. 2001; 64:83-89.*
Gorio et al., PNAS USA. Nov. 8, 2005;102(45):16379-84. Epub Oct. 31, 2005.*
Schiffl et al., Eur J Med Res. Mar. 24, 1997;2(3):97-100, Abstract only.*
Anagnostou et al., 1994, "Erythropoietin receptor mRNA expression in human endothelial cells", Proc. Natl. Acad. Sci. USA 91:3974-3978.

Annable et al., 1972, "The Second International Reference Preparation of Erythropoietin, Human, Urinary, for Bioassay," Bull. Org. mond. Sante, 47:99-112.

Ashwell et al., 1978, "A Protein from Mammalian Liver that Specifically Binds Galactose-Terminated Glycoproteins," Meth. Enzymol., 50:287-291.

Bauer, 1995, "The Oxygen Sensor That Controls EPO Production: Facts and Fancies," J. Perinat. Med., 23:7-12.

Bernaudin et al., 1999, "A potential role for erythropoietin in focal permanent cerebral ischemia in mice", J. Cereb. Blood Flow Metab. 19:643-651.

Bondy, 1995, "The relaxation of oxidative stress and hyperexcitation to neurological disease", Proc. Soc. Exp. Biol. Med. 208:337-345.

Briggs et al., 1974, "Hepatic Clearance of Intact and Desialylated Erythropoietin," Am. J. Physiol., 227:1385-1388.

Brines et al., 2000, "Erythropoietin crosses the blood-brain barrier to protect against experimental brain injury", Proc. Natl. Acad. Sci. USA 97:10526-10531.

Bruneval et al., 1993, "Erythropoietin Synthesis by Tumor Cells in a Case of Meningioma Associated With Erythrocytosis," Blood, 81:1593-1597.

Campana et al., 1998, "Identification of a neurotrophic sequence in erythropoietin", Int. J. Mol. Med. 1:235-241.

Cotes, 1968, "Quantitative Estimation of Erythropoietin," Part I. Assay and Standardization of Erythropoietin, Annals New York Acad. Sci., 149:12-17.

Diaz-Brinton et al., 1998, "Advances and challenges in the prevention and treatment of Alzheimer's disease," Pharm. Res. 15(3):386-98.

Digicaylioglu et al. 1995, "Localization of specific erythropoietin binding sites in defined areas of the mouse brain.", Proc. Natl. Acad. Sci. USA 92:3717-3720.

Dipaolo et al., 1992, "Effects of uremia and dialysis on brain electrophysiology after recombinant erythropoietin treatment", ASAIO J. 38:M477-M480.

Dong et al., 1992, "Receptor binding of asialoerythropoietin," J. Cell. Biochem. 48(3):269-76.

Dordal et al., 1985, "The Role of Carbohydrate in Erythropoietin Action," Endocrinol., 116:2293-2299.

Dube et al, 1988, "Glycosylation at Specific Sites of Erythropoietin is Essential for Biosynthesis, Secretion, and Biological Function," J. Biol. Chem., 263:17516-17521.

Ehrenreich et al., 2002, "Erythropoietin therapy for acute stroke is both safe and beneficial", Molec. Med. 8(8):495-505.

Eur. Pharmacopoeia, 1997, p. 5.

Eur. Pharmacopoeia, Suppl. 2001, pp. 777-782.

Feigin et al., 2002, "Recent advances in Huntington's disease: implications for experimental therapeutics," Curr. Opin. Neurol. 15(4):483-9.

Fukuda et al., 1989, "Survival of Recombinant Erythropoietin in the Circulation: The Role of Carbohydrates," Blood, 73:84-89.

Goldwasser et al., 1974, "On the Mechanism of Erythropoietin-Induced Differentiation," XIII. The Role of Sialic Acid in Erythropoietin Action, J. Biol. Chem., 249:4202-4206.

Goldwasser et al., 1975, "An Assay for Erythropoietin in Vitro at the Milliunit Level," Endo., 97:315-323.

Goldwasser et al., "Erythropoietin: Assay and Study of Its Mode of Action," Hormone Assays, pp. 109-121.

Gorio et al., 2002, "Recombinant human erythropoietin counteracts secondary injury and markedly enhances neurological recovery from experimental spinal cord trauma", Proc. Natl. Acad. Sci. USA 99:9450-9455 (PNAS Early Edition www.pnas.org/cgi/doi/10.1073/pnas.142287899).

Grasso et al., 2002, "Beneficial effects of systemic administration of recombinant human erythrpoietin in rabbits subjected to subarachnoid hemorrhage", Proc. Natl. Acad. Sci. USA 99:5627-5631.

Gregory et al., 1999, "GATA-1 and erythropoietin cooperate to promote erythroid cell survival by regulating bcl-xL expression", Blood 94:87-96.

Grimm et al., 1990, "Improvement of brain function in hemodialysis patients treated with erythropoietin", Kidney Intl. 38:480-486.

Hammond et al., 1968, "Production, Utilization and Excretion of Erythropoietin: I. Chronic Anemias. II. Aplastic Crisis. III. Erythropoietic Effects of Normal Plasma," Erythropoietin, 149:516-527.

Hefti, 1997, "Pharmacology of neurotrophic factors", Annu. Rev. Pharmacol. Toxicol. 37:239-267.

Hengemihle et al., 1996, "Chronic treatment with human recombinant erythropoietin increases hematocrit and improves water maze performance in mice", Physiol. Behav. 59:153-156.

Hirakata et al., 1992, "CBF and oxygen metabolism in hemodialysis patients: effects of anemia correction with recombinant human EPO", Am. J. Physiol. 262:F737-F743.

Jooss et al., 1996, "Cyclophosphamide diminishes inflammation and prolongs transgene expression following delivery of adenoviral vectors to mouse liver and lung," Hum. Gene Ther. 7(13):1555-66.

Junk et al., 2002, "Erythropoietin administration protects retinal neurons from acute ischemia-reperfusion injury", Proc. Natl. Acad. Sci. USA 99:10659-10664 (PNAS Early Edition www.pnas.org/cgi/doi/10.1073/pnas.152321399).

Juul et al., 1998, "Erythropoietin and erythropoietin receptor in the developing human central nervous system", Pediatr. Res. 43:40-49.

Juul et al., 1998, "Tissue distribution of erythropoietin and erythropoietin receptor in the developing human fetus", Early Human Devel. 52:235-249.

Juul et al., 2001, "Recombinant erythropoietin (EPO) crosses the blood brain barrier (BBB) in preterm fetal sheep", Soc. for Neuroscience Abstracts 27:929 (31st Annual Meeting of the Society for Neuroscience, San Diego, CA Nov. 10-15, 2001).

Keighley, 1968, "Further Experiences with Assays, Units, and Standards of Erythropoietin," Annals New York Acad. Sci., 149:18-24.

Kohama et al., 2000, "Large Uterine Myoma with Erythropoietin Messenger RNA and Erythrocytosis," Obstetrics and Gynecology, 96:826-828.

Konishi et al., 1993, "Trophic effect of erythropoietin and other hematopoietic factors on central cholinergic neurons in vitro and in vivo", Brain Res. 609:29-35.

Kopf et al., 1994, "Memory improving actions of glucose: involvement of a central cholinergic muscarinic mechanism.", Behav. Neural Biol. 62:237-243.

Latini et al., 1998, "Comparative efficacy of a DA2/α2 agonist and a β blocker in reducing adrenergic drive and cardiac fibrosis in an experimental model of left ventricular dysfunction after coronary artery occlusion", J. Cardiovasc. Pharmacol. 31:601-608.

Li et al., 1996, "Erythropoietin receptors are expressed in the central nervous system of mid-trimester human fetuses", Pediatr. Res. 40:376-380.

Li et al., 1998, "A single pre training glucose injection induces memory facilitation in rodents performing various tasks: contribution of acidic fibroblast growth factor", Neurosci. 85:785-794.

Lipinski et al., 1995, "Nerve growth factor facilitates conditioned taste aversion learning in normal rats", Brain Res. 692:143-153.

Liu et al., 1996, "Transgenic mice containing the human erythropoietin receptor gene exhibit correct hematopoietic and neural expression", Proc. Assoc. Am. Physicians 108:449-454.

Liu et al., 1997, "Regulated human erythropoietin receptor expression in mouse brain", J. Biol. Chem. 272:32395-32400.

Liu et al., 1994, "Tissue specific expression of human erythropoietin receptor in transgenic mice", Devel. Biol. 166:159-169.

Marrero et al., 1998, "Erythropoietin receptor-operated Ca2+ channels: activation by phospholipase C-γ1", Kidney Intl. 53:1259-1268.

Marsh et al., 1991, "rHuEPO treatment improves brain and cognitive function of anemic dialysis patients", Kidney Intl. 39:155-163.

Marti et al., 1997, "Detection of erythropoietin in human liquor: intrinsic erythropoietin production in the brain", Kidney Intl. 51:416-418.

Marti et al., 1996, "Erythropoietin gene expression in human, monkey and murine brain", Eur. J. Neurosci. 8:666-676.

Masuda et al., 1997, "Insulin like growth factors and insulin stimulate erythropoietin production in primary cultured astrocytes", Brain Res. 746:63-70.

Masuda et al., 1994, "A novel site of erythropoietin production. Oxygen dependent production in cultured rat astrocytes", J. Biol. Chem. 269:19488-19493.

Masuda et al., 1993, "Functional erythropoietin receptor of the cells with neural characteristics. Comparison with receptor properties of erythroid cells", J. Biol. Chem. 268:11208-11216.

Miyake et al., 1977, "Purification of Human Erythropoietin," J. Biol. Chem., 252:5558-5564.

Morell et al., 1968, "Physical and Chemical Studies on Ceruloplasmin," Metabolic Studies on Sialic Acid-Free Ceruloplasmin In Vivo, J. Biol. Chem., 243:155-159.

Morishita et al., 1997, "Erythropoietin receptor is expressed in rat hippocampal and cerebral cortical neurons, and erythropoietin prevents in vitro glutamate induced neuronal death", Neurosci. 76:105-116.

Moss et al., 1996, "Oxygen administration enhances memory formation in healthy young adults", Psychopharmacol. 124:255-260.

Nakamura et al., 1998, "Elevated levels of erythropoietin in cerebrospinal fluid of depressed patients", Am. J. Med. Sci. 315:199-201.

Nissenson et al., 1991, "Recombinant human erythropoietin and renal anemia: molecular biology, clinical efficacy and nervous system effects", Ann. Int. Med. 114:402-416.

Nissenson, 1989, "Recombinant human erythropoietin: impact on brain and cognitive function, exercise tolerance, sexual potency and quality of life", Sem. Nephrol. 9(suppl. 2):25-31.

Ogden, 1989, "Monitoring considerations in recombinant human erythropoietin therapy", Sem. Nephrol. 9(suppl. 2):12-15.

Pardridge, 1997, "Drug delivery to the brain", J. Cerebral Blood Flow Metab. 17:713-731.

Pardridge et al., 1991, "Selective transport of an anti-transferrin receptor antibody through the blood-brain barrier in vivo", J. Pharmacol. Exp. Ther. 27:66-70.

Poduslo et al., 1994, "Macromolecular premeability across the blood-nerve and blood-brain barriers", Proc. Natl. Acad. Sci. USA 91:5705-5709.

Prendergast et al., 1997, "Nitric oxide synthase inhibition impairs spatial navigation learning and induces conditioned taste aversion", Pharmacol. Biochem. Behav. 57:347-352.

Rose et al., 1998, "Receptor-mediated angiotensin II transcytosis by brain microvessel endothelial cells", Peptides 19:1023-1030.

Sadamato et al., 1998, "Erythropoietin prevents place navigation disability and cortical infarction in rats with permanent occlusion of the middle cerebral artery", Biochem. Biophys. Res. Comm. 253:26-32.

Sakanaka et al., 1998, "In vivo evidence that erythropoietin protects neurons from ischemic damage", Proc. Natl. Acad. Sci. USA 95:4635-4640.

Satake et al. 1990, "Chemical modification of erythropoietin: an increase in in vitro activity by guanidination," Biochim. Biophys. Acta. 1038(1):125-9.

Sawyer et al., 1989, "Receptors for erythropoietin in mouse and human erythroid cells and placenta", Blood 74:103-109.

Shiramizu et al., 1994, "Constitutive Secretion of Erythropoietin by Human Renal Adenocarcinoma Cells in Vivo and in Vitro," Exp. Cell Res., 215:249-256.

Shore et al., 1968, "Quantitative Estimation of Erythropoietin," Annals New York Acad. Sci., 149:46-48.

Silva et al., 1999, "Erythropoietin can induce the expression of bcl-xL through Stat5 in erythropoietin-dependent progenitor cell lines", J. Biol. Chem. 274:22165-22169.

Sirén et al., 2001, "Erythropoietin prevents neuronal apoptosis after cerebral ischemia and metabolic stress", Proc. Natl. Acad. Sci. USA 98:4044-4049.

Spivak et al., 1989, "The In Vivo Metabolism of Recombinant Human Erythropoietin in the Rat," Blood, 73:90-99.

Stark et al., 1960, "Reactions of the Cyanate Present in Aqueous Urea With Amino Acids and Proteins," J. Biol. Chem. 235(11): 3177-3181.

Steece-Collier et al., 2002, "Etiology of Parkinson's disease: Genetics and environment revisited," Proc. Natl. Acad. Sci. U. S. A. 99(22):13972-4.

Storring et al., 1998, "Epoietin Alfa and Beta Differ in Erythropoietin Isoform Compositions and Biological Properties," British J. Haematology, 100:79-89.

Storring et al., 1992, "The International Standard for Recombinant DNA-Derived Erythropoietin: Collaborative Study of Four Recombinant DNA-derived Erythropoietins and Two Highly Purified Human Urinary Erythropoietins," J. Endocrinol., 134:459-484.

Suzuki et al., 2001, "Erythropoietin Synthesis by Tumour Tissues in a Patient With Uterine Myoma and ERythrocytosis," British J. Haematology, 113:49-51.

Tabira et al., 1995, "Neurotrophic effect of hematopoietic cytokines on cholinergic and other neurons in vitro", Int. J. Devl. Neurosci. 13:241-252.

Weiland et al., "In vivo Activity of Asialo-Erythropoietin in Combination with Asialo-Glycoproteins," 1982, Blut, 44:173-175.

Westenfelder et al., 1999, "Human, rat and mouse kidney cells express functional erythropoietin receptors", Kidney Intl. 55:808-820.

Williams et al., 1994, "Human erythropoietin receptor", Ann. NY Acad. Sci. 718:232-244.

Wolcott et al., 1989, "Recombinant human erythropoietin treatment may improve quality of life and cognitive function in chronic hemodialysis patients", Am. J. Kidney Dis. 14:478-485.

Wu et al., 1999, "Neuroprotection with noninvasive neurotrophin delivery to the brain", PNAS 96:254-259.

Yamaji et al., 1996, "Brain capillary endothelial cells express two forms of erythropoietin receptor mRNA", Eur. J. Biochem. 239:494-500.

Yang et al., 2002, "Effects of ammonia and glucosamine on the heterogeneity of erythropoietin glycoforms," Biotechnol. Prog. 18(1):129-38.

Final Office Action mailed May 23, 2008 for U.S. Appl. No. 10/185,841, filed Jun. 26, 2002.

Final Office Action mailed Jan. 8, 2008 for U.S. Appl. No. 10/188,905, filed Jul. 3, 2002.

Final Office Action mailed Mar. 19, 2008 for U.S. Appl. No. 10/351,640, filed Jan. 24, 2003.

Title page, table of contents and Chapter 7 of Chemical Reagents for Protein Modification, authored by R. L. Lundblad (CRC Press: Boca Raton, Florida, 1991.

Fantacci et al., Proc. Natl. Acad. Sci. USA, 2006, 103(46): 17531-17536.

Diem et al., 2005, Brain 128:375-385.

Savino et al., 2006, Journal of Neuroimmunology 172:27-37.

Cuzzocrea et al., 2005, Arthritis & Rheumatism 52:940-950.

Szabo et al., 1998, PNAS 95(7):3867-72.

U.S. Appl. No. 60/458,193, filed Mar. 28, 2003, Renzi.

U.S. Appl. No. 09/290,938, filed Apr. 13, 1999, Brines et al.

U.S. Appl. No. 09/547,220, filed Apr. 11, 2000, Brines et al.

U.S. Appl. No. 09/716,963, filed Nov. 21, 2000, Brines et al.

U.S. Appl. No. 09/718,829, filed Nov. 21, 2000, Brines et al.

U.S. Appl. No. 11/880,275, filed Jul. 19, 2007, Brines et al.

Patent Interference No. 105,500 Ehrenreich v. Brines: Judgment Paper 1, Declaration, Brines clean copy of claims, and Ehrenreich clean copy of claims (Oct. 2, 2006).

Abdelrahman, 2004, "Erythropoietin attenuates the tissue injury associated with hemorrhagic shock an myocardial ischemia," Shock, vol. 22(1), pp. 63-69.

Agnello et al., 2002, "Erythropoietin exerts an anti-inflammatory effect on the CNS in a model of experimental autoimmune encephalomyelitis," Brain Research 952:128-134.

Akhtar et al., 1999, "Conformational study of N(epsilon)-(carboxymethyl)lysine adducts of recombinant alpha-crystallins," Current Eye Research 18:270-276.

Alafaci et al., 2000, "Effect of Recombinant Human Erythropoietin on Cerebral Ischemia Following Experimental Subarachnoid Hemorrhage," Eur. J. Phar., 406:219-225.

Anagnostou et al., 1994, "Erythropoietin receptor mRNA expression in human endothelial cells", Proc. Natl. Acad. Sci, USA 91:3974-3978.

Ando et al,. 1996, "Autonomic dysfunction and anemia in neurologic disorders", J. Autonomic Nervous Syst. 61:145-148.

Annable et al., 1972, "The Second International Reference Preparation of Erythropoietin, Human, Urinary, for Bioassay," Bull. Org, Mond. Sante, 47:99-112.

Arzneimittelkommission der Deutschen Arzteschaft, 2004, "Empfehlungen zur Therapie der Demenz," Arzneiverordrung in der Praxis, Band 31, Sonderheft 4 (w/English abstract).

Ashwell et al., 1973, "A Protein from Mammalian Liver that Specifically Binds Galactose-Terminated Glycoproteins," Meth. Enzymol., 50:287-291.

Ay et al., 1999, "Potential usefulness of basic fibroblast growth factor as a treatment for stroke," Cerebrovascular Disease 9:131-135.

Bany-Mohammed et al., 1996, "Recombinant human erythropoietin: possible role as an antioxident in premature rabbits," Pediatric Res. 40(3):381-387.

Barber et al., 2001, "De novo design of cytokine-based alpha helical binding domains display cytotoxic activity," Blood 98(11, part 2):132b-133b Abstract 4193.

Barber et al., 1994, "Erythropoietin and interleukin-2 activate distinct JAK kinase family members," Mol. Cell. Biol. 14(10):6506-6514.

Barbone et al., 1997, "Mutagenesis studies of the human erythropoietin receptor. Establishment of structure-function relationships," J. Biol. Chem. 272(8):4985-4992.

Barron et al., 1994, "Alternatively spiced mRNAs encoding soluble isoforms of the erythropoietin receptor in murine cell lines and bone marrow," Gene 147:263-8.

Baskaya et al., 1997, "The biphasic opening of the blood—brain barrier in the cortex and hippocampus after traumatic brain injury in rats," Neuroscience Lett. 226:33-36.

Bazan, 1989, "A novel family of growth factor receptors: a common binding domain in the growth hormone, prolactin, erythropoietin and IL-6 receptors, and the p75 IL-2 receptor beta-chain," Biochem. Biophys. Res. Commun. 164(2):788-795.

Belayev et al., 1996, "Quantitative evaluation of blood-brain barrier permeability following middle cerebral artery occlusion in rats," Brain Research 739:88-96.

Benit et al., 1993, "The 'WS motif' common to v-*mpl* and members of the cytokine receptor superfamily is dispensable for myeloproliferative leukemia virus pathogenicity," Oncogene 8:787-790.

Benyo et al., 1999, "Expression of erythropoietin receptor by trophoblast cells in the human placenta", Biol. Reproduct. 60:861-870.

Bernat et al., 2003, "Determination of the energetics governing the regulatory step in growth hormone-induced receptor homodimerization," PNAS vol. 100(3):952-57.

Bernaudin et al., 2000, "Neurons and astrocytes express EPO mRNA: oxygen-sensing mechanisms that involve the redox-state of the brain", Glia 30:271-278.

Besarab et al., 1998, "The effects of normal as compared with low hematocrit values in patients with cardiac disease who are receiving hemodialysis and epoietin," New England Journal of Medicine 339(9):584-590.

Bianchi et al., 2004, Erythropoietin both protects from and reverses experimental diabetic neuropathy, PNAS, vol. 101, pp. 823-828.

Bickel et al., 1993, "Pharmacologic effects in vivo in brain by vector-mediated peptide drug delivery," Proc Natl Acad Sci USA 90:2618-22.

Bickel et al., 1994, In vivo demonstration of subcellular localization of anti-transferrin receptor monoclonal antibody-colloidal gold conjugate in brain capillary endothelium. J Histochem Cytochem. vol. 42(11):1493-7.

Boado et al., 1998, Drug delivery of antisense molecules to the brain for treatment of Alzheimer's disease and cerebral AIDS. J Pharm Sci. vol. 87(11):1308-15.

Boger and Goldberg, 2001, "Cytokine receptor dimerization and activation: prospects for small molecule agonists," Bioorg. & Med. Chem., 9:557-562.

Bogoyevitch, 2004, "An update on the cardiac effects of erythropoietin cardioprotection by erythropoietin and the lessons learnt from studies in neuroprotection," Cardiovascular Research, vol. 63, pp. 208-216.

Boissel et al., 1993 "Erythropoietin structure-function relationships," J. Biol. Chem. vol. 268(21):15983-15993.

Bonsi et al., 1997, "An erythroid and megakaryocytic common precursor cell line (B1647) expressing both c-mpl and erythropoietin receptor (Epo-R) proliferates and modifies globin chain synthesis in response to megakaryocyte growth and development factor (MGDF) but not to erythropoietin (Epo)," Br. J. Haematol. 98:549-559.

Boudot et al., 1999, "Erythropoietin induces glycosylphosphatidylinositol hydroolysis. Possible involvement of phospholipase c-gamma(2)," J. Biol. Chem. 274(48):33966-33972.

Briggs et al., 1974, "Hepatic Clearance of Intact and Desialylated Erythropoietin," Am. J. Physiol., 227(6):1385-1388.

Brines et al., 2004, "Erythropoietin mediates tissue protection through an erythropoietin and common β-subunit heteroreceptor," PNAS, vol. 101(41):14907-14912.

Brizzi et al., 1991, "Hematopoietic growth factor receptors," Int. J. Cell. Cloning 9:274-300.

Bruneval et al., 1993, "Erythropoietin Synthesis by Tumor Cells in a Case of Meningioma Associated With Erythrocytosis," Blood, 81(6):1593-1597.

Buemi et al., 2002, "Recombinant human erythropoietin influences revascularization and healing in a rat model of random ischaemic flaps," Acta Derm. Venerol. 82:411-417.

Bundgaard and Moller, 1981, "Horseradish peroxidase and microperoxidase. Their purity and binding to serum proteins," J. Histochem. Cytochem. 29(3):331-336.

Calvillo et al., 2003, "Recombinant human erythropoietin protects the myocardium from ischemia-reperfusion injury and promotes beneficial remodeling," Proc. Nat. Acad. Sci. USA 100:4802-6.

Camiscoli et al., 1968, "Comparative Assay of Erythropoietin Standards," Annals New York Acad. Sci., 149:40-45.

Caravella et al., 1996, "A partial model of the erythropoietin receptor complex," Proteins 24:394-401.

Cardin et al., 2003, "Evolution of the atrial fibrillation substrate in experimental congestive heart failure: angiotensin-dependent and -independent pathways," Cardiovasc Res. 60(2): 315-325.

Cerneus and Van Der Ende, 1991, "Apical and basolateral transferrin receptors in polarized BeWo cells recycle through separate endosomes," J Cell Biol. 114(6):1149-1158.

Chin et al., 2000, "Production and processing of erythropoietin receptor transcripts in brain," Mol. Brain Res. 81: 29-42.

Claus-Walker et al., 1984, "Spinal Cord Injury and Serum Erythropoietin," Arch. Phys. Med. Rehabil., 65:370-374.

Cotes et al., 1961, "Bio-Assay of Erythropoietin in Mice Made Polycythaemic by Exposure to Air at a Reduced Pressure," Nature, 191:1065-1067.

Cotes et al., 1966, "The International Reference Preparation of Erythropoietin," Bull. Org. mond. Sante, 35:751-760.

Cotes, 1968, "Quantitative Estimation of Erythropoietin," Part 1. Assay and Standardization of Erythropoietin, Annals New York Acad. Sci., 149:12-17.

Cunningham and Wells, 1989, "High-resolution epitope mapping of hGH-receptor interactions by alanine-scanning mutagenesis," Science 244:1081-1085.

D'Andrea and Gonda, 2000, "A model for assembly and activation of the GM-CSF, IL-3 and IL-5 receptors: insight from activated mutants of the common beta subunit," Exp. Hematol. 28(3):231-243.

D'Andrea et al., 1998, "Dysregulated hematopoiesis and a progressive neurological disorder induced by expression of an activated form of the human common beta chain in transgenic mice," J. Clin. Invest. 102(11):1951-1960.

D'Andrea and Zon, 1990, "Erythropoietin receptor, Subunit structure and activation," J. Clin. Invest. 86(3):681-687.

Dale et al., 2002, "Stimulated platelets use serotonin to enhance their retention of procoagulant proteins on the cell surface," Nature 415:175-179.

Dame et al., 2001, "The biology of erythropoietin in the central nervous system and its neurotrophic and neuroprotective potential," Biol. Neonate 79(304):228-235.

Deguchi et al., 1999, "Retention of biologic activity of human epidermal growth factor following conjugation to a blood-brain barrier drug delivery vector via an extended poly(ethylene glycol) linker," Bioconjug Chem. 10(1):32-37.

Del Mastro and Venturi, 1998, "Strategies for the use of epoetin alfa in breast cancer patients," The Oncologist 3:314-318.

Denizot and Lang, 1986, "Rapid colorimetric assay for cell growth and survival—Modifications to the tetrazolium dye procedure giving improved sensitivity and reliability," J. Immunol. Meth. 89:271-277.

Diaz-Brinton and Yamazaki, 1998, "Advances and challenges in the prevention and treatment of Alzheimer's disease," Pharm. Res. 15(3):386-98.

Dietrich et al., 1993, "Microvascular and neuronal consequences of common carotid artery thrombosis and platelet embolization in rats," J. Neuropathol. Experimental Neurol. 52(4):351-360.

Dispersyn et al. 1999, Cardiomyocyte remodelling during myocardial hibernation and atrial fibrillation: prelude to apoptosis. Cardiovasc. Res. 43(4): 947-957.

Dobbin et al., 1989, "Transient blood-brain barrier permeability following profound temporary global ischaemia: An experimental study using $^{14}C$-A1B," J. of Cerebral Blood Flow Metabolism 9:71-78.

Dong et al., 1992, "Receptor binding of asialoerythropoietin," J. Cell. Biochem. 48(3):269-276.

Dordal et al., 1985, "The Role of Carbohydrate in Erythropoietin Action," Endocrinol., 116(6):2293-2299.

Dox et al., 1993, "The Harper Collins Illustrated Medical Dictionary," Harper Collins Publishers, Inc. New York, 1993.

Dube et al, 1988, "Glycosylation at Specific Sites of Erythropoietin is Essential or Biosynthesis, Secretion, and Biological Function," J. Biol. Chem., 263(33):17516-17521.

Eckart, 2002, "Anaemia of critical illness—implications for understanding and treating rHuEPO resistance," Nephrol Dial Transplant 17, Suppl 5, pp. 48-55.

Egrie and Browne, 2001, "Development and characterization of novel erythropoiesis stimulating protein (NESP)," Nephrol. Dial. Transplant 16 (suppl. 3):3-13.

Ehrenreich, 2004, "Erythropoietin: a candidate compound for neuroprotection in schizophrenia," Molecular Psychiatry, 9:42-54.

Ehrenreich, 2004 "A boost for translational neuroscience," Science, vol. 305:184-185.

Elliott et al., 1997, "Mapping of the active site of recombinant human erythropoietin," Blood 89(2):493-502.

Emir, 2004, "Erythropoietin on bcl-2 gene expression in rat cardiac myocytes after traumatic brain injury," Transplantation Proceedings, vol. 36, pp. 2935-2938.

Erbayraktar et al., 2003, "Asialoerythropoietin is a nonerythropoietic cytokine with broad neuroprotective activity in vivo," Proc. Natl. Acad. Sci. U. S. A. 100(11):6741-6.

Eur. Pharmacopoeia, 1997, Sainte-Ruffinc, France, Maisonneuve p. 5.

Eur. Pharmacopoeia, Strasbourg, Council of Europe, Suppl. 2001, pp. 777-782.

Farrell et al., 2001, "Erythropoietin crosses the blood brain barrier", Blood 98:148b (abstr. #4265; 43rd Annual Meeting of the American Society of Hematology, Orlando FL, Dec. 7-11, 2001).

Faruki and Kiss, 1995, Erythropoietin, transfusion medicine update, The Institute for Transfusion Medicine, path.uprnc.edu/consult/ria/july_1995.html.

Feigin et al., 2002. "Recent advances in Huntington's disease: implications for experimental therapeutics," Curr. Opin. Neurol. 15(4):483-489.

Fishbein et al. 1981, "Early phase acute myocardial infarct size quantification: validation of the triphenyl tetrazolium chloride tissue enzyme staining technique," Am. Heart Journal 101(5): 593-600.

Foresta et al., 1994, "Erythropoietin stimulates testosterone production in man," J. Clin. Endocrinol. Metabol. 78(3):753-756.

Frank, 2002, "Minireview: Receptor dimerization in GH and erythropoietin action—it takes two to tango, but how?" Endocrinology 143(1):2-10.

Freshney, 1983, "Culture of animal cells," A Manual of Basic Technique, A R. Liss, Inc. NY 1983, pp. 3-4.

Friden, 1996, "Utilization of an endogenous cellular transport system for the delivery of therapeutics across the blood-brain barrier," J. Controlled Release 46:117-28.

Friedman et al., 1995, "Erythropoietin in diabetic macular edema and renal insufficiency," Am. J. Kidney Disease 26(1), pp. 202-208.

Fukuda et al., 1989, "Survival of Recombinant Erythropoietin in the Circulation: The Role of Carbohydrates," Blood, 73(1):84-89.

Fujita et al., 1997, "Role of alternative splicing of the rat erythropoietin receptor gene in normal and erythroleukemia cells," Leukemia, 11 (Suppl. 3): 444-445.

Fung and Greene, 1990, "The human interleukin-2 receptor: insights into subunit structure and growth signal transduction," Semin. Immunol. 2:119-128.

Gabriel et al., 1998, "High-dose recombinant human erythropoietin stimulates reticulocyte production in patients with multiple organ dysfunction syndrome," J. Trauma 44(2):361-367.

Gaertner et al., 1994, "Chemo-enzymic backbone engineering of proteins," J. Biol. Chem. 269(10):7224-7230.

Garcia et al., 1996, "Ischemic stroke and incomplete infarction," Stroke, vol. 27(4):761-765.

Garthoff, 1995, "Safety and Efficacy Testing of Hormones and Related Products," The Report and Recommendations of ECVAM Workshop 9, A.T.L.A., 23:699-711.

Genbank No. M59941, 1994 (Human GM-CSF Receptor β chain).

Goldberg et al., 2002, "Erythropoietin mimetics derived from solution phase combinatorial libraries," J. Amer. Chem Soc. 124(4):544-555.

Goldwasser et al., 1975, "Erythropoietin: Assay and Study of Its Mode of Action," Methods in Enzymology, Hormone Action Part B, Peptides Hormones, 1975 Academic Press, vol. 28, pp. 109-121.

Goldwasser et al., 1974, "On the Mechanism of Erythropoietin-Induced Differentiation," XIII. The Role of Sialic Acid in Erythropoietin Action, J. Biol. Chem., 249(13):4202-4206.

Goldwasser et al., 1975, "An Assay for Erythropoietin in Vitro at the Milliunit Level," Endo., 97(2):315-323.

Grasso et al., 2006, "Amelioration of spinal cord compressive injury by pharmacological preconditioning with erythropoietin and a nonerythropoietic erythropoietin derivative," J. Neurosurg. Spine 4(4):310-318.

Green, 1998, "Clomethiazole (Zendra®) in acute ischemic stroke: Basic pharmacology and biochemistry and clinical efficacy," Pharmacol Ther. 80(2):123-147.

Greenberg et al. 1995, "Congestive heart failure and sleep apnoea-possible mechanisms and effect of CPAP therapy," J. Sleep Res. 4(S1): 130-134.

Gregory et al., 1999, "GATA-1 and erythropoietin cooperate to promote erythroid cell survival by regulating bcl-$x_L$ expression", Blood 94:87-96.

Grimm et al., 2002, "HIF-1-induced erythropoietin in the hypoxic retina protects against light-induced retinal degeneration," Nature Medicine 8(7):718-724.

Grotzinger, 2002, "Molecular mechanisms of cytokine receptor activation," Biochim. Biophys. Acta. 1592:215-223.

Gruber et al., 2002, "The thrombin mutant W215A/E217A shows safe and potent anticoagulant and antithrombotic effects in vivo," J. Biol. Chem. 277(31):27581-27584.

Gunasekar et al., 2001, "Mechanisms of the apoptotic and necrotic actions of trimethyltin in cerebellar grranule cells," Toxicological Sciences 64:83-89.

Hammond et al., 1968, "Production, Utilization and Excretion of Erythropoietin: I. Chronic Anemias. II. Aplastic Crisis. III. Erythropoietic Effects of Normal Plasma," Annals NY Academy of Sciences 149:516-527.

Hanazono et al., 1995, "Erythropoietin induces tyrosine phosphorylation of the beta chain of the GM-CSF receptor," Biochem. Biophys. Res. Comm. 208(3):1060-1066.

Hancher et al., 1974, "Recovery of Erythropoietin from Anemic Sheep Plasma," Biotechnology and Bioengineering 16:1069-1079.

Hansen, et al., 2000, "A randomized, blinded placebo controlled, phase II, dose-finding study of ARANESP in patients with lymphoproliferative malignancies," Blood, vol. 96(11), pp. 155b, Abstr. 4371.

Harris et al. 1992, "Ligand binding properties of the human erythropoietin receptor extracellular domain expressed in Escherichia coli," J. Biol. Chem. 267(21):15205-15209.

Harris et al., 2000, "Purification and characterization of yeast-expressed erythropoietin (R103A), an erythropoietin antagonist," Blood 96(11, part 2):154b Abstract 4366.

Harris et al., 2001, "Characterization of the yeast-expressed erythropoietin mutant, Epo (R103A), a specific inhibitor of human primary hematopoietic cell erythropoiesis," Blood, 98(11, part 1):77a Abstract 319.

Harris K.W., 2004, "Signal transduction in myeloid differentiation," Federal Research in Progress database, FRP 03-05, ID No. 136456, Comp &. Dist. By NTIS.

Hassan and Freund, 1995. "Review of megakaryoblastic cell lines—Characteristic biological features of human megakaryoblastic leukaemia cell lines," Leuk. Res. 19(9):589-594.

Hörkkö et al., 1992, "Carbamylation-induced alterations in low-density lipoprotein metabolism," Kidney Int. 41(5)1175-1181.

Horton et al., 1991, "Von Hippel-Lindau Disease and Erythrocytosis: Radioimmunoassay of Erythropoietin in Cyst Fluid From a Brainstem Hemangioblastoma," Neurology, 41:753-754.

Huwyler and Pardridge, 1998, "Examination of blood-brain barrier transferrin receptor by confocal fluorescent microscopy of unfixed isolated rat brain capillaries," J. Neurochem. 70(2):883-886.

Huwyler et al., 1997, "Receptor mediated delivery of daunomycin using immunoliposomes: pharmacokinetics and tissue distribution in the rat," J Pharmacol Exp Ther. 282(3):1541-1546.

Imada et al., 1992, "Interleukin-2 (IL-2) induces erythroid differentiation and tyrosine phosphorylation in ELM-I-1 cells transfected with a human IL-2 receptor beta chain cDNA," Biochem. Biophys. Res. Commun. 188(1):352-357.

Imai et al., 1990, "Physicochemical and Biological Characterization of Asialoerythropoietin," Eur. J. Biochem., 194:457-462.

Iseki et al., 1996, "Increased risk of cardiovascular disease with erythropoietin in chronic dialysis patients," Nephron 72:30-36.

Itoh et al., 1990, "Cloning of an interleukin-3 receptor gene: a member of a distinct receptor gene family," Science 247:324-327.

Jacobs et al., 1985, "Isolation and characterization of genomic and cDNA clones of human erythropoietin," Nature 313(28):806-810.

Jenkins et al., 1999, "A cell type-specific constitutive point mutant of the common β-subunit of the human granulocyte-macrophage colony-stimulating factor (GM-CSF), interleukin (IL)-3, and IL-5 receptors requires the GM-CSF receptor α-subunit for activation," J. Biol. Chem. 274(13):8669-8677.

Jiang et al., 1996, "Delayed intravenous administration of basic fibroblast growth factor (bFGF) reduces infarct volume in a model of focal cerebral ischemia/reperfusion in the rat," J.Neurological Sciences 139:173-179.

Jones et al., 1990, "Human erythropoietin receptor: cloning, expression, and biologic characterization," Blood 76(1):31-35.

Jooss et al., 1996, "Cyclophosphamide diminishes inflammation and prolongs transgene expression following delivery of adenoviral vectors to mouse liver and lung," Hum. Gene Ther. 7(13):1555-1566.

Josse et al., 1999, "Human serum paraoxonase (PON1): Identification of essential amino acid residues by group-selective labelling and site-directed mutagenesis," Chem, Biol. Interact. 119-120:71-78.

Josse et al., 1999, "Tryptophan residue(s) as major components of the human serum paraoxonase active site," Chem. Biol. Interact. 119-120:79-84.

Jubinsky et al., 1996, "The β c component of the granulocyte-macrophage colony-stimulating factor (GM-CSF)/interleukin 3 (IL-3)/IL-5 receptor interacts with a hybrid GM-CSF/erythropoietin receptor to influence proliferation and β-globin mRNA expression," Mol. Med. 2(6):766-773.

Jubinsky et al., 1997, "The β chain of the interleukin-3 receptor functionally associates with the erythropoietin receptor," Blood 90(5):1867-1873.

Juul et al., 1998, "Tissue distribution of erythropoietin and erythropoietin receptor in the developing human fetus", Early Human Devel. 52(3):235-249.

Juul et al., 2001, "Recombinant erythropoietin (EPO) crosses the blood brain barrier (BBB) in preterm fetal sheep", Soc. for Neuroscience Abstracts 27(1):929 (31st Annual Meeting of the Society for Neuroscience, San Diego, CA Nov. 10-15, 2001).

Juul, S. 2002, "Erythropoietin in the central nervous system, and its use to prevent hypoxic-ischemic brain damage," Acta Paediatr. Supp. 438:36-42.

Kang et al., 1994, "Pharmacokinetics and saturable blood-brain barrier transport of biotin bound to a conjugate of avidin and a monoclonal antibody to the transferrin receptor," Drug Metab. Dispos. 22(1):99-105.

Kawasaki et al., 2001, "Structural analysis of sulfated N-linked oligosaccharides in erythropoietin," Glycobiology 11(12):1043-1049.

Kaye DM et al., 2003, Feasibility and short-term efficacy of percutaneous mitral annular reduction for the therapy of heart failure-induced mitral regurgitation. Circulation 108:1795-1797.

Keighley, 1968, "Further Experiences with Assays, Units, and Standards of Erythropoietin," Annal New York Acad. Sci., 149:18-24.

Keswani et al., 2004, "A novel endogenous erythropoietin mediated pathway prevents axonal degeneration," Ann. Neurol. vol. 56(6):815-826.

Kirito et al., 2002, "Identification of the human erythropoietin receptor region required for Stat1 and Stat3 activation," Blood 99(1):102-110.

Kishimoto and Tavassoli, 1987, "Transendothelial transport (transcytosis) of iron-transferrin complex in the rat liver," Am. J. Anat. 178:241-249.

Kitamura et al., 1989, "Identification and analysis of human erythropoietin receptors on a factor-dependent cell line, TF-1," Blood 73(2):375-80.

Kohama et al., 2000, "Large Uterine Myoma with Erythropoietin Messenger RNA and Erythrocytosis," Obstetrics and Gynecology, 96(5):826-828.

Krafte-Jacobs et al., 1996, "Circulating erythropoietin and interleukin-6 concentrations increase in critically ill children with sepsis and septic shock," Crit. Care Med. 24(9):1455-1459.

Kumral et al., 2004, "Erythropoietin improves long-term spatial memory deficits and brain injury following neonatal hypoxia-ischemia in rat," Behavioral Brain Research, vol. 153:77-86.

Kuroiwa et al., 1985, "The biphasic opening of the blood-brain barrier to proteins following temporary middle cerebral artery occlusion," Acta Neurophotalogica 68:122-129.

Lai et al., 1996, "The molecular role of the common gamma $_c$ subunit in signal transduction reveals functional asymmetry within multimeric cytokine receptor complexes." Proc. Natl. Acad. Sci. USA 93:231-235.

Lee et al. 1998, "Conditional lineage ablation to model human diseases," Proc. Natl. Acad. Sci. USA 95:11371-11376.

Leitgeb et al., 1994, "Quality of life in chronic anemia of cancer during treatment with recombinant human erythropoietin", Cancer; 73(10):2535-2542.

Leist et al., 2004, "Derivatives of erythropoietin that are tissue protective but not erythropoietic," Science, vol. 305, pp, 239-242.

Lewis et al., 1996, "Molecular characterization of the 7q deletion in myeloid disorders," Br. J. Haematol. 93:75-80.

Lewis et al., 2004, "Opposing effects of PI3 kinase pathway activation on human myeloid and erythroid progenitor cell proliferation and differentiation in vitro," Exp. Hematol. 32:36-44.

Li et al., 1996, "Erythropoietin receptors are expressed in the central nervous system of mid-trimester human fetuses", Pediatr. Res. 40(3):376-380.

Linsley et al., 994, "Applications of electrospray mass spectrometry to erythropoietin N- and O-linked glycans," Anal. Biochem. 219:207-217.

Liu et al., 1994, "Multiple cytokines stimulate the binding of a common 145-kilodalton protein tp Shc at the Grb2 recognition site of Shc." Mol. Cell. Biol. 14(10):6926-6935.

Liu et al., 1996, "Transgenic mice containing the human erythropoietin receptor gene exhibit correct hematopoietic and neural expression", Proc. Assoc. Am. Physicians 108(6):449-454.

Livnah et al., 1999, "Crystallographic evidence for preformed dimers of erythropoietin receptor before ligand activation," Science 283:987-990.

Loberg et al., 1993, "Neuronal uptake of plasma proteins after transient cerebral ischemia/hypoxia," APMIS 101:777-783.

Lowy et al., 1960, "Inactivation of Erythropoietin by Neuraminidase and by Mild Substitution Reactions," Nature, 185:102-103.

Lu et al., 2005, "Erythropoietin enhances neurogenesis and restores spatial memory in rats after traumatic brain injury," J. of Neurotrauma, vol. 22(9), pp. 1011-1017.

Magnanti et al., 2001, "Erythropoietin expression in primary rat Sertoli and peritubular myoid cells," Blood 98(9):2872-2874.

Maitani et al., 1996, "Oral administration of recombinant human erythropoietin in liposomes in rats: influence of lipid composition and size of liposomes on bioavailability", J. Pharm. Sci.; 85(4):440-45.

Massague, 1987, "The TGF-beta family of growth and differentiation factors," Cell 49:437-438.

Matsuyama et al., 2000, "Erythrocytosis Caused by an Erythropoietin-Producing Hepatocellular Carcinoma," J. Surg. Oncology, 75:197-202.

Matthews et al., 1996, "A sequential dimerization mechanism for erythropoietin receptor activation," Proc. Natl. Acad. Sci. USA 93:9471-9476.

McClure et al., 2001, "GM-CSF binding to its receptor induces oligomerisation of the common beta-subunit," Cytokine 13(4):240-243.

Means and Krantz, 1996, "Inhibition of human erythroid colony-forming units by inteferons α and β: differing mechanisms despite shared receptor," Exp. Hematol. 24:204-208.

Menzies and Ellis, 1990 Intestinal obstruction from adhesions—how big is the problem?, Ann. R. Coll. Surg. Engl. 72:60-63.

Menzies et al., 1990, "Extravasation of albumin in ischaemia brain oedema," Acta Neurochirurgica, Suppl. 51:220-222.

Mioni et al., 1992, "Evidence for specific binding and stimulatory effects of recombinant human erythropoietin on isolated adult rat Leydig cells", Acta Endocrinologica 127:459-465.

Miu et al., 2004, "Have no fear, erythropoietin is here, erythropoietin protects fear conditioning performances after functional inactivation of the amygdala," Behavioral Brain Research, vol. 155, pp. 223-229.

Miyake et al., 1977, "Purification of Human Erythropoietin," J. Biol. Chem., 252(15):5558-5564.

Mogensen et al., 2004, Erythropoietin improves place learning in fimbria-fornix-transected rats and modifies the search pattern of normal rats, Pharmacology, Biochemistry and Behavior, vol. 77:381-390.

Morell et al., 1968, "Physical and Chemical Studies on Ceruloplasmin," Metabolic Studies on Sialic Acid-Free Ceruloplasmin In Vivo, J. Biol. Chem., 243(1):155-159.

Mun and Golper, 2000, "Impaired biological activity of erythropoietin by cyanate carbamylation," Blood Purif 18:13-17.

Murakami et al., 1991, "Critical cytoplasmic region of the interleukin 6 signal transducer gp130 is conserved in the cytokine receptor family," Proc. Natl. Acad. Sci. USA 88(24):11349-11353.

Murray, 1996, Harpers Illustrated Biochemistry 26$^{th}$ ed. pp. 524-526, McGraw-Hill Co.

Nagao et al., 1992, "Production and ligand-binding characteristics of the soluble form of murine erythropoietin receptor," Biochem. Biophys. Res. Comm. 188(2):888-897.

Nakamura et al., 1998, "Elevated levels of erythropoietin in cerebrospinal fluid of depressed patients", Am. J. Med. Sci. 315(3):199-201.

Naranda et al., 2002, "Activation of erythropoietin receptor through a novel extracellular binding site," Endocrinology 143(6):2293-2302.

Nathan, 1994, "Studies of hybrid hematopoietic growth factor receptors," Stem Cells 12 (Suppl 1):27-35.

Nestler et al., 1985 "Stimulation of rat ovarian cell steroidogenesis by high density lipoproteins modified with tetranitromethane," J. Biol Chem. 260(12):7316-21.

Nimtz and Conradt, 1993, "Characterization of a phosphorylated oligosaccharide from erythropoietin expressed in recombinant BHK cells," Glycoconj. J. 10(4):259, Abstr. S6.7.

Noguchi et al., 1991, "Cloning of the human erythropoietin receptor gene," Blood 78(10):2548-2556.

Ohta et al., 2001, "Selective glycopeptide mapping of erythropoietin by on-line high-performance liquid chromatography-electrospray ionization mass spectrometry," J. Chromatography A, 910:1-11.

Okada et al., 1996, "Erythropoietin stimulates proliferation of rat-cultured gastric mucosal cells", Digestion 57:328-332.

Opitz et al. 1995, "Arrhythmias and Death After Coronary Artery Occlusion in the Rat," Circulation. 92(2):253-261.

Opitz et al. 1998, "Effects of reperfusion on arrhythmias and death after coronary artery occlusion in the rat: increased electrical stability independent of myocardial salvage," J. Am. Coll. Cardiol. 32(1): 261-267.

Page et al., 1996, "A sensitive human cell line based bioassay for megakaryocyte growth and development factor or thrombopoietin," Cytokine 8(1):66-69.

Pantoliano et al., 1987, "Protein engineering of subtilisin BPN': Enhanced stabilization through the introduction of two cysteines to form a disulfide bond," Biochemistry 26:2077-2082.

Pardridge, 1998, "CNS drug design based on principles of blood-brain barrier transport." J Neurochem. 70:1781-92.

Park and Hong, 1997, "Development of an in vitro bioassay system for human thrombopoietin by constructing a recombinant murine cell line expressing human thrombopoietin receptor," Mol. Cells. 7(6):699-704.

Pazur et al., 2000, "Oligosaccharides as immuno-determinants of erythropoietin for two sets of anti-carbohydrates antibodies," J. Protein Chem. vol. 19(8):631-635.

Pedersen et al., 1995, "The interaction of beta 2-microglobulin (β 2m) with mouse class 1 major histocompatibility antigens and its ability to support peptide binding. A comparison of human and mouse beta 2m," Eur. J. Immunol. 25:1609-16.

Peng et al., 2000, "HPLC/ESI MS and MALDI/TOF MS analysis of microheterogeneity of the N-linked oligosaccharides of recombinant human erythropoietin," Yao Xue Bao (Acta Pharmaceutica Sinica 35(10):770-773 (w/ English abstract)

Penny and Forget, 1991, "Genomic organization of the human erythropoietin receptor gene," Genomics 11(4):974-980.

Petito, 1979, "Early and late mechanisms of increased vascular permeability following experimental cerebral infarction," J. Neuropatholo Exp. Neurol. 38(3):222-34.

Pfeffer et al., 1991, Progressive ventricular remodeling in rat with myocardial infarction. Am. J. Physiol. 260(5 Pt 2): H1406-1414.

Physicians' Desk Reference, 1995, 49$^{th}$ Edition (Medical Economics Data Production Company, Montvale, NJ), pp. 1765-1769.

Physicians' Desk Reference, 2000 (Medical Economics Company, Inc. Montvale, NJ), pp. 519-525 and 2125-2131.

Pilbeam et al., 1993, "Comparison of the effects of various lengths of synthetic human parathyroid hormone-related peptide (hPTHrP) of malignancy on bone resorption and formation in organ culture," Bone 14:717-720.

Plapp et al., 1971, "Activity of bovine pancreatic deoxyribonuclease A with modified amino groups," J. Biol. Chem. 246(4):939-45.

Ponger et al., 1983, "Preparation of high-potency, non-aggregating insulins using a novel sulfation procedure," Diabetes 32:1087-1091.

Qui et al., 1998, "Homodimerization restores biological activity to an inactive erythropoietin mutant," J. Biol. Chem. 273(18):11173-11176.

Remick, 2003, "Cytokine therapeutics for the treatment of sepsis: why has nothing worked?" Current Pharmaceutical Design, 9:75-82.

Remy et al., 1999, "Erythropoietin receptor activation by a ligand-induced conformation change," Science 283:990-993.

Robinson et al., 1975, "Tetanus toxin. The effect of chemical modifications on toxicity, immunogenicity, and conformation," J. Biol. Chem. 250(18):7435-42.

Romanovsky et al., 1996, "First and second phases of biphasic fever: two sequential stages of the sickness syndrome?" Am. J. Physiol. 271(1 pt. 2):R244-R253.

Rosenbaum et al., 1997, "Retinal ischemia leads to apoptosis which is ameliorated by aurintricarboxylic acid," Vision Res., 37(24):3445-3451.

Rush et al., 1993, "Peptide mapping and evaluation of glycopeptide microheterogeneity derived from endoproteinase digestion of erythropoietin by affinity high-performance capillary electrophoresis," Anal. Chem. 65(14):1834-1842.

Rush et al., 1995, "Microheterogeneity of erythropoietin carbohydrate structure," Anal. Chemistry, 67(8):1442-1452.

Saito et al., 1990, "Role of neuroexcitation in development of blood-brain barrier and oedematous changes following cerebral ischaemia and traumatic brain injury," Acta Neurochirurgica, Suppl. 51:186-188.

Schussler et al., 1998, "Erythropoietin and obstetrical influences," Zeitschrift fur Geburtshilfe und Neonatologie 202(2):64-68 (With English Abstract).

Scott et al., 2000, "Reassessment of interactions between hematopoietic receptors using common beta-chain and interleukin-3-specific receptor beta-chain-null cells: no evidence of functional interactions with receptors for erythropoietin, granulocyte colony-stimulating factor, or stem cell factor," Blood 96(4):1588-1590.

Shikama et al., 1996, "A constitutively activated chimeric cytokine receptor confers factor-independent growth in hematopoietic cell lines," Blood 88(2):455-464.

Shulman et al., 2002, "Current drug treatment of Sepsis," Hospital Pharmacist 9:97-107.

Soda et al., 1984, "Transendothelial transport (transcytosis) of iron-transferrin complex in the bone marrow," J Ultrastruct Res. 88(1):18-29.

Stark, 1967, "Modification of proteins with cyanate" Methods Enzymol. 11:590-594.

Stenesh, J., 1989, Dictionary of Biochemistry and Molecular Biology, $2^{nd}$ Ed., New York, John Wiley & Sons, p. 122, p. 508.

Sturm et al., 2005, "Recombinant human erythropoietin: effects on frataxin expression in vitro," European J. of Clinical Investigation, vol. 35, pp. 711-717.

Suzuki et al., 1983, "The effects of 5-minute ischemia in Mongolian gerbils: I. Blood—brain barrier, cerebral blood flow, and local cerebral glucose utilization changes," Acta Neuropathologica (Berl) 60:207-216.

Sweeney et al., 1995, "Cellular mechanisms involved in brain ischemia," Can. J. Physiol. Pharmacol. vol. 73:1525-1535.

Swiss Prot Accession No. P32927, Oct. 1, 1993 (IL3 RB Human).

Syed et al., 1998, "Efficiency of signaling through cytokine receptors depends critically on receptor orientation," Nature 395:511-516.

Takahashi, 1977, "The reactions of phenylglyoxal and related reagents with amino acids," J. Biochem., vol. 81:395-402.

Temple et al., 1995, "Recombinant erythropoietin improves cognitive function in patients maintained on chronic ambulatory peritoneal dialysis," Nephrology Dialysis Transplantation, vol. 10:1733-1738.

Teien et al., 1995. Doppler evaluation of severity of mitral regurgitation: relation to pulmonary venous blood flow patterns in an animal study. J. Am. Coll. Cardiol. 25(1): 264-268.

Tojo et al., 1987, "Identification of erythropoietin receptors on fetal liver erythroid cells," Biochem. Biophys. Res. Commun. 148(1):443-448.

Urena, 2002, "Treatment of anemia in chronic renal failure by a long-active activator of erythropoiesis," Press Medicale 31(11):505-514 (w/ English abstract).

Van Der Meer et al., 2005, "Erythropoietin induces neovascularization and improves cardiac function in rats with heart failure after myocardial infraction," JACC, vol. 46(11) pp. 125-133.

Vansteenkiste et al., 2003, "Darbepoietin alfa: a new approach to the treatment of chemotherapy-induced anaemia," Expert Opin. Biol. Ther. vol. 3(3):501-508.

Vezzani et al., 1999, "Interleukin-1-β immunoreactivity and microglia are enhanced in the rat hippocampus by focal kainate application: Functional evidence for enhancement of electrographic seizures," J. Neurosci. 19(12):5054-65.

Vezzani et al., 1986, "Anticonvulsant drugs effective against human temporal lobe epilepsy prevent seizures but not neurotoxicity induced in rats by quinolinic acid: Electroencephalographic, behavioral and histological assessments," J. Pharmacol. Exp. Ther. 239(1):256-263.

Vukicevic et al., 1996, "Induction of nephrogenic mesenchyme by osteogenic protein 1 (bone morphogenetic protein 7)," PNAS USA 93:9021-9026.

Wauben-Penris et al., 1988, "The release of iron by Sertoli cells in culture," Biol. Reprod. 38:1105-1113.

Wells, 1990, "Additivity of mutational effects in proteins," Biochemistry 29(37):8509-8517.

Wen et al., 1994, "Erythropoietin structure-function relationships," J. Biol. Chem. 269(36):22839-22846.

Widness et al., 1995, "Erythropoietin transplacental passage—Review of animal studies," J. Perinat. Med. 23: 61-70.

Williamson et al., 1993, "Protein and lipid kinase activation cascades in interleukin-2 receptor signalling," Semin. Immunol. 5(5):337-344.

Winkelmann et al., 1990, "The gene for the human erythropoietin receptor: analysis of the coding sequence and assignment to chromosome 19p." Blood 76(1):24-30.

Wit et al., 1992, "Experimental models of ventricular tachycardia and fibrillation caused by ischemia and infarction," Circulation 85 Suppl. 1:1-32-1-42.

Wojchowski and Caslake, 1989, "Biotinylated recombinant human erythropoietins: bioactivity and utility as receptor ligands," Blood, vol. 74(3):952-958.

Wolf et al,, 1997, "Erythropoietin administration increases production and reactivity of platelets in dogs," Thromb. Haemost. 78:1505-1509.

Wu and Pardridge, 1996, "Central nervous system pharmacologic effect in conscious rats after intravenous injection of a biotinylated vasoactive intestinal peptide analog coupled to a blood-brain barrier drug delivery system," J Pharmacol Exp Ther. 279(1):77-83

Xiao et al., 1998, "Fibrinogen deficiency is compatible with the development of atherosclerosis in mice," J. Clin Invest. 101(5):1184-1194.

Yamamura et al., 1992, "Distinct downstream signaling mechanism between erythropoietin receptor and interleukin-2 receptor," EMBO J. 11(13):4909-4915.

Yang et al., 1994, "Reperfusion-induced injury to the blood-brain barrier after middle-cerebral artery occlusion in rats," Stroke, vol. 25(8):1658-1665.

Yet et al., 1993, "The extracytoplasmic domain of the erythropoietin receptor forms a monomeric complex with erythropoietin," Blood 82(6):1713-1719.

Yoshimura et al., 1995, "A novel cytokine-inducible gene CIS encodes an SH2-containing protein that binds to tyrosine-phosphorylated interleukin 3 and erythropoietin receptors," EMBO J. 14(12):2816-2826.

Yoshimura et al., 1996, "Mouse oncostatin M: an immediate early gene induced by multiple cytokines through the JAK-STAT5 pathway," EMBO J. 15(5):1055-1063.

Yoshimura et al., 1996, "Physician Education: The Erythropoietin Receptor and Signal Transduction," Oncologist 1(5):337-339.

Zeng, 1991, "Lysine modification of metallothionein by carbamylation and guanidination," Methods Enzymol. 205:433-437.

Zhang et al., 2006, "Erythropoietin protects CA 1 neurons against global cerebral ischemia in rat: potential signaling mechanisms," J. Neurosci. Res, 83:1241-51.

Zhu et al., 2002, "Detecting and responding to hypoxia," Nephrol. Dial. Transplant. 17 Suppl 1:3-7.

Office Action, U.S. Appl. No. 09/547,220, date mailed: May 8, 2002.
Office Action, U.S. Appl. No. 09/547,220, date mailed: Jun. 13, 2002.
Office Action, U.S. Appl. No. 09/547,220, date mailed: Oct. 22, 2002.
Office Action, U.S. Appl. No. 09/547,220, date mailed: Jan. 28, 2003.
Office Action, U.S. Appl. No. 09/547,220, date mailed: Dec. 2. 2003.
Office Action, U.S. Appl. No. 09/547,220, date mailed: Sep. 22, 2004.
Office Action, U.S. Appl. No. 09/547,220. date mailed: Jun. 6, 2005.
Office Action, U.S. Appl. No. 09/547,220, date mailed: Feb. 22, 2006.
Office Action, U.S. Appl. No. 09/547,220, date mailed: Aug. 31, 2006.
Notice of Abandonment, U.S. Appl. No. 09/547,220, date mailed: Jun. 26, 2007.
Office Action, U.S. Appl. No. 09/716,960, date mailed: Aug. 26, 2002.
Office Action, U.S. Appl. No. 09/716,960, date mailed: Jul. 25, 2003.
Office Action, U.S. Appl. No. 09/716,960, date mailed: Mar. 8, 2004.
Office Action, U.S. Appl. No. 09/716,960, date mailed: Sep. 16, 2004.
Office Action, U.S. Appl. No. 09/716,960, date mailed: Jan. 19, 2005.
Office Action, U.S. Appl. No. 09/716,960, date mailed: May 8, 2006.
Office Action, U.S. Appl. No. 09/716,960, date mailed: Feb. 1, 2007.
Office Action, U.S. Appl. No. 09/716,960, date mailed: Oct. 16, 2007.

Office Action, U.S. Appl. No. 09/716,960, date mailed: Dec. 6, 2007.
Notice of Allowance, U.S. Appl. No. 09/716,960, date mailed: Feb. 21, 2008.
Office Action, U.S. Appl. No. 09/717,057, date mailed: May 17, 2002.
Office Action, U.S. Appl. No. 09/717,057, date mailed: Nov. 1, 2002.
Office Action, U.S. Appl. No. 09/717,057, date mailed: Jul. 15, 2003.
Office Action, U.S. Appl. No. 09/717,057, date mailed: Apr. 5, 2004.
Office Action, U.S. Appl. No. 09/717,057, date mailed: Oct. 26, 2004.
Office Action, U.S. Appl. No. 09/717,057, date mailed: Apr. 5, 2005.
Office Action, U.S. Appl. No. 09/717,057, date mailed: Jan. 9, 2006.
Office Action, U.S. Appl. No. 09/717,057, date mailed: Oct. 10, 2006.
Notice of Allowance, U.S. Appl. No. 09/717,057, date mailed: May 18, 2007.
Office Action, U.S. Appl. No. 09/717,053, date mailed: May 13, 2002.
Office Action, U.S. Appl. No. 09/717,053, date mailed: Jul. 16, 2002.
Office Action, U.S. Appl. No. 09/717,053, date mailed: Apr. 9, 2003.
Office Action, U.S. Appl. No. 09/717,053, date mailed: Oct. 15, 2003.
Office Action, U.S. Appl. No. 09/717,053, date mailed: Apr. 20, 2004.
Office Action, U.S. Appl. No. 09/717,053, date mailed: May 3, 2005.
Office Action, U.S. Appl. No. 09/717,053, date mailed: Jan. 20, 2006.
Office Action, U.S. Appl. No. 09/717,053, date mailed: Oct. 24, 2006.
Notice of Allowance, U.S. Appl. No. 09/717,053, date mailed: Apr. 26, 2007.
Office Action, U.S. Appl. No. 09/753,132, date mailed: Jan. 25, 2002.
Office Action, U.S. Appl. No. 10/185,841, date mailed: Apr. 28, 2005.
Office Action, U.S. Appl. No. 10/185,841, date mailed: Jan. 18, 2006.
Office Action, U.S. Appl. No. 10/185,841, date mailed: Oct. 5, 2006.
Office Action, U.S. Appl. No. 10/185,841, date mailed: Jun. 27, 2007.
Interview Summary, U.S. Appl. No. 10/185,841, date mailed: Feb. 27, 2008.
Office Action, U.S. Appl. No. 10/185,841, date mailed: Jan. 9, 2009.
Notice of Allowance, U.S. Appl. No. 10/185,841, date mailed: Apr. 10, 2009.
Notice of Allowance, U.S. Appl. No. 10/185,841, date mailed: Oct. 22, 2009.
Office Action, U.S. Appl. No. 10/188,905, date mailed: Aug. 22, 2005.
Office Action, U.S. Appl. No. 10/188,905, date mailed: Mar. 21, 2006.
Office Action, U.S. Appl. No. 10/188,905, date mailed: Dec. 7, 2006.
Office Action, U.S. Appl. No. 10/188,905, date mailed: May 28, 2008 (Interview Summary May 21, 2008).
Office Action, U.S. Appl. No. 10/188,905, date mailed: Oct. 15, 2008.
Office Action, U.S. Appl. No. 10/188,905, date mailed: Feb. 12, 2009 (Interview Summary Feb. 4, 2009).
Office Action, U.S. Appl. No. 10/351,640, date mailed: Dec. 13, 2005.
Office Action, U.S. Appl. No. 10/351,640, date mailed: Aug. 28, 2006.
Office Action, U.S. Appl. No. 10/351,640, date mailed: Jun. 5, 2007.
Office Action, U.S. Appl. No. 10/351,640, date mailed: Sep. 19, 2008.
Office Action, U.S. Appl. No. 10/612,665 date mailed: Jun. 20, 2006.
Office Action, U.S. Appl. No. 10/612,665 date mailed: Feb. 23, 2007.
Office Action, U.S. Appl. No. 10/612,665 date mailed: Dec. 31, 2007.
Office Action, U.S. Appl. No. 10/612,665 date mailed: Dec. 11, 2008.
Office Action, U.S. Appl. No. 11/880,275, date mailed: May 22, 2009.
Office Action, U.S. Appl. No. 11/881,759, date mailed: Dec. 12, 2007.
Office Action, U.S. Appl. No. 11/881,759, date mailed: Jul. 18, 2008.
Office Action, U.S. Appl. No. 11/881,759, date mailed: Sep. 24, 2008.
Office Action, U.S. Appl. No. 11/881,759, date mailed: Jul. 21, 2009.
Office Action, U.S. Appl. No. 11/893,294, date mailed: Jun. 16, 2008.
Office Action, U.S. Appl. No. 11/893,294, date mailed: Oct. 10, 2008.
Office Action, U.S. Appl. No. 11/893,294, date mailed: Feb. 2, 2009.
Office Action, U.S. Appl. No. 10/188,905, date mailed: Nov. 12, 2009.
Ghezzi et al., 2004, Erythropoietin as an antiapoptotic, tissue protective cytokine.
International Search Report for PCT/US00/10019, mailed Aug. 30, 2000.
Lindahl, 1980, "The contributions of erythropoietic and nonerythropoietic haem turnover to the early labelle peak of endogenous CO formation in man," Scand. J. Haematol. Apr. 24 (4): 271-80.
Salinska et al., 2005, "The role of excitotoxicity in neurodegeneration." Folia Neuropath., 43(4):322-339.
Segura-Aguilar et al., 2004, "Neurotoxins and neurotoxic species implicated in neurodegeneration." Neurotox. Res., 6(7,8):615-630.
Wang et al, 2005, "Kainic acid-mediated excitotoxicity as a model for neurodegeneration." Molec. Neurobiol., 31(1-3): 3-16.
Trist, 2000, "Excitatory amino acid agonists and antagonists: pharmacology and therapeutic applications." Pharmaceutica Acta Helvetiae, 74:221-229.
Written Opinion for PCT/US00/10019, mailed Aug. 16, 2001.
Office Action, U.S. Appl. No. 10/351,640, date mailed: Jul. 7, 2009.
Office Action, U.S. Appl. No. 11/893,294, date mailed: Aug. 13, 2009.
U.S. Appl. No. 12/863,915, filed Jul. 21, 2010, Cerami et al.
Albayrak S. et al, 1997, "Effect of transient focal ischemia on blood-brain barrier permeability in the rat: correlation to cell injury," Acta Neuropathol, 94:158-63.
Bezard et al., 1997, "A chronic MPTP model reproducing the slow evolution of Parkinson's disease: evolution of motor symptoms in the monkey," Brain Research, 766:107-112.
Boesch et al., 2008; "Neurological Effects of Recombinant Human Erythropoietin in Friedreich's Ataxia: A Clinical Pilot Trial," *Movement Disorders* 23:1940-1944.
Calafiore et al., 1996, "Left Anterior Descending Coronary Artery Grafting via Left Anterior Small Thoracotomy Without Cardiopulmonary Bypass," Ann Thorac Surg 61:1658-65.
Casadevall, N. et al, 1992, "High-dose recombinant human erythropoietin administered intravenously for the treatment of anaemia in myelodysplastic syndromes," Acta haematologica 87:25-7.
Duchen et al., 1968, "A hereditary motor neurone disease with progressive denervation of muscle is the mouse: the mutant 'wobbler'" *J. Neural. Neurosurg. Psychiat.* 31:535-542.
Goy, A. et al., 1993, "High doses of intravenous recombinant erythropoietin for the treatment of anaemia in myelodysplastic syndrome," British journal of haematology 84:232-7.
Grasso et al., 2006, "Amelioration of spinal cord compressive injury by pharmacological preconditioning with erythropoietin and a nonerythropoietic erythropoietin derivative," J. Neurosurg. Spine 4:310-318.
Ho L et al., 1998, "Induction of cyclooxygenase (COX)-2 but not COX-1 gene expression in apoptotic cell death," *Journal of Neuroimmunology* 89:142-149.
Kato, 1993, "In vivo kinetics after subcutaneous administration of recombinant human erythropoietin (EPOCH) (2): in rats kinetics at the time of a single application of 125I-EPOCH," Pharmacokinetics, Japan, vol. 8(4):481-92 (with English abstract).
McPherson et al., 2008, "Recent trends in erythropoietin-mediated neuroprotection," *Int J Dev Neurosci.* 26:103-11.
On-Line Medical Dictionary; website /cancerweb.ncl.ac.uk/omd. Published at the Dept. of Medical Oncology, University of Newcastle upon Type. Copyright 1997-2004. The CancerWEB Project.
Prehn et al., 1994, "Regulation of neuronal Bcl2 protein expression and calcium homeostasis by transforming growth factor type β confers wide-ranging protection on rat hippocampal neurons," *PNAS* 91:12599-12603.
Rogatcheva et al., "Characterization of the porcine ATM gene: Towards the generation of a novel non-murine animal model for Ataxia-Telangiectasia," Gene, 405:27-35, 2007.
Siren et al., 2009, "Therapeutic Potential of Erythropoietin and its Structural or Functional Variants in the Nervous System," Neurotherapeutics 6: 108-127.
Tan et al., 2005 "Model of cerebral palsy in the perinatal rabbit," Journal of Child Neurology, 20:972-9.

Tsuda et al., 1990, The Role of Carbohydrate in Recombinant Human Erythropoietin, *European Journal of Biochemistry* 188:405-411.

Vaziri, N.D. et al, 1995, "In vivo and in vitro pressor effects of erythropoietin in rats," The American journal of physiology 269:F838-45.

Wang et al, 2004, "The nonerythropoietic asialoerythropoietin protects against neonatal hypoxia-ischemia as potently as erythropoietin," J Neurochem 91:900-910.

Zorov et al., 2000, "Reactive oxygen species(ROS)-induced ROS release: A new phenomenon accompanying induction of the mitochondrial permeability transition in cardiac myocytes," *Journal of Experimental Medicine* 197:1001-1014.

U.S. Appl. No. 13/495,793, filed Jun. 13, 2012, Brines et al.

* cited by examiner

SEQUENCE LISTING

<160> NUMBER OF SEQ ID NOS: 5

<210> SEQ ID NO 1
<211> LENGTH: 5
<212> TYPE: PRT
<213> ORGANISM: Artificial Sequence
<220> FEATURE:
<223> OTHER INFORMATION: Functional Domain

<400> SEQUENCE: 1

Val Leu Gln Arg Tyr
 1               5

<210> SEQ ID NO 2
<211> LENGTH: 8
<212> TYPE: PRT
<213> ORGANISM: Artificial Sequence
<220> FEATURE:
<223> OTHER INFORMATION: Functional Domain

<400> SEQUENCE: 2

Thr Lys Val Asn Phe Tyr Ala Trp
 1               5

<210> SEQ ID NO 3
<211> LENGTH: 9
<212> TYPE: PRT
<213> ORGANISM: Artificial Sequence
<220> FEATURE:
<223> OTHER INFORMATION: Functional Domain

<400> SEQUENCE: 3

Ser Gly Leu Arg Ser Leu Thr Thr Leu
 1               5

<210> SEQ ID NO 4
<211> LENGTH: 6
<212> TYPE: PRT
<213> ORGANISM: Artificial Sequence
<220> FEATURE:
<223> OTHER INFORMATION: Functional Domain

<400> SEQUENCE: 4

Ser Asn Phe Leu Arg Gly
 1               5

<210> SEQ ID NO 5
<211> LENGTH: 193
<212> TYPE: PRT
<213> ORGANISM: Homo sapiens

<400> SEQUENCE: 5

Met Gly Val His Glu Cys Pro Ala Trp Leu Trp Leu Leu Leu Ser Leu
 1               5                  10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu

-continued

```
                    85                  90                  95
Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg
```

TISSUE PROTECTIVE CYTOKINES FOR THE PROTECTION, RESTORATION, AND ENHANCEMENT OF RESPONSIVE CELLS, TISSUES AND ORGANS

CROSS-REFERENCE TO RELATED APPLICATIONS

This application claims priority to U.S. patent application Ser. No. 10/188,905, filed Jul. 3, 2002, which is incorporated herein in its entirety.

BACKGROUND OF THE INVENTION

For many years, the only clear physiological role of erythropoietin had been its control of the production of red blood cells. Recently, several lines of evidence suggest that erythropoietin, as a member of the cytokine superfamily, performs other important physiologic functions which are mediated through interaction with the erythropoietin receptor (erythropoietin-R). These actions include mitogenesis, modulation of calcium influx into smooth muscle cells and neural cells, production of erythrocytes, hyperactivation of platelets, production of thrombocytes, and effects on intermediary metabolism. It is believed that erythropoietin provides compensatory responses that serve to improve hypoxic cellular microenvironment as well as modulate programmed cell death caused by metabolic stress. Although studies have established that erythropoietin injected intracranially protects neurons against hypoxic neuronal injury, intracranial administration is an impractical and unacceptable route of administration for therapeutic use, particularly for normal individuals. Furthermore, previous studies of anemic patients given erythropoietin have concluded that peripherally-administered erythropoietin is not transported into the brain (Marti et al., 1997, Kidney Int. 51:416-8; Juul et al., 1999, Pediatr. Res. 46:543-547; Buemi et al., 2000, Nephrol. Dial. Transplant. 15:422-433).

Various modified forms of erythropoietin have been described with activities directed towards improving the erythropoietic activity of the molecule, such as those with altered amino acids at the carboxy terminus described in U.S. Pat. No. 5,457,089 and in U.S. Pat. No. 4,835,260; erythropoietin isoforms with various numbers of sialic acid residues per molecule, such as described in U.S. Pat. No. 5,856,298; polypeptides described in U.S. Pat. No. 4,703,008; agonists described in U.S. Pat. No. 5,767,078; peptides which bind to the erythropoietin receptor as described in U.S. Pat. Nos. 5,773,569 and 5,830,851; and small-molecule minetics as described in U.S. Pat. No. 5,835,382.

The present invention relates to tissue protective cytokines generated by the chemical modification of erythropoietin and their uses for protecting, maintaining, enhancing, or restoring erythropoietin-responsive cells and associated cells, tissues and organs in situ as well as ex vivo, and to delivery of a tissue protective cytokine across an endothelial cell barrier for the purpose of protecting and enhancing erythropoietin-responsive cells and associated cells, tissues and organs distal to the vasculature, or to carry associated molecules across an endothelial cell barrier.

BRIEF SUMMARY OF THE INVENTION

In one aspect, the present invention is directed to the use of tissue protective cytokines, chemically-modified erythropoietins that lack one or more aspects of erythropoietin's affect on the bone marrow, for the preparation of pharmaceutical compositions for protecting, maintaining, enhancing, or restoring the function or viability of responsive mammalian cells and their associated cells, tissues and organs. In one particular aspect, the responsive mammalian cells and their associated cells, tissues or organs are distal to the vasculature by virtue of a tight endothelial cell barrier. In another particular aspect, the cells, tissues, organs or other bodily parts are isolated from a mammalian body, such as those intended for transplant or reattachment. By way of non-limiting examples, the responsive cell or tissue may be neuronal, retinal, muscle, heart, lung, liver, kidney, small intestine, adrenal cortex, adrenal medulla, capillary endothelial, testes, ovary, pancreas, bone, skin or endometrial cells or tissue. Further, non-limiting examples of responsive cells include photoreceptor (rods and cones), ganglion, bipolar, horizontal, amacrine, Mileller, myocardium, pace maker, sinoatrial node, sinoatrial node, sinus node, junction tissue, atrioventricular node, bundle of His, hepatocytes, stellate, Kupffer, mesangial, renal epithelial, tubular interstitial, goblet, intestinal gland (crypts), enteral, endocrine, glomemulosa, fasciculate, reticularis, chromaffin, pericyte, Leydig, Sertoli, sperm, Graffian follicle, primordial follicle, islets of Langerhans, α-cells, β-cells, γ-cells, F-cells, osteoprogenitor, osteoclasts, osteoblasts, endometrial stroma, endometrial, stem and endothelial cells. These examples of responsive cells are merely illustrative. In one aspect, the responsive cell or its associated cells, tissues, or organs are not excitable cells, tissues, or organs, or do not predominantly comprise excitable cells or tissues. In a particular embodiment, the mammalian cell, tissue or organ for which an aforementioned tissue protective cytokine is used are those that have expended or will expend a period of time under at least one condition adverse to the viability of the cell, tissue or organ. Such conditions include traumatic in-situ hypoxia or metabolic dysfunction, surgically-induced in-situ hypoxia or metabolic dysfunction, or in-situ toxin exposure; the latter may be associated with chemotherapy or radiation therapy. In one embodiment, the adverse conditions are a result of cardiopulmonary bypass (heart-lung machine), as is used for certain surgical procedures.

The tissue protective cytokines herein are useful for the therapeutic or prophylactic treatment of human diseases of the CNS or peripheral nervous system which have primarily neurological or psychiatric symptoms, as well as ophthalmic diseases, cardiovascular diseases, cardiopulmonary diseases, respiratory diseases, kidney, urinary and reproductive diseases, gastrointestinal diseases and endocrine and metabolic abnormalities, and inflammation.

The invention is also directed to pharmaceutical compositions comprising particular tissue protective cytokines for administration to a mammalian animal, preferably a human. Such pharmaceutical compositions may be formulated for oral, intranasal, or parenteral administration, or in the form of a perfusate solution for maintaining the viability of cells, tissues or organs ex vivo.

Tissue protective cytokines useful for the aforementioned purposes and pharmaceutical compositions include erythropoietins that have been altered by at least one modification as compared to a native erythropoietin, and preferably as compared to native human erythropoietin. The at least one modification may be a modification of at least one amino acid of the erythropoietin molecule, or a modification of at least one carbohydrate of the erythropoietin molecule. Of course, tissue protective cytokine molecules useful for the purposes herein may have a plurality of modifications compared to a native molecule, such as multiple modifications of the amino acid portion of the molecule, multiple modifications of the carbohydrate portion of the molecule, or at least one modification of the amino acid portion of the molecule and at least one modification of the carbohydrate portion of the molecule. The tissue protective cytokine molecule retains its ability of protecting, maintaining, enhancing or restoring the function or viability of responsive mammalian cells, yet one or more properties of the erythropoietin-molecule unrelated to the aforementioned, desirable feature may be absent as compared to the native molecule. In a preferred embodiment, the tissue protective cytokine lacks erythropoietin's affects on the bone marrow, ie., increased hematocrit (erythropoiesis), vasoconstriction (high blood pressure), increased blood pressure, hyperactivation of platelets, pro-coagulant activities, and increased production of thrombocytes. More preferably, the tissue protective cytokines lack erythropoiesis; most preferably the tissue protective cytokines are devoid of all of erythropoietin's effects on the bone marrow.

By way of example, the tissue protective cytokine of the invention may be asialoerythropoietin. In another example, the tissue protective cytokine of the invention may be erytlropoietin or asialoerythropoietin that has been reacted with one or more reagents that modify one or more amino groups of anmino acid residues of native erytlropoietin or asialoerythropoietin. In a preferred embodiment, the tissue protective cytokine is nonerythropoietic.

In one embodiment, the tissue protective cytokine is an erythropoietin that has no sialic acid moieties. In a preferred embodiment, the tissue protective cytokine is asialoerythropoietin, and most preferably, human asialoerythropoietin. In another embodiment, the tissue protective cytokine has 1, 2, 3, 4, 5, 6, 7, 8, 9, 10, 11, 12, or 13 sialic acid moieties. Such partially desialylated erythropoietins are referred to herein as hyposialoerythropoietins. They may be prepared by chemical or enzymatic modification of native erythropoietin, or may be obtained by expression in a system which either does not sialylate the molecule at all or only partially sialylates the erythropoietin. The asialoerythropoietin and hyposialoerythropoietin of the invention are embraced regardless of the means by which the molecules are prepared.

In another preferred embodiment, the tissue protective cytokine comprises at least one or more modified lysine residues or a modification of the N-terminal amino group of the erythropoietin molecule, such modifications as those resulting from reaction of the lysine epsilon amino group or the N-terminal amino group with an amino-group-modifying agent or agents. The modified lysine residue or modified N-terminal amino group fiurter may be chemically reduced. In one preferred embodiment, an erytihropoietin is biotinylated, carbamylated, succinylated or acetylated at one or more lysine groups or at the N-terminus. In another preferred embodiment, the lysine is reacted with an aldehyde or reducing sugar to form an imne, which optionally is then stabilized by chemical reduction such as by using sodium cyanoborohydride to form an N-alkylated lysine residue such as glucitolyl lysine, or which in the case of reducing sugars may be stabilized by Amadori or Heyns rearrangement to form an alpha-deoxy alpha-amino sugar such as alpha-deoxy-alpha-fractosyllysine. In another preferred embodiment, the lysine or N-terminal amino group is carbamylated (carbamoylated), such as by virtue of reaction with cyanate ion, alkyl-carbamylated, aryl-carbamylated, or aryl-thiocarbamylated with an alkyl-isocyanate, aryl-isocyanate, or aryl-isothiocyanate, respectively, or it may be acylated by a reactive alkylcarboxylic or arylcarboxylic acid derivative, such as by reaction with acetic anhydride, succinic anhydride or phthalic anhydride. At least one lysine group or the N-terminal amino group may also be trinitrophenyl modified by reaction with a trinitrobenzenesulfonic acid, or preferably with one of its salts. In another embodiment, lysine residues may be modified by reaction with a glyoxal, such as reaction with glyoxal, methylglyoxal or 3-deoxyglucosone to form the corresponding alpha-carboxyalkyl derivatives.

In another embodiment, a tissue protective cytokme can be generated by modifying at least one tyrosine residue of erytlropoietin by using an electrophilic reagent, such as but not limited to modification by nitration or iodination, to modify an aromatic ring position.

As noted above, a tissue protective agent useful for the purposes herein may have at least one of the aforementioned modifications, but may have more than one of the above modifications. By way of example of tissue protective cytokines with one modification to the amino acid portion of the molecule and optional modification to the carbohydrate portion of the molecule, a tissue protective cytokine is carbamylerythropoietin, carbamylasialoerythropoietin, carbamylhyposialoerythropoietin, acetylerythropoietin, acetylasialoerythropoietin, acetylhypoasialoerythropoietin, succinylerytbropoietin, succinylasialoerythropoietin, succinylhyposialoerythropoietin, biotinylerybropoietin, biotinylasialoerythropoietin, biotinylhypsialoerythropoietin, iodoerybhropoietin, iodoasialoerythropoietin, iodohyposialoerythropoietin, N-epsilon-carboxymethylerythropoietin, N-epsilon-carboxymethylerythropoietin, N-epsilon-carboxymethylhyposialoerythropoietin, and glucitolylerythropoietin, glucitolylasialoerythropoietin, glucitolylasialohypoerythropoietin. These compounds are merely exemplary of the modified erythropoietins of the invention. The foregoing trivial names are merely representative of the modifications of the native erytiropoietin molecule, and as hereinbefore described, the modification of the amino group may be on one or more epsilon amino groups of lysine residues, or the N-terminal amino group, or, in the instance of nitro- or iodo-modified erythropoietins, of one or more tyrosine residues. Any combination of the foregoing is embraced herein. The present invention also embraces compositions, including pharmaceutical compositions, comprising one or more of the aforementioned tissue protective cytokines. Any of such compositions may also include native erythropoietin.

In another aspect of the invention, a method is proviaeci tor the protecting, maintaining, enhancing or restoring the function or viability of responsive mammalian cells and their associated cells, tissues and organs, by administering an effective amount of any one or more of the aforementioned tissue protective cytokines. In one particular aspect of the method, the responsive mammalian cells and their associated cells, tissues or organs are distal to the vasculature by virtue of a tight endothelial cell barrier. In another particular aspect, the cells, tissues, organs or other bodily parts are isolated from a mammalian body, such as those intended for transplant or reattachment. By way of non-limiting examples, the responsive cell or tissue may be neuronal, retinal, muscle, heart, lung, liver, kidney, small intestine, adrenal cortex, adrenal medulla, capillary endothelial, testes, ovary, pancreas, skin, bones, or endometrial cells or tissue. These examples of responsive cells are merely illustrative. In a particular embodiment, the responsive cell or its associated cells, tissues, or organs are not excitable cells, tissues, or organs, or do not predominantly comprise excitable cells or tissues. In another particular embodiment, the mammalian cell, tissue or organ for which an aforementioned tissue protective cytokine may be administered are those that have expended or will expend a period of time under at least one condition adverse to the viability of the cell, tissue or organ. Such conditions may include traumatic in-situ hypoxia or metabolic dysfunction, surgically-induced in-situ hypoxia or metabolic dysfunction, or in-situ toxin exposure; the latter may be associated with chemotherapy or radiation therapy. In one embodiment, the invention protects against the adverse conditions resulting from cardiopulmonary bypass.

In another aspect of the invention, any of the foregoing tissue protective cytokines can be used in the preparation of a pharmaceutical composition for ex-vivo treatment of cells, tissues and organs for the purpose of protecting, maintaining, enhancing, or restoring the fiuntion or viability of responsive mammalian cells and their associated cells, tissues and organs. Such ex-vivo treatment is useful, for example, for the preservation of cells, tissues or organs for transplant, whether autotransplant or xenotransplant. The cells, tissue or organ may be bathed in a solution comprising tissue protective cytokines, or the perfusate instilled into the organ through the vasculature or other means, to maintain cellular functioning during the period wherein the cells, tissue or organ is not integrated with the vasculature of the donor or recipient. Administration of the perfasate may be made to a donor prior to organ harvesting, as well as to the harvested organ and to the recipient. Moreover, the aforementioned use of any tissue protective cytokine is useful whenever a cell, tissue or organ is isolated from the vasculature of the individual and thus essentially existing ex vivo for a period of time, the term isolated referring to restricting or clamping the vasculature of or to the cell, tissue, organ or bodily part, such as may be performed during surgery, including, in particular, cardiopulmonary bypass surgery, bypassing the vasculature of the cell, tissue, organ or bodily part; removing the cell, tissue, organ or bodily part from the mammalian body, such may be done in advance of xenotransplantation or prior to and during autotransplantation; or traumatic amputation of a cell, tissue, organ or bodily part. Thus, this aspect of the invention pertains both to the perfusion with a tissue protective cytokine in situ and ex vivo. Ex vivo, the erythropoietin may be provided in a cell, tissue or organ preservation solution. For either aspect, the exposing may be by way of continuous perfusion, pulsatile perfusion, infusion, bathing, injection, or catheterization.

In yet a further aspect, the invention is directed to a method for protecting, maintaining, enhancing, or restoring the viability of a mammalian cell, tissue, organ or bodily part which includes a responsive cell or tissue, in which the cell, tissue, organ or bodily part is isolated from the mammalian body. The method includes at least exposing the isolated manmmalian cell, tissue, organ or bodily part to an amount of a tissue protective cytoldne as mentioned above for a duration which is effective to protect, maintain, enhance, or restore the aforesaid viability. In non-limiting examples, isolated refers to restricting or clamping the vasculature of or to the cell, tissue, organ or bodily part, such as may be performed during surgery, in particular, cardiopulmonary bypass surgery; bypassing the vasculature of the cell, tissue, organ or bodily part; removing the cell, tissue, organ or bodily part from the mammalian body, such may be done in advance of xenotrsplantation or prior to and during autotransplantation; or traumatic amputation of a cell, tissue, organ or bodily part. Thus, this aspect of the invention pertains both to the perfusion with a tissue protective cytokine in situ and ex vivo. Ex vivo, the tissue protective cytokine maybe provided in a cell, tissue or organ preservation solution. For either aspect, the exposing may be by way of continuous perfusion, pulsatile perfusion, infusion, bathing, injection, or catheterization.

By way of non-limiting examples, the aforementioned ex-vivo responsive cell or tissue may be or comprise neuronal, retinal, muscle, heart, lung, liver, kidney, small intestine, adrenal cortex, adrenal medulla, capillary endothelial, testes, ovary, pancreas, skin, bone, bone marrow, umbilical chord blood or endometrial cells or tissue. These examples of responsive cells are merely illustrative.

All of the foregoing methods and uses are preferably applicable to human beings, but are useful as well for any mammal, such as but not limited to companion animals, domesticated animals, livestock and zoo animals. Routes of administration of the aforementioned pharmaceutical compositions include oral, intravenous, intranasal, topical, intraluminal, inhalation or parenteral administration, the latter including intravenous, intraarterial, subcutaneous, intramnuscular, intraperitoneal, submucosal or intradermal. For ex-vivo use, a perfusate or bath solution is preferred. This includes perfusing an isolated portion of the vasculature in situ.

In yet another aspect of the invention, any of the atorementioned tissue protective cytokines are useful in preparing a pharmaceutical composition for restoring a dysfunctional cell, tissue or organ when administered after the onset of the disease or condition responsible for the dysfumction. By way of non-limiting example, administration of a pharmaceutical composition comprising tissue protective cytokines restores cognitive function in animals previously having brain trauma, even when administered long after (e.g., three days, five days, a week, a month, or longer) the trauma has subsided.

In yet another embodiment, the invention provides methods for the use of the aforementioned tissue protective cytokine for restoring a dysfunctional cell, tissue or organ when administered after the onset of the disease or condition responsible for the dysfunction. By way of non-limiting example, methods for administration of a pharmaceutical composition comprising a tissue protective cytoldne restores cognitive function in animals previously having brain trauma, even when administered long after (e.g., three days, five days, a week, a month, or longer) the trauma has subsided. Tissue protective cytokines useful for such methods include any of the particular aforementioned modified erythropoietins In still yet a further aspect of the present invention, methods are provided for facilitating the transcytosis of a molecule across an endothelial cell barrier in a mammal by administration of a composition of a molecule in association with a tissue protective cytokine as described hereinabove. The association between the molecule to be transported and the tissue protective cytokine may be, for example, a labile covalent bond, a stable covalent bond, or a noncovalent association with a binding site for the molecule. Endothelial cell barriers may be the blood-brain barrier, the blood-eye barrier, the blood-testes barrier, the blood-ovary barrier and the blood-placenta barrier. Suitable molecules for traport by the method of the present invention include hormones such as growth hormone, nerve growth factor (NGF), brain-derived neurotrophic factor (BDN), ciliary neurotrophic factor (CNTF), basic Fibroblast growth factor (bFGF), transforming growth factor $\beta 1$ (TGF$\beta 1$), transforming growth factor $\beta 2$ (TGF$\beta 2$), transforming growth factor $\beta 3$ (TGF$\beta 3$), interleukin 1, interlekn 2, interleukin 3, and interleukin 6, AZT, antibodies against tumor necrosis factor, antiviral, and immunosuppressive agents such as cyclosporin. Additionally, dyes or markers may be attached to erythropoietin or one of the tissue protective cytokines of the present invention in order to visualize cells, tissues, or organs within the brain and other barriered organs for diagnostic purposes.

It is a further aspect of the present invention to provide a composition for facilitating the transcytosis of a molecule across an endothelial cell barrier in a mammal, the composition comprising the molecule in association with a tissue protective cytokine as mentioned hereinabove. The association may be, for example, a labile covalent bond, a stable covalent bond, or a noncovalent association with a binding site for the molecule. Endothelial cell barriers may be the blood-brain barrier, the blood-eye barrier, the blood-testes barrier, the blood-ovary barrier and. the blood-placenta barrier. Suitable molecules for transport by the method of the present invention include hormones such as growth hormone, nerve growth factor (NGF), brain-derived neurotrophic factor (BDNF), ciliary neurotrophic factor (CNTF), basic fibroblast growth factor (bFGF), transforming growth factor β1 (TGFβ1), transforming growth factor β2 (TGFβ2), transforming growth factor β3 (TGFβ3), interleukin 1, interleukin 2, interleukin 3, and interleulin 6, AZT, antibodies against tumor necrosis factor, antiviral, and immunosuppressive agents such as cyclosporit Additionally, dyes or markers may be attached to erythropoietin or one of the tissue protective cytolines of the present invention in order to visualize cells, tissues, or organs within the brain and other barriered organs for diagnostic purposes.

In a still further aspect of the present invention, any of the aforementioned tissue protective cytokines is useful in preparing a pharmaceutical composition for facilitating the transcytosis of a molecule across an endothelial cell barrier in a mammal. The association may be, for example, a labile covalent bond, a stable covalent bond, or a noncovalent association with a binding site for the molecule. Endothelial cell barriers may be the blood-brain barrier, the blood-eye barrier, the blood-testes barrier, the blood-ovary barrier and the blood-placenta barrier. Suitable molecules for transport by the method of the present invention include hormones, such as growth hormone, antibiotics, antivirals, dyes, markers, and anticancer agents, to name but a few non-limiting examples.

In one embodiment, the pharmaceutical composition of the invention comprises a therapeutically effective amount of a tissue protective cytokine, at least one anti-inflammatory agent, and a pharmaceutically acceptable carrier. In a related embodiment, the anti-inflammatory agent is selected from the group consisting of corticosteroids, glucocorticoids, steroids, non-steriodal anti-inflammatory drugs, beta-agonists, anticholinergic agents, methyl xanthines, gold injections, sulphasalazine, penicillamine, anti-angiogenic agents, dapsone, psoralens, anti-malarial agents, anti-viral agents, and antibiotics.

In one embodiment, the invention provides for a pharmaceutical composition of the invention comprises a therapeutically effective amount of a tissue protective cytokine, at least one anti-inflammatory agent and/or at least one immunomodulatory agent, and a pharmaceutically acceptable carrier, with the proviso that the anti-inflammatory agent or immunomodulatory agent is not an αMSH or an anti-TNF. In a related embodiment, the anti-inflammatory agent or immunomodulatory agent is not an antibody.

In one embodiment, the invention provides for a pharmaceutical composition of the invention consists essentially of a therapeutically effective amount of a tissue protective cytokine and comprises at least one anti-inflammatory agent and/or at least one immunomodulatory agent, and a pharmaceutically acceptable-ratrer.

The invention provides for a pharmaceutical composition that comprises a therapeutically effective amount of a tissue protective cytokine, at least one immunomodulatory agent, and a pharmaceutically acceptable carrier. In a related embodiment, the anti-inflammatory agent is selected from the group consisting of methothrexate, leflunomide, cyclophosphamide, cytoxan, Immuran, cyclosporine A, minocycline, azathioprine, antibiotics, methylprednisolone, corticosteroids, steroids, mycophenolate mofetil, rapamycin, mizoribine, deoxyspergualin, brequinar, malononitriloamindes, T cell receptor modulators, and cytokine receptor modulators.

The invention also provides for a pharmaceutical composition as described herein above, wherein said tissue protective cytokine is selected from the group consisting of i) an erythropoietin that lacks sialic acid moieties; ii) an erythropoietin that lacks N-linked or lacks O-linked carbohydrates; iii) an erythropoietin having a reduced carbohydrate content by treatment of native erythropoietin with at least one glycosidase; iv) an erythropoietin having at least one or more oxidized carbohydrates; v) an erythropoietin comprising at least one or more oxidized carbohydrates which is chemically reduced; vi) an erythropoietin comprising at least one or more modified arginine residues; vii) an erythropoietin comprising at least one or more modified lysine residues or a modification of the N-terminal amino group of the erythropoietin molecule; viii) an erythropoietin comprising at least a modified tyrosine residue; ix) an erythropoietin comprising at least a modified aspartic acid or a glutamic acid residue; x) an erythropoietin comprising at least a modified tryptophan residue; xi) an erythropoietin having at least one amino group removed; xii) an erythropoietin comprising at least an opening of at least one of the cystine linkages in the erythropoietin molecule; and xiii) a truncated erytbropoietin.

In one embodiment, a method for treating inflammation in a mammal comprising responsive cells, tissues, and/or organs, comprises administering to a mammal a pharmaceutical composition comprising a therapeutically effective amount of a tissue protective cytokine and a pharmaceutically acceptable carrier. In a related embodiment, the tissue protective cytokine lacks at least one activity selected from the group consisting of increasing hematocrit, vasoconstriction, hyperactivating platelets, pro-coagulant activity and increasing production of thrombocytes.

In another embodiment, a method treating inflammation in a mammal comprising responsive cells, tissues, and/or organs, comprises administering to a mammal in need thereof a pharmaceutical composition comprising a prophylactically or therapeutically effective amount of a tissue protective cytokine and a pharmaceutically acceptable carrier, and administering to the mammal a prophylactically or therapeutically effective amount of one or more anti-inflammatory agents or immunomodulatory agents. In one embodiments, the anti-inflammatory agent is selected from the group consisting of a corticosteroid, a glucocorticoid, a steroid, a non-steriodal anti-inflammatory drug, a beta-agonist, a anticholinergic agent, a methyl xanthine, gold injection, a sulphasalazine, penicillamine, a anti-angiogenic agent, dapsone, psoralen, a anti-malarial agent, a anti-viral agent, and an antibiotic.

In one embodiment, the invention provides for a method treating inflammation in a mammal comprising responsive cells, tissues, and/or organs, comprises administering to a mammal in need thereof a pharmaceutical composition comprising a prophylactically or therapeutically effective amount of a tissue protective cytokine and a pharmaceutically acceptable carrier, and administering to the mammal a prophylactically or therapeutically effective amount of one or more anti-inflammatory agents or immunomodulatory agents, with the proviso that the anti-inflammatory agent or immunomodulatory agent is not an αMSH or an anti-TNF. In a related embodiment, the anti-inflammatory agent or ummunomodulatory agent is not an antibody.

In another embodiment, the immunomodulatory agent is selected from the group consisting of a proteinaceous agent, a peptide mimetic, an antibody, a nucleic acid molecule, a small molecule, an organic compound, an inorganic compound, methothrexate, leflunomide, cyclophosphamide, cytoxan, Immuran, cyclosporine A, minocycline, azathioprine, an antibiotic, methylprednisolone (MP), a corticosteroid, a steroid, mycophenolate mofetil, rapamycin, mizoribine, deoxyspergualin, brequinar, a malononitriloaminde, a T cell receptor modulator, and a cytokine receptor modulator.

The invention provides for a method as described herein above, wherein said tissue protective cytokine is i) an erythropoietin that lacks sialic acid moieties; ii) an erythropoietin that lacks N-linked or lacks O-linked carbohydrates; iii) an erytliropoietin having a reduced carbohydrate content by treatment of native erythropoietin with at least one glycosidase; iv) an erythropoietin having at least one or more oxidized carbohydrates; v) an erythropoietin comprising at least one or more oxidized carbohydrates which is chemically reduced; vi) an erythropoietin comprising at least one or more modified arginine residues; vii) an erythropoietin comprising at least one or more modified lysine residues or a modification of the N-terminal amino group of the erythropoietin molecule; viii) an erythropoietin comprising at least a modified tyrosine residue; ix) an erythropoietin comprising at least a modified aspartic acid or a glutamic acid residue; x) an erythropoietin comprising at least a modified trrptophan residue; xi) an erythropoietin having at least one amino group removed; xii) an erythropoietin comprising at least an opening of at least one of the cystine linkages in the erythropoietin molecule; and xiii) a truncated erythropoietin.

In one embodiment, the tissue protective cytokine of the compositions and methods described herein above is asialoerythropoietin or phenylglyoxal-erythropoietin. In another embodiment, the tissue protective cytokine is capable of traversing an endothelial cell barrier. The endothelial cell barrier can be selected from the group consisting of blood-brain barrier, blood-eye barrier, blood-testis barrier, blood-ovary barrier, and blood-uterus barrier.

In one embodiment, the responsive cells, tissues, and/or organs in the mammal which are the target of the pharmaceutical compositions and methods of the invention, are selected from the group consisting of neuronal cells, muscle cells, heart, lung, liver, kidney, small intestine, adrenal cortex, adrenal medulla, capillary cells, endothelial cells, testes, ovary, endometrial cells, and stem cells. In another embodiment, the responsive mammalian cells flrter comprise cells selected from the group consisting of photoreceptor cells, ganglion cells, bipolar cells, horizontal cells, amacrine cells, Muieller cells, myocardium cells, pace maker cells, sinoatrial node cells, sinoatrial node cells, sinus node cells, atrioventricular node cells, bundle of His cells, hepatocyte cells, stellate cells, Kupffer cells, mesangial cells, goblet cells, intestinal gland cells, enteral endocrine cells, glomerulosa cells, fasciculate cells reticularis cells, chromaffin cells, pericyte cells, Leydig cells, Sertoli cells, sperm cells, Graffian follicle cells, primordial follicle cells, endometrial stroma cells, and endometrial cells.

The invention also provides for a pharmaceutical composition and methods for treating inflammation in a mammal as described herein above, wherein said tissue protective cytokine is asialoerythropoietin. In preferred embodiments, the asialoerythropoietin is human asialoerythropoietin. The tissue protective cytokine is preferably an erythropoietin with no N-linked carbohydrates. The tissue protective cytokine is preferably an erythropoietin with no O-linked carbohydrates. In one embodiment, the tissue protective cytokine is an erythropoietin treated with at least one glycosidase. In another embodiment, the tissue protective cytokine is periodate-oxidized erythropoietin. The periodate-oxidizet erytrropoletm is preferably chemically reduced with sodium cyanoborohydride. In one embodiment, the tissue protective cytokine is an erythropoietin comprising a R-glyoxal moiety on the one or more arginine residues, wherein R is aryl or alkyl moiety. The erythropoietin is preferably phenylglyoxal-erythropoietin. In another embodiment, the tissue protective cytokine is an erythropoietin in which at least one arginine residue is modified by reaction with a vicinal diketone selected from the group consisting of 2,3-butanedione and cyclohexanedione. In yet another embodiment, the tissue protective cytoline of the invention is an erythropoietin in which at least one arginine residue is reacted with 3-deoxyglucosone. In still another embodiment, the tissue protective cytokine is an erythropoietin molecule comprising at least one biotinylated lysine or N-terminal amino group. The erythropoietin molecule can be a biotinylated erythropoietin.

The invention also provides for a pharmaceutical composition and methods for treating inflammation in a mammal comprising a tissue protective cytokine that is a glucitolyl lysine erytiropoietin or a fructosyl lysine erytbropoietin.

In one embodiment, the tissue protective cytokine of the pharmaceutical compositions and methods of the invention is an erythropoietin having at least one carbamylated lysine residue. In another embodiment, the carbamylated erythropoietin is selected from the group consisting of alpha-N-carbamoylerythropoietin; N-epsilon-carbamoylerythropoietin; alpha-N-carbamoyl, N-epsilon-carbamoylerythropoietin; alpha-N-carbamoylasialoerythropoietin; N-epsilon-carbamoylasialoerylhropoietin; alpha-N-carbamoyl, N-epsilon-carbamoylasialoerythropoietin; alpha-N-carbamoylhyposialoerythropoietin; N-epsilon-carbamoylhyposialoerythropoietin; and alpha-N-carbamoyl, N-epsilon-carbamoylhyposialoerythropoietin.

In one embodiment, the tissue protective cytokine of the pharmaceutical compositions and methods of the invention is an erythropoietin in which at least one lysine residue is acylated. In another embodiment, a lysine residue of said erythropoietin is acetylated. In yet another embodiment, the acetylated erythropoietin is selected from the group consisting of alpha-N-acetylerythropoietin; N-epsilon-acetylerythropoietin; alpha-N-acetyl, N-epsilon-acetylerythropoietin; alpha-N-acetylasialoerythropoietin; N-epsilon-acetylasialoerythropoietin; alpha-N-acetyl, N-epsilon-acetylasialoerythropoietin; alpha-N-acetylhyposialoerythropoietin; N-epsilon-acetylhyposialoerythropoietin; and alpha-N-acetyl, N-epsilon-acetylhyposialoerythropoietin.

In one embodiment, the tissue protective cytoline of the pharmaceutical compositions and methods of the invention is an erythropoietin comprising a succinylated lysine residue. In one embodiment, the erythropoietin is selected from the group consisting of alpha-N-succinylerythropoietin; N-epsilon-succinylerythropoietin; alpha-N-succinyl, N-epsilon-succinylerythropoietin; alpha-N-succinylasialoerythropoietin; N-epsilon-succinylasialoerythropoietin; alpha-N-succinyl, N-epsilon-succinylasialoerythropoietin; alpha-N-succinylhyposialoerythropoietin; N-epsilon-succinylhyposialoerythropoietin; and alpha-N-succinyl, N-epsilon-succinylhyposialoerythropoietin.

In one embodiment, the tissue protective cytokine of the pharmaceutical compositions and methods of the invention is an erythropoietin with at least one lysine residue modified by a 2,4,6-trinitrobenzenesulfonic acid salt. In one aspect of the invention, the salt is 2,4,6-trinitrobenzenesulfonate sodium.

In another embodiment, the tissue protective cytokine of the pharmaceutical compositions and methods of the invention is an erythropoietin in which at least one tyrosine residue is nitrated and/or iodinated.

In yet another embodiment, the tissue protective cytokine of the pharmaceutical compositions and methods of the invention is an erythropoietin in which an aspartic acid and/or glutamic acid residue is reacted with a carbodiimide followed by reaction with an amine. In one aspect of the invention the amine is glycinamide.

In one embodiment, the tissue protective cytokine of the pharmaceutical compositions and methods of the invention described herein above are used in treating inflammation resulting from a disease condition or trauma In one embodiment, the trauma is selected from the group consisting of angitis, chronic bronchitis, pancreatitis, osteomylitis, rheumatoid arthritis, glomerulonephritis, optic neuritis, temporal arteritis, encephalitis, meningitis, transverse myelitis, dermatomyositis, polymyositis, necrotizing fascihtis, hepatitis, and necrotizing enterocolitis.

In one embodiment, the tissue protective cytokine of the pharmaceutical compositions and methods of the invention inhibits inflammation resulting from cytokines produced by glial cells. In another embodiment, the inflammation is triggered by apoptosis.

According to one aspect of the invention, a tissue protective cytokine can be used for the preparation of a pharmaceutical composition for treating inflammation in a mammal comprising responsive cells, tissues, and/or organs. According to certain aspects the tissue protective cytokine lacks at least one activity selected from the group consisting of increasing hematocrit, vasoconstriction, hyperactivating platelets, procoagulant activity and increasing production of thrombocytes. In one embodiment, the inflammation results from a disease condition or trauma In another embodiment, the trauma is caused by a seizure disorder, multiple sclerosis, stroke, hypotension, cardiac arrest, ischemia, myocardial infarction, age-related loss of cognitive function, radiation damage, cerebral palsy, neurodegenerative disease, Alzheimer's disease, Parkinson's disease, Leigh disease, AIDS dementia, memory loss, amyotrophic lateral sclerosis, alcoholism, mood disorder, anxiety disorder, attention deficit disorder, autism, Creutzfeld-Jakob disease, brain trauma, spinal cord trauma, brain ischemia, spinal cord ischemia, heart-lung bypass, chronic heart failure, macular degeneration, diabetic neuropathy, diabetic retinopathy, glaucoma, retinal ischemia, or retinal trauma.

The invention provides for the use of a tissue protective cytokine for the preparation of a pharmaceutical composition for treating inflammation in a mammal comprising responsive cells, tissues, and/or organs, wherein the pharmaceutical composition comprises a therapeutically effective amount of a tissue protective cytokine; at least one anti-inflammatory agent or immunomodulatory agent; and a pharmaceutically acceptable carrier. In one embodiment, the tissue protective cytokine is i) an erythropoietin that lacks sialic acid moieties; ii) an erytlhropoietin that lacks N-linked or lacks O-linked carbohydrates; iii) an erythropoietin having a reduced carbohydrate content by treatment of native erythropoietin with at least one glycosidase; iv) an erythropoietin having at least one or more oxidized carbohydrates; v) an erythropoietin comprising at least one or more oxidized carbohydrates which is chemically reduced; vi) an erythropoietin comprising at least one or more modified arginine residues; vii) an erythropoietin comprising at least one or more modified lysine residues or a modification of the N-terminal amino group of the erythropoietin molecule; viii) an erythropoietin comprising at least a modified tyrosine residue; ix) an erythropoietin comprising at least a modified aspartic acid or a glutamic acid residue; x) an erythropoietin comprising at least a modified tryptophan residue; xi) an erythropoietin having at least one amino group removed; xii) an erythropoietin comprising at least an opening of at least one of the cystine linkages in the erythropoietin molecule; and xiii) a truncated erythropoietin.

These and other aspects of the present invention will be better appreciated by reference to the following Figures and Detailed Description.

DETAILED DESCRIPTION OF THE INVENTION

Figure 1:
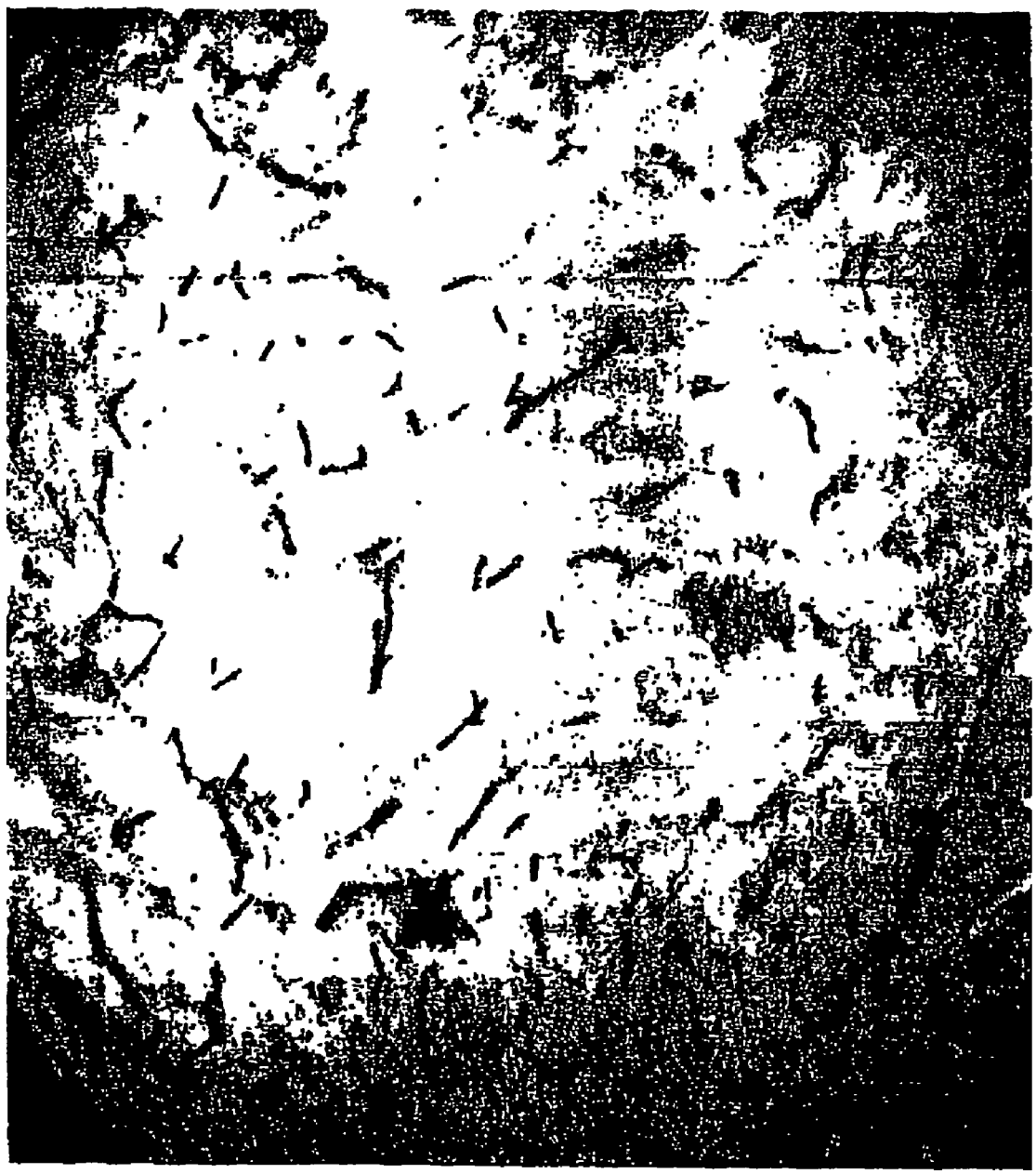
FIG. 1 shows the distribution of erythropoietin receptor in normal human brain, in thin sections stained with an anti-erythropoietin antibody.

The methods of the invention provide for the local or systemic protection or enhancement of cells, tissues and organs within a mammalian body, under a wide variety of normal and adverse conditions, or protection of those which are destined for relocation to another mammalian body. In addition, restoration or regeneration of dysfunction is also provided. As mentioned above, the ability of an erythropoietin to cross a tight endothelial cell barrier and exert its positive effects on responsive cells (as well as other types of cells) distal to the vasculature offers the potential to prevent as well as treat a wide variety of conditions and diseases which otherwise cause significant cellular and tissue damage in an animal, including human, and moreover, permit success of heretofore unattemptable surgical procedures for which risk traditionally outweighed the benefits.

Erythropoietin is a glycoprotein hormone which in humans has a molecular weight of about 34 kDa. The mature protein comprises 165 amino acids, and the glycosyl residues comprise about 40% of the weight of the molecule. Erythropoietin can be obtained commercially, for example, under the trademarks of PROCRIT, available from Ortho Biotech Inc., Raritan, N.J., and EPOGEN, available from Amgen, Inc., Thousand Oaks, Calif. Furthermore, a variety of host systems may be used for expression and production of recombinant erythropoietin, including, but not limited to, bacteria, yeast, insect, plant, and mammalian, including human, cell systems. For example, recombinant erythropoietin produced in bacteria, which do not glycosylate or sialate the product, could be used to produce non-glycosylated forms of erythropoietin. Alternatively, recombinant erythropoietin can be produced in other systems that do glycosylate, e.g., plants, including human cells. The forms of erythropoietin useful in the practice of the present invention encompass chemical modifications and/or expression-system-mediated glycosylation modifications of naturally-occurring, synthetic and recombinant forms of human and other mammalian erythropoietins.

"Responsive cell" refers to a mammalian cell whose function or viability may be maintained, promoted, enhanced, regenerated, or in any other way benefited, by exposure to an erythropoietin. Non-limiting examples of such cells include neuronal, retinal, muscle, heart, lung, liver, kidney, small intestine, adrenal cortex, adrenal medulla, capillary endothelial, testes, ovary, pancreas, skin, bone and endometrial cells. In particular, responsive cells include, without llmitation, neuronal cells; retinal cells: photoreceptor (rods and cones), ganglion, bipolar, horizontal, amacrine, and Muieller cells; muscle cells; heart cells: myocardium, pace maker, sinoatrial node, sinoatrial node, sinus node, and junction tissue cells (atrioventricular node and bundle of his); lung cells; liver cells: hepatocytes, stellate, and Kupffer cells; kidney cells: mesangial, renal epithelial, and tubular interstitial cells; small intestine cells: goblet, intestinal gland (crypts) and enteral endocrine cells; adrenal cortex cells: glomerulosa, fasciculate, and reticularis cells; adrenal medulla cells: chromaffin cells; capillary cells: pericyte cells; testes cells: Leydig, Sertoli, and sperm cells and their precursors; ovary cells: Graffian follicle and primordial follcle cells; endometrial cells: endometrial stroma and endometrial cells; pancreas cell: islet of Langerhans, α-cells, β-cells, γ-cells, and F-cells; skin cells; bone cells: osteoprogenitor, osteoclast and osteoblast cells; as well as the stem and endothelial cells present in the above listed organs. Moreover, such responsive cells and the benefits provided thereto by an erythropoietin may be extended to provide protection or enhancement indirectly to other cells that are not directly responsive, or of tissues or organs which contain such non-responsive cells. These other cells, or tissues or organs which benefit indirectly from the enhancement of responsive cells present as part of the cells, tissue or organ as "associated" cells, tissues and organs. Thus, benefits of an erytlropoietin as described herein may be provided as a result of the presence of a small number or proportion of responsive cells in a tissue or organ, for example, excitable or neuronal tissue present in such tissue, or the Leydig cells of the testis, which makes testosterone. In one aspect, the responsive cell or its associated cells, tissues; or organs are not excitable cells, tissues, or organs, or do not predominantly comprise excitable cells or tissues.

The duration and degree of purposeful adverse conditions induced for ultimate benefit, such as high-dose chemotherapy, radiation therapy, prolonged ex-vivo transplant survival, and prolonged periods of surgically-induced ischemia, may be carried out by taking advantage of the invention herein. However, the invention is not so limited, but includes as one aspect, methods or compositions wherein the target responsive cells are distal to the vasculature by virtue of an endothelial-cell barrier or endothelial tight junctions. In general, the invention is directed to any responsive cells and associated cells, tissues and organs which may benefit from exposure to erythropoietin. Furthermore, cellular, tissue or organ dysfunction may be restored or regenerated after an acute adverse event (such as trauma) by exposure to erythropoietin.

The invention is directed generally to the use of erythropoietin for the preparation of pharmaceutical compositions for the aforementioned purposes in which cellular function is maintained, promoted, enhanced, regenerated, or in any other way benefited. The invention is also directed to methods for maint g, enhancing, promoting, or regenerating cellular fulnction by administering to a mammal an effective amount of erythropoietin as described herein. The invention is further directed to methods for maintaining, promoting, enhancing, or regenerating cellular function ex vivo by exposing cells, a tissue or organ to erythropoietin. The invention is also directed to a perfusate composition comprising erythropoietin for use in organ or tissue preservation.

The various methods of the invention utilize a pharmaceutical composition which at least includes erythropoietin at an effective amount for the particular route and duration of exposure to exert positive effects or benefits on responsive cells within or removed from a mammalian body. Where the target cell, tissues or organs of the intended therapy require erythropoietin to cross an endothelial cell barrier, the pharmaceutical composition includes erythropoietin at a concentration which is capable, after crossing the endothelial cell barrier, of exerting its desirable effects upon the responsive cells. Molecules capable of interacting with the erythropoietin receptor and modulating the activity of the receptor, herein referred to as erytlropoietin or erytlropoictin receptor activity modulators, are useful in the context of the present invention. These molecules may be, for example, naturally-occurring, synthetic, or recombinant forms of erythropoietin molecules, as described above, or other molecules which may not necessarily resemble erythropoietin in any manner, except to modulate erythropoietin responsive cell activity, as described herein.

In addition to the above identified tissue protective attributes, erythropoietin is more commonly associated with its effects on the bone marrow, i.e., increased hematocrit (erythropoiesis), vasoconstriction (high blood pressure), hyperactivation of platelets, pro-coagulant activity, and increased production of thrombocytes. However, these effects on the bone marrow may pose a risk in the chronic and acute administration of erythropoietin to treat the cellular, tissue, or organ dysfiuctions discussed above. Therefore, the invention is directed generally to the use of tissue protective cytokines that consist of chemically modified erythropoietin, which preferably lack one or more of erythropoietin's effects on the bone marrow. More preferably, the tissue protective cytokines lack erythropoiesis; most preferably the tissue protective cytokines are devoid of all of erythropoietin's effects on the bone marrow. In other embodiments, the tissue protective cytokine lacks any two of the aforesaid effects, or any three of the aforesaid effects.

Furthermore, the tissue protective cytokines desirable for the uses described herein may be generated by guanidination, amidination, carbamylation (carbamoylation), trinitrophenylation, acetylation, succinylation, nitration, or modification of arginine, lysine, tyrosine, typtophan, or cysteine residues or carboxyl groups, among other procedures, such as limited proteolysis, removal of amino groups, and/or mutational substitution of arginine, lysine, tyrosine, tryptophan, or cysteine residues of erythropoietin by molecular biological techniques. Preferably, these chemical modifications affect the four recognized receptor regions—VLQRY (SEQ ID NO:1), TVNFYAW (SEQ ID NO:2), SGIRSLTTL (SEQ ID NO:3), or SNFLRG (SEQ ID NO:4). More preferably, these receptor regions, which are basic in nature, are modified by chemical modification of the basic amino acids, arginine and lysine, within these regions. Additionally, the areas of the molecule surrounding these receptor regions may be chemically modified as well to affect the kinetics or receptor binding properties of the molecule. This produces tissue protective cytokines which maintain an adequate level of activities for specific organs and tissues but not for others, such as erythrocytes (e.g., Satake et al; 1990, *Biochim. Biophys. Acta* 1038:125-9;incorporated herein by reference in its entirety, in which in vivo biological activity was determined by the polycythemic mouse bioassay). One non-limiting example as described hereinbelow is the modification or erthropoieting arginine residues by reaction with a glyoxal such as phenylglyoxal (according to the protocol of Takahashi, 1977, *J. Biochem.* 81:395-402). As will be seen below, such a tissue protective cytokine molecule fully retains its neurotrophic effect. Such tissue protective cytokine molecules are fully embraced for the various uses and compositions described herein.

The activity (in units) of erythropoietin and erythropoietin-like molecules is traditionally defined based on its effectiveness in stimulating red cell production in rodent models (and as derived by international standards of erythropoietin). One unit (U) of regular erythropoietin (MW of ~34,000) is about 8 ng of protein (1 mg protein is approximately 125,000 U). However, as the effect on erytbropoiesis is incidental to the desired activities herein and may not necessarily be a detectable property of certain of the tissue protective cytokines of the invention, a definition of activity of certain tissue protective cytokines of the invention based on erythropoietic activity is inappropriate. Thus, as used herein, the activity unit of erythropoietin or the tissue protective cytokines is defined as the amount of protein required to elicit the same activity in neural or other responsive cellular systems as is elicited by WHO international standard erytiropoietin in the same system. The skilled artisan will readily determine the units of a non-erythropoietic erythropoietin or related tissue protective cytokine molecule following the guidance herein.

Further to the above-mentioned tissue protective cytokines, the following discussion expands on the various tissue protective cytokines of the invention.

A tissue protective cytoline of the invention may consist of erythropoietin having at least no sialic acid moieties, referred to as asialoerythropoietin. Preferably, a tissue protective cytokine of the invention is human asialoerythropoietin. It may be prepared by desialylating erythropoietin using a sialidase, such as is described in the manufacturer's packaging for Sialydase A from ProZyme Inc., San Leandro, Calif. Typically, PROZYME® GLYCOPRO® sequencing-grade SIALYDASE A™ (N-acetylneuraminate glycohydrolase, EC 3.2.1.18) is used to cleave all non-reducing terminal sialic acid residues from complex carbohydrates and glycoproteins such as erythropoietin. It will also cleave branched sialic acids (linked to an internal residue). Sialydase A is isolated from a clone of *Arthrobacter ureafaciens*.

In a non-limiting example of the foregoing procedure, erythropoietin may be subjected to desialylation by sialidase (0.025 U/mg EPO) at 37 C for 3 h, after which the erythropoietin may be desalted and concentrated. After passing over an ion exchange column using the AKTAPRIME™ system (Amersham Pharmacia Biotech), and elution with selected buffers, the fractions containing only the top two bands identified by imunoelectrophoresis (migrating at pI ~8.5 and ~7.9 on IEF gel) are selected. No significant amount of sialic acid should be detected in this preparation of the tissue protective cytokine.

In alternative embodiments, the tissue protective cytokine of the invention may be an erythropoietin having at least 1, 2, 3, 4, 5, 6, 7, 8, 9, 10, 11, 12, or 13 sialic acid residues, by partial desialylation by the aforementioned method. These tissue protective cytokines resulting form the partial desialylation of erythropoietin may also be referred to herein as hyposialoerythropoietins, and may be a homogeneous composition, with, for example, only 2 sialic acids per erythropoietin molecule, or may be a heterogeneous mixture of a variety of different degrees of sialylation, or, for example, having a low number, such as about 1 to about 4 sialic acid molecules on average per erythropoietin, or, in another example, a higher number, such as about 10 to about 13 sialic acids on average per erythropoietin molecule. Such mixtures may include asialoerythropoietin or erythropoietin.

An erythropoietin for the aforementioned uses may have at least one or more modified arginine residues. For example, the modified erythropoietin may comprise an R-glyoxal moiety on the one or more arginine residues, where R may be an aryl, heteroaryl, lower alkyl, lower alkoxy, or cycloalkyl group, or an alpha-deoxyglycitolyl group. As used herein, the term lower "alkyl" means a straight- or branched-chain saturated aliphatic hydrocarbon group preferably containing 1-6 carbon atoms. Representative of such groups are methyl, ethyl, isopropyl, isobutyl, butyl, pentyl, hexyl and the like. The term "alkoxy" means a lower alkyl group as defined above attached to the remainder of the molecule by oxygen. Examples of alkoxy include methoxy, ethoxy, propoxy, isopropoxy and the like. The term "cycloalkyl" refers to cyclic alkyl groups with from three to up to about 8 carbons, including for example cyclopropyl, cyclobutyl, cyclohexyl and the like. The term aryl refers to phenyl and naphthyl groups. The term heteroaryl refers to heterocyclic groups containing 4-10 ring members and 1-3 heteroatoms selected from the group consisting of oxygen, nitrogen and sulfur. Examples include but are not limited to isoxazolyl, phenylisoxazolyl, furyl, pyrimidinyl, quinolyl, tetrahydroquinolyl, pyridyl, imidazolyl, pyrrolidinyl, 1,2,4-triazoylyl, thiazolyl, thienyl, and the like. The R group may be substituted, as for example the 2,3,4-trihydroxybutyl group of 3-deoxyglucosone. Typical examples of R-glyoxal compounds are glyoxal, methylglyoxal, 3-deoxyglucosone, and phenylglyoxal. Preferred R-glyoxal compounds are methylglyoxal or phenylglyoxal. An exemplary method for such modification may be found in Werber et al., 1975, Isr. J. Med. Sci. 11(11): 1169-70, using phenylglyoxal.

In a further example, at least one arginine residue may be modified by reaction with a vicinal diketone such as 2,3-butanedione or cyclohexanedione, preferably in ca. 50 millimolar borate buffer at pH 8-9. A procedure for the latter modification with 2,3-butanedione may be carried out in accordance with Riordan, 1973, Biochemistry 12(20): 3915-3923; and that with cyclohexanone according to Patthy et al., 1975, J. Biol. Chem 250(2): 565-9.

A tissue protective cytokine of the invention may comprise at least one or more modified lysine residues or a modification of the N-terminal amino group of the erythropoietin molecule, such modifications as those resulting from reaction of the lysine residue with an amino-group-modifying agent. For example, erythropoietin or aforementioned asialoerythropoietin or hyposialoerythropoietin, may be modified by acetylation, carbamylation, succinylation, oxidation and subsequent carboxymethyllysination, among other methods, to modify amino groups.

In a non-limiting example, tissue protective cytokine may be generated by carbamylating an erythropoietin, or a desialylated erythropoietin such as asialoerythropoietin, with recrystallized potassium cyanate in borate buffer, after which thorough dialysis is performed.

Likewise, an aforementioned erythropoietin may be succinylated by reaction with succinic anhydride, followed by dialysis to form a tissue protective cytokine of the present invention.

In yet another embodiment, a tissue protective cytokine may be generated by reacting erythropoietin with acetic anhydride in phosphate buffer to acetylate the erythropoietin. This reaction may be stopped by dialysis against water. The method is described in Satake et al, (1990). Chemical modification of erythropoietin: an increase in in-vitro activity by guanidination. Biochimica et Biophysica Acta. 1038: 125-129.

In another embodiment, the tissue protective cytokines are $N^\epsilon$-(carboxymethyl)lysine (CML) adducts from erythropoietin or asialoerythropoietin prepared by reaction with glyoxylic acid and $NaBH_3CN$ in sodium phosphate buffer, followed by dialysis. Akhtar et al., (1999) Conformational study of $N^\epsilon$-(carboxymethyl)lysine adducts of recombinant a-crystallins. Current Eye Research, 18: 270-276.

In another embodiment, a tissue protective cytokine is generated by modifying the lysine residues of erythropoietin by reaction with glyoxal derivatives, such as reaction with glyoxal, methylglyoxal and 3-deoxyglucosone to form alpha-carboxyalkyl derivatives. Examples include reaction with glyoxal to form a carboxymethyllysine residue as in Glomb and Monnier, 1995, J. Biol. Chem. 270(17):10017-26, or with methylglyoxal to form a (1-carboxyethyl)lysine residue as in Degenhardt et al., 1998, Cell. Mol. Biol. (Noisy-le-grand) 44(7):1139-45. The modified lysine residue further may be chemically reduced. For example, the erythropoietin may be biotinylated via lysine groups, such as in accordance with the method described in Example 2, in which D-biotinoyl-ε-aminocaproic acid-N-hydroxysuccinimide ester was reacted with erythropoietin, followed by removal of unreacted biotin by gel filtration on a Centricon 10 column, as described by Wojchowski and Caslake, 1989, Blood 74(3):952-8. In this paper, the authors use three different methods of biotinylating erythropoietin, any of which may be used for the preparation of the tissue protective cytokines for the uses herein. Biotin may be added to (1) the sialic acid moieties (2) carboxylate groups or (3) amino groups.

In another preferred embodiment, the lysine may be reacted with an aldehyde or reducing sugar to form an imine, which may be stabilized by reduction as with sodium cyanoborohydride to form an N-alkylated lysine residue such as glucitolyl lysine, or which in the case of reducing sugars may be stabilized by Amadori or Heyns rearrangement to form an alpha-deoxy alpha-amino sugar such as alpha-deoxy-alpha-fructosyllysine residue in the erytiropoietin molecule. As an example, preparation of a fructosyllysine-modified protein by incubation with 0.5 M glucose in sodium phosphate buffer at pH 7.4 for 60 days is described by Makita et al., 1992, J. Biol. Chem. 267:5133-5138. In another example, the lysine group maybe carbamylated, such as by virtue of reaction with cyanate ion, or alkyl- or aryl-carbamylated or -thiocarbamylated with an alkyl- or aryl-isocyanate or -isothiocyanate, or it may be acylated by a reactive alkyl- or arylcarboxylic acid derivative, such as by reaction with acetic anhydride or succinic anhydride or phthalic anhydride. Exemplary are the modification of lysine groups with 4-sulfophenylisothiocyanate or with acetic anhydride, both as described in Gao et al., 1994, Proc Natl Acad Sci USA 91(25): 12027-30. Lysine groups may also be trinitrophenyl modified by reaction with trinitrobenzenesulfonic acid or preferably its salts. Such methods are described below in Example 2.

At least one tyrosine residue of an erythropoietin may be modified in an aromatic ring position by an electrophilic reagent, such as by nitration or iodination to generate a tissue protective cytokine. By way of nion-limiting example, erythropoietin may be reacted with tetranitromethane (Nestler et al., 1985, J. Biol. Chem. 260(12):7316-21; or iodinated as described in Example 3. For example, iodination with NaI and IODO-GEN Pre-Coated Iodination Tube (Pierce, 28601), may be carried out using erythropoietin or asialoerythropoietin in sodium phosphate buffer.

At least an aspartic acid or a glutamic acid residue of an erythropoietin may be modified, such as by reaction with a carbodiimide followed by reaction with an amine such as but not limited to glycinamide.

In another example, a tryptophan residue of an erythropoietin may be modified, such as by reaction with n-bromosuccinimide or n-chlorosuccinimide, following methods such as described in Josse et al., Chem Biol Interact 1999 May 14;1 19-120.

In yet another example, a tissue protective cytokine may be prepared by removing at least one amino group of a native erythropoietin, such may be achieved by reaction with ninhydrin followed by reduction of the subsequent carbonyl group by reaction with borohydride.

In still a further example, a tissue protective cytokine is provided that has at least an opening of at least one of the cystine linkages in the erythropoietin molecule by reaction with a reducing agent such as dithiothreitol, followed by reaction of the subsequent sulfhydryls with iodoacetamide, iodoacetic acid or another electrophile to prevent reformation of the disulfide linkages. As noted above, alternatively or in combination, disulfide linkages may be abolished by altering a cysteine molecule that participates in the actual cross-link or at least one other amino acid residue that results in the inability of the erythropoietin to form at least one of the disulfide linkages present in the native molecule.

A tissue protective cytokine may be prepared by subjecting an erythropoietin to a limited chemical proteolysis that targets specific residues, for example, to cleave after tryptophan residues. Such resulting erythropoietin fragments are embraced herein.

As noted above, a tissue protective cytokine useful for the purposes herein may have at least one of the aforementioned modifications, but may have more than one of the above modifications. By way of example of a tissue protective cytokine with one modification to the carbohydrate portion of the molecule and one modification to the amino acid portion, a tissue protective cytokine may be asialoerythropoietin and have its lysine residues biotinylated or carbamylated.

Moreover, the chemically modified erythropoietin may be further modified by mutating at least one amino acid of the erythropoietin. Such mutations may include substitutions, deletions, including internal deletions, additions, including additions yielding fusion proteins, or conservative substitutions of amino acid residues within and/or adjacent to the amino acid sequence, but that result in a "silent" change, in that the change produces a functionally equivalent erythropoietin. Conservative amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. Alternatively, non-conservative amino acid changes, and larger insertions and deletions may be used to create functionally altered erythropoietin. Such mutants can be used to alter erythropoietin properties in desirable ways. For example, in one embodiment, an erythropoietin useful for the practice of the invention can be altered in one or more amino acids within the four functional domains of erythropoietin which affect receptor binding: VLQRY (SEQ ID NO:1) and/or TKVNFYAW (SEQ ID NO:2) and/or SGLRSLTTL (SEQ ID NO:3) and/or SNFLRG (SEQ ID NO:4). In another embodiment, erythropoietins containing mutations in the surrounding areas of the molecule which affect the kinetics or receptor-binding properties of the molecule can be used.

These additional modifications may be used to enhance the tissue protective effect, suppress the bone marrow effect, or alter the physical properties, such as charge, of the tissue protective cytokine.

The foregoing exemplary methods for preparing tissue protective cytokines of the invention are merely illustrative and non-limiting, and these or other methods may be used to prepare the compounds of the invention. The names hereinabove wherein the method of preparation is contained within the name, such as "acetylated" or "biotinylated," are provided herein merely as a means for understanding how the compound was made, yet the present invention is directed to the compounds that are products of the aforementioned reactions. One of skill in the art would readily recognize the compounds that are the products of the reactions mentioned above. Heretofore the compounds of the invention have been referred to by informal or trivial names to convey the scope of the modifications of the invention and that they may occur at one or more sites on the erythropoietin or modified erythropoietin molecule. By ways of non-limiting examples, the following specific compounds are members of the compound groups embraced herein.

1. Carbamylated erythropoietins: The following compounds represent carbamoyl moieties on the N-terminal amino acid of an erythropoietin molecule ("alpha-N-carbamoyl-") or on one (or more) epsilon amino groups of lysyl residues of erythropoietin ("N-epsilon-carbamoyl-"). Of course, multiple N-epsilon modifications with or without the alpha-N-modification may be present.
  i. alpha-N-carbamoylerythropoietin
  ii. N-epsilon-carbamoylerythropoietin
  iii. alpha-N-carbamoyl, N-epsilon-carbamoylerythropoietin
  iv. alpha-N-carbamoylasialoerythropoietin
  v. N-epsilon-carbamoylasialoerythropoietin
  vi. alpha-N-carbamoyl, N-epsilon-carbamoylasialoerythropoietin
  vii. alpha-N-carbamoylhyposialoerythropoietin
  viii. N-epsilon-carbamoylhyposialoerythropoietin, and
  ix. alpha-N-carbamoyl, N-epsilon-carbamoylhyposialoerythropoietin 2. Succinylated erythropoietins: The following compounds represent succinyl moieties on the N-terminal amino acid of an erythropoietin molecule ("alpha-N-succinyl-") or on one (or more) epsilon amino groups of lysyl residues of erythropoietin ("N-epsilon-succinyl-"). Of course, multiple N-epsilon modifications with or without the alpha-N-modification may be present.
  i. alpha-N-succinylerythropoietin;
  ii. N-epsilon-succinylerythropoietin;
  iii. alpha-N-succinyl, N-epsilon-succinylerythropoietin;
  iv. alpha-N-succinylasialoerythropoietin;
  v. N-epsilon-succinylasialoerythropoietin;
  vi. alpha-N-succinyl, N-epsilon-succinylasialoerythropoietin;
  vii. alpha-N-succinylhyposialoerythropoietin;
  viii. N-epsilon-succinylhyposialoerythropoietin; and
  ix. alpha-N-succinyl, N-epsilon-succinylhyposialoerythropoietin.

3. Acetylated erythropoietins: The following compounds represent acetyl moieties on the N-terminal amino acid of an erythropoietin molecule ("alpha-N-acetyl-") or on one (or more) epsilon amino groups of lysyl residues of erythropoietin ("N-epsilon-acetyl-"). Of course, multiple N-epsilon modifications with or without the alpha-N-modification may be present.
  i. alpha-N-acetylerythropoietin;
  ii. N-epsilon-acetylerythropoietin;
  iii. alpha-N-acetyl, N-epsilon-acetylerythropoietin;
  iv. alpha-N-acetylasialoerythropoietin;
  v. N-epsilon-acetylasialoerythropoietin;
  vi. alpha-N-acetyl, N-epsilon-acetylasialoerythropoietin;
  vii. alpha-N-acetylhyposialoerythropoietin;
  viii. N-epsilon-acetylhyposialoerythropoietin; and
  ix. alpha-N-acetyl, N-epsilon-acetylhyposialoerythropoietin.

4. Biotinylated erythropoietins: The following compounds represent biotinyl moieties on the N-terminal amino acid of an erythropoietin molecule ("alpha-N-biotinyl-") or on one (or more) epsilon amino groups of lysyl residues of erythropoietin ("N-epsilon-biotinyl-"). Of course, multiple N-epsilon modifications with or without the alpha-N-modification may be present.
    i. alpha-N-biotinylerythropoietin;
    ii. N-epsilon-biotinylerythropoietin;
    iii. alpha-N-biotinyl, N-epsilon-biotinylerythropoietin;
    iv. alpha-N-biotinylasialoerythropoietin;
    v. N-epsilon-biotinylasialoerythropoietin;
    vi. alpha-N-biotinyl, N-epsilon-biotinylasialoerythropoietin;
    vii. alpha-N-biotinylhyposialoerythropoietin;
    viii. N-epsilon-biotinylhyposialoerythropoietin; and
    ix. alpha-N-biotinyl, N-epsilon-biotinylhyposialoerythropoietin.

5. Iodinated erythropoietins: Of course, one of ordinary skill in the art would recognize that several different tyrosine residues as well as combinations of tyrosine residues within erythropoietin may be iodinated and that ones provided are merely illustrative.
    i. Iodoerythropoietin;
    ii. Iodoasialoerythropoietin; and
    iii. Iodohyposialoerythropoietin.

6. Carboxymethyllysyl-erythropoietins: The following compounds represent carboxymethyl moieties on one (or more) epsilon amino groups of lysyl residues of erythropoietin ("N-epsilon-carboxymethyl-"). Of course, multiple N-epsilon modifications may be present.
    i. N-epsilon-carboxymethylerythropoietin;
    ii. N-epsilon-carboxymethylasialoerythropoietin; and
    iii. N-epsilon-carboxymethylhyposialoerythropoietin.

A variety of host-expression vector systems may be utilized to produce the erythropoietins and erythropoietin-related molecules of the invention. Such host-expression systems represent vehicles by which the erythropoietins of interest may be produced and subsequently purified, but also represent cells that may, when transformed or transfected with the appropriate nucleotide coding sequences, exhibit the modified erythropoietin gene product in situ. These include but are not limited to, bacteria, insect, plant, mammalian, including human host systems, such as, but not limited to, insect cell systems infected with recombinant virus expression vectors (e.g., baculovirus) containing the modified erythropoietin product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing erythropoietin-related molecule coding sequences; or mammalian cell systems, including human cell systems, (e.g., HT1080, COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In addition, a host cell strain may be chosen that modulates the expression of the inserted sequences, or modifies and processes the gene product in the specific fashion-desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells, including human host cells, include but are not limited to HT1080, CHO, VERO, BHK, HeLa, COS, MDCK, 293, 3T3, and W138.

For long-term, high-yield production of recombinant proteins, stable expression is preferred. For example, cell lines that stably express the erythropoietin-related molecule gene product may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines that express the erythropoietin-related molecule gene product. Such engineered cell lines may be particularly useful in screening and evaluation of compounds that affect the endogenous activity of the erythropoietin-related molecule gene product.

Alternatively, the expression characteristic df an endogenous erythropoietin gene within a cell line or microorganism may be modified by inserting a heterologous DNA regulatory element into the genome of a stable cell line or cloned microorganism such that the inserted regulatory element is operatively linked with the endogenous erythropoietin gene. For example, an endogenous erythropoietin gene which is normally "transcriptionally silent," i.e., an erythropoietin gene which is normally not expressed, or is expressed only a very low levels in a cell line, may be activated by inserting a regulatory element which is capable of promoting the expression of a normally expressed gene product in that cell line or microorganism. Alternatively, a transcriptionally silent, endogenous erythropoietin gene may be activated by insertion of a promiscuous regulatory element that works across cell types.

A heterologous regulatory element may be inserted into a stable cell line or cloned microorganism, such that it is operatively linked with an endogenous erythropoietin gene, using techniques, such as targeted homologous recombination, which are well known to those of skill in the art, and described e.g., in French Patent No. 2646438 to Institut Pasteur, U.S. Pat. No. 4,215,051 to Chappel; U.S. Pat. No. 5,578,461 to Shervin et al.; International Application No. PCT/US92/09627 (WO93/09222) by Selden et al.; and International Application No. PCT/US90/06436 (WO91/06667) by Skoultchi et al., each of which is incorporated by reference herein in its entirety.

In one embodiment of the invention, a tissue protective cytokine is a chemically modified erythropoietin molecule deficient in sialic residues, or completely lacking sialic residues, and may be produced in mammalian cell, including a human cell. Such cells may be engineered to be deficient in, or lacking, the enzymes that add sialic acids, i.e., the β-galactoside α2,3 sialyltransferase (Aα2,3 sialyltransferase@) and the β-galactoside α2,6 sialyltransferase (Aα2,6 sialyltransferase@) activity. In one embodiment, a mammalian cell is used in which either or both the α2,3 sialyltransferase gene and/or the α2,6 sialyltransferase gene, is deleted. Such deletions may be constructed using gene knock-out techniques well known in the art. In another embodiment, dihydrofolate reductase (DHFR) deficient Chinese Hamster Ovary (CHO) cells are used as the host cell for the production of recombinant erythropoietin-related molecules. CHO cells do not express the enzyme α2,6 sialyltransferase and therefore do not add sialic acid in the 2,6 linkage to N-linked oligosaccharides of glycoproteins produced in these cells. As a result, recombinant proteins produced in CHO cells lack sialic acid in the 2,6 linkage to galactose (Sasaki et al. (1987; Takeuchi et al. supra; Mutsaers et al Eur. J. Biochem. 156, 651 (1986); Takeuchi et al. J. Chromotgr. 400, 207 (1987). In one embodiment, to produce a host cell for the production of asialoerythropoietin, the gene encoding α2, 3 sialyltransferase in CHO cells is deleted. Such α2,3 sialyltransferase knock-out CHO cells completely lack sialyltransferase activity, and as a result, are useful for the recombinant expression and production of a tissue protective cytokine consists of asialo-erythropoietin.

In another embodiment, asialo glycoproteins can be produced by interfering with sialic acid transport into the Golgi apparatus e.g., Eckhardt et al., 1998, J. Biol. Chem. 273: 20189-95). Using methods well known to those skilled in the art (e.g., Oelmann et al., 2001, J. Biol. Chem. 276:26291-300), mutagenesis of the nucleotide sugar CMP-sialic acid transporter can be accomplished to produce mutants of Chinese hamster ovary cells. These cells cannot add sialic acid residues to glycoproteins such as erythropoietin and produce only asialoerythropoietin.

Transfected mammalian cells producing erythropoietin also produce cytosolic sialidase which if it leaks into the culture medium degrades sialoerythropoietin with high efficiency (e.g., Gramer et al, 1995 Biotechnology 13:692-698). Using methods well known to those knowledgeable in the art (e.g., from information provided in Ferrari et al, 1994, Glycobiology 4:367-373), cell lines can be transfected, mutated or otherwise caused to constitutively produce sialidase. In this manner, asialoerythropoietin can be produced during the manufacture of asialoerythropoietin.

A tissue protective cytokine of the invention has at least one modification of an amino acid residue in erythropoietin, regardless of the glycosylation state of the molecule. As mentioned above, the chemical modification may be at least a modification of at least one amino group of at least one amino acid, such as a lysine residue, or the N-terminal amino group, or iodination of at least one tyrosine residue.

Following the manufacture of the recombinant tissue protective cytokines and chemically modified recombinant tissue protective cytokines of the present invention, one of ordinary skill in the art can verify the tissue protective attributes of the cytokines and the absence of an effect on the bone marrow using well known assays.

For example, the non-erythropoietic affect of a recombinant tissue protective cytokine can be verified through the use of a TF-1 assay. In this assay TF-1 cells are grown in a complete RPMI medium supplemented with 5 ng/ml of GM-CSF and 10% FCS for a day at 37 C in a $CO_2$ incubator. The cells are then washed in and suspended at a density of $10^6$ cells/ml for 16 hours in starvation medium (5% FCS without GM-CSF). A 96 well plate is prepared by: (1) adding 100 μl of sterile water to the outer wells to maintain moisture; (2) adding medium (10% FCS without cells or GM-CSF) alone to 5 wells; and (3) seeding 25,000 cells/well with medium containing 10% FCS and the recombinant tissue protective cytokines in remaining wells (five wells per cytokine being tested). If the cells proliferate, the recombinant tissue protective cytokine may be erythropoietic. The in vivo affect of the compound should then be tested on an in vivo assay monitoring an increase of hematocrit due to the recombinant tissue protective cytokine. A negative result—non-proliferation of cells in the TF-1 assay in vitro assay or no increase in hematocrit within the in vivo assay—means that the recombinant tissue protective cytokine is nonerythropoietic.

The tissue protective properties of the recombinant tissue protective cytokine may be verified using a P-19 in vitro assay or a water intoxication in vivo assay in rats, both of which are outlined in further detail below. The above assays are provided merely as examples, and other suitable assays to determine the effect of the cytokines on bone marrow and tissue protection are known to those of ordinary skill in the art are contemplated by the present invention as well.

In the practice of one aspect of the present invention, a pharmaceutical composition as described above containing a tissue protective cytokine may be administrable to a mammal by any route which provides a sufficient level of a tissue protective cytokine in the vasculature to permit translocation across an endothelial cell barrier and beneficial effects on responsive cells. When used for the purpose of perfusing a tissue or organ, similar results are desired. In the instance wherein the tissue protective cytokine is used for ex-vivo perfusion, the tissue protective cytokine may be any of the aforementioned chemically-modified erythropoietins. In the instance where the cells or tissue is non-vascularized and/or the administration is by bathing the cells or tissue with the composition of the invention, the pharmaceutical composition provides an effective responsive-cell-beneficial amount of a tissue protective cytokine. The endothelial cell barriers across which a tissue protective cytokine may translocate include tight junctions, perforated junctions, fenestrated junctions, and any other types of endothelial barriers present in a mammal. A preferred barrier is an endothelial cell tight junction, but the invention is not so limiting.

The aforementioned tissue protective cytokines are useful generally for the therapeutic or prophylactic treatment of human diseases of the central nervous system or peripheral nervous system which have primarily neurological or psychiatric symptoms, ophthalmic diseases, cardiovascular diseases, cardiopulmonary diseases, respiratory diseases, kidney, urinary and reproductive diseases, bone diseases, skin diseases, gastrointestinal diseases and endocrine and metabolic abnormalities. In particular, such conditions and diseases include hypoxic conditions, which adversely affect excitable tissues, such as excitable tissues in the central nervous system tissue, peripheral nervous system tissue, or cardiac tissue or retinal tissue such as, for example, brain, heart, or retina/eye. Therefore, the invention can be used to treat or prevent damage to excitable tissue resulting from hypoxic conditions in a variety of conditions and circumstances. Non-limiting examples of such conditions and circumstances are provided in the table herein below.

In the example of the protection of neuronal tissue pathologies treatable in accordance with the present invention, such pathologies include those which result from reduced oxygenation of neuronal tissues. Any condition which reduces the availability of oxygen to neuronal tissue, resulting in stress, damage, and finally, neuronal cell death, can be treated by the methods of the present invention. Generally referred to as hypoxia and/or ischemia, these conditions arise from or include, but are not limited to stroke, vascular occlusion, prenatal or postnatal oxygen deprivation, suffocation, choking, near drowning, carbon monoxide poisoning, smoke inhalation, trauma, including surgery and radiotherapy, asphyxia, epilepsy, hypoglycemia, chronic obstructive pulmonary disease, emphysema, adult respiratory distress syndrome, hypotensive shock, septic shock, anaphylactic shock, insulin shock, sickle cell crisis, cardiac arrest, dysrhythmnia, nitrogen narcosis, and neurological deficits caused by heart-lung bypass procedures.

In one embodiment, for example, the specific tissue protective cytokine compositions can be administered to prevent injury or tissue damage resulting from risk of injury or tissue damage during surgical procedures, such as, for example, tumor resection or aneurysm repair. Other pathologies caused by or resulting from hypoglycemia which are treatable by the methods described herein include insulin overdose, also referred to as iatrogenic hyperinsulinemia, insulinoma, growth hormone deficiency, hypocortisolism, drug overdose, and certain tumors.

Other pathologies resulting from excitable neuronal tissue damage include seizure disorders, such as epilepsy, convulsions, or chronic seizure disorders. Other treatable conditions and diseases include diseases such as stroke, multiple sclerosis, hypotension, cardiac arrest, Alzheimer's disease, Parkinson's disease, cerebral palsy, brain or spinal cord trauma, AIDS dementia, age-related loss of cognitive function, memory loss, amyotrophic lateral sclerosis, seizure disorders, alcoholism, retinal ischemia, optic nerve damage resulting from glaucoma, and neuronal loss.

The specific composition and methods of the present invention may be used to treat inflammation resulting from disease conditions or various traumas, such as physically or chemically induced inflammation. Such traumas could include angitis, chronic bronchitis, pancreatitis, osteomyelitis, rheumatoid arthritis, glomerulonephritis, optic neuritis, temporal arteritis, encephalitis, meningitis, transverse myelitis, dermatomyositis, polymyositis, necrotizing fascilitis, hepatitis, and necrotizing enterocolitis.

Evidence has demonstrated that activated astrocytes can exert a cytotoxic role towards neurons by producing neurotoxins. Nitric oxide, reactive oxygen species, and cytokines are released from glial cells in response to cerebral ischemia (see Becker, K. J. 2001. Targeting the central nervous system inflammatory response in ischemic stroke. *Curr Opinion Neurol* 14:349-353 and Mattson, M. P., Culmsee, C., and Yu, Z.F. 2000. Apoptotic and Antiapoptotic mechanisms in stroke. *Cell Tissue Res* 301:173-187.). Studies have further demonstrated that in models of neurodegeneration, glial activation and subsequent production of inflammatory cytokines depends upon primary neuronal damage (see Viviani, B., Corsini, E., Galli, C. L., Padovani, A., Ciusani, E., and Marinovich, M. 2000. Dying neural cells activate glia through the release of a protease product. *Glia* 32:84-90 and Rabuffetti, M., Scioratti, C., Tarozzo, G., Clementi, E., Manfredi, A. A., and Beltramo, M. 2000. Inhibition of caspase-1-like activity by Ac-Tyr-Val-Ala-Asp-chloromethyl ketone includes long lasting neuroprotection in cerebral ischemia through apoptosis reduction and decrease of proinflanmmatory cytokines. *J Neurosci* 20:4398-4404). Inflammation and glial activation is common to different forms of neuro degenerative disorders, including cerebral ischemia, brain trauma and experimental allergic encephalomyelitis, disorders in which erythropoietin exerts a neuroprotective effect. Inhibition of cytokine production by erythropoietin could, at least in part, mediate its protective effect. However, unlike "classical" anti-inflammatory cytokines such as Il-10 and IL-13, which inhibit tumor necrosis factor production directly, erythropoietin appears to be active only in the presence of neuronal death.

While not wishing to be bound by any particular theory it appears that this anti-inflammatory activity may be hypothetically explained by several non-limiting theories. First, since erythropoietin prevents apoptosis, inflammatory events triggered by apoptosis would be prevented. Additionally, erythropoietin may prevent the release of molecular signals from dying neurons which stimulate the glia cells or could act directly on the glial cells reducing their reaction to these products. Another possibility is that erythropoietin targets more proximal members of the inflammatory cascade (e.g., caspase 1, reactive oxygen or nitrogen intermediates) that trigger both apoptosis and inflammation.

Furthermore, erythropoietin appears to provide anti-inflammatory protection without the rebound affect typically associated with other anti-inflammatory compounds such as dexamethasone. Once again, not wishing to be bound by any particular theory, it appears as though this may be due to erythropoietin's affect on multipurpose neuro toxins such as nitric oxide (NO). Although activated astrocytes and microglia produce neurotoxic quatities of NO in response to various traumas, NO serves many purposes within the body including the modulation of essential physiological functions. Thus, although the use of an anti-inflammatory may alleviate inflammation by suppressing NO or other neuro toxins, if the anti-inflammatory has too long a half-life it may also interfere with these chemical's roles in repairing the damage resulting from the trauma that led to the inflammation. It is hypothesized that the tissue protective cytokines of the present invention are able to alleviate the inflammation without interfering with the restorative capabilities of neurotoxins such as NO.

The present invention provides compositions comprising one or more tissue protective cytokines and one or more prophylactic or therapeutic agents (i.e., active agents) other than tissue protective cytokines, and methods for preventing, treating or ameliorating one or more symptoms associated with inflammation of responsive mammalian cells and their associated cells, tissues and organs in a mammal comprising administering to said mammal one or more of said compositions. The present invention also provides compositions comprising one or more tissue protective cytokines and methods for preventing, treating or ameliorating one or more symptoms associated with inflammation of responsive mammalian cells and their associated cells, tissues and organs in a mammal comprising administering to said mammal one or more of said compositions, wherein the compositions are administered in conjunction with one or more prophylactic or therapeutic agents other than tissue protective cytokines. The inflammation may be caused by injury or a disease, such as, but not limited to, disorder is asthma, encephalitis, inflammatory bowel disease, chronic obstructive pulmonary disease (COPD), arthritis, or an allergic disorder. Therapeutic or prophylactic agents include, but are not limited to, peptides, polypeptides, fusion proteins, nucleic acid molecules, small molecules, mimetic agents, synthetic drugs, inorganic molecules, and organic molecules. Any agent which is known to be useful, or which has been used or is currently being used for the prevention, treatment or amelioration of one or more symptoms associated with inflammation can be used in combination with a tissue protective cytokine in accordance with the invention described herein. Examples of such agents include, but are not limited to, dermatological agents for rashes and swellings (e.g., phototherapy (i.e., ultraviolet B radiation), photochemotherapy (e.g., PUVA) and topical agents such as emollients, salicyclic acid, coal tar, topical steroids, topical corticosteroids, topical vitamin D3 analogs (e.g., calcipotriene), tazarotene, and topical retinoids), anti-inflammatory agents (e.g., corticosteroids (e.g., prednisone and hydrocortisone), glucocorticoids, steroids, non-steriodal anti-inflammatory drugs (e.g., aspirin, ibuprofen, diclofenac, and COX-2 inhibitors), beta-agonists, anticholinergic agents and methyl xanthines), immunomodulatory agents (e.g., small organic molecules, a T cell receptor modulators, cytokine receptor modulators, T-cell depleting agents, cytokine antagonists, monokine antagonists, lymphocyte inhibitors, or anti-cancer agents), gold injections, sulphasalazine, penicillamine, anti-angiogenic agents (e.g., angiostatin, TNF-α antagonists (e.g., anti-TNFα antibodies), and endostatin), dapsone, psoralens (e.g., methoxalen and trioxsalen), anti-malarial agents (e.g., hydroxychloroquine), anti-viral agents, and antibiotics (e.g., erythomycin and penicillin).

Any immunomodulatory agent well-known to one of skill in the art may be used in the methods and compositions of the invention. Inmunomodulatory agents can affect one or more or all aspects of the immune response in a subject. Aspects of the immune response include, but are not limited to, the inflammatory response. In a preferred embodiment of the invention, the administration of an immunomodulatory agent to a subject inhibits or reduces one or more aspects of the subject's immune response capabilities. In a specific embodiment of the invention, the immunomodulatory agent inhibits or suppresses the inflammatory response in a subject. In one embodiment, a tissue protective cytokine of the invention is administered in combination with one or more immunomodulatory agents to treat, i.e. ameliorate the symptoms of, or prevent inflammation.

Examples of immunomodulatory agents include, but are not limited to, proteinaceous agents such as cytokines, peptide rnimetics, and antibodies (e.g., human, hurnanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. In particular, immunomodulatory agents include, but are not limited to, methothrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steriods, mycophenolate mofetil, rapamycin (sirolimus),rnizoribine, deoxyspergualin, brequinar, malononitriloariindes (e.g. leflunamide), T cell receptor modulators, and cytokine receptor modulators. Examples of T cell receptor modulators include, but are not limited to, anti-T cell receptor antibodies (e.g., anti-CD4 antibodies (e.g., cM-T412 (Boeringer), IDEC-CE9.1® (IDEC and SKB), mAB 4162W94, Orthoclone and OKTcdr4a (Janssen-Cilag)), anti-CD3 antibodies, anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies, anti-CD52 antibodies (e.g., CAMPATH 1H (Ilex)), anti-CD2 monoclonal antibodies) and CTLA4-immunoglobulin.

Examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokinies or fragments thereof (e.g., interleukin (IL)-2, IL-3, IL-4, IL-5, IL-6, IL-7, IL-8, IL-9, IL-10, IL-11, IL-12, IL-15, TNF-α, TNF-β, interferon (IFN)-α, IFN-β, IFN-γ, and GM-CSF), anti-cytokine receptor antibodies (e.g., anti-IL-2 receptor antibodies, anti-IL-4 receptor antibodies, anti-IL-6 receptor antibodies, anti-IL-10 receptor antibodies, and anti-IL-12 receptor antibodies), anti-cytokine antibodies (e.g., anti-IFN receptor antibodies, anti-TNF-α antibodies, anti-IL-1β antibodies, anti-IL-6 antibodies, and anti-IL-12 antibodies). In a specific embodiment, a cytokine receptor modulator is IL-4, IL-10, or a fragment thereof. In another embodiment, a cytokine receptor modulator is an anti-IL-1β antibody, anti-IL-6 antibody, anti-IL-12 receptor antibody, anti-TNF-c antibody. In another embodiment, a cytokine receptor modulator is the extracellular domain of a TNF-α receptor or a fragment thereof. In certain embodiments, a cytokine receptor modulator is not a TNF-α antagonist.

In a preferred embodiment, proteins, polypeptides or peptides (including antibodies) that are utilized as immunomodulatory agents are derived from the same species as the recipient of the proteins, polypeptides or peptides so as to reduce the likelihood of an immune response to those proteins, polypeptides or peptides. In another preferred embodiment, when the subject is a human, the proteins, polypeptides, or peptides that are utilized as immunomodulatory agents are human or humanized.

In accordance with the invention, one or more immunomodulatory agents are administered to a subject with inflammation prior to, subsequent to, or concomitantly with the therapeutic and/or prophylactic agents of the invention. Preferably, one or more immunomodulatory agents are administered to a subject with inflammation to reduce or inhibit one or more aspects of the immune response as necessary. Any technique well-known to one skilled in the art can be used to measure one or more aspects of the immune response in a particular subject, and thereby determine when it is necessary to administer an immunomodulatory agent to said subject.

In a preferred embodiment, one or more immunomodulatory agents are administered to a subject with inflammation so as to transiently reduce or inhibit one or more aspects of the immune response. Such a transient inhibition or reduction of one or more aspects of the immune system can last for hours, days, weeks, or months. Preferably, the transient inhibition or reduction in one or more aspects of the immune response last for a few hours (e.g., 2 hours, 4 hours, 6 hours, 8 hours, 12 hours, 14 hours, 16 hours, 18 hours, 24 hours, 36 hours, or 48 hours), a few days (e.g., 3 days, 4 days, 5 days, 6 days, 7 days, or 14 days), or a few weeks (e.g., 3 weeks, 4 weeks, 5 weeks or 6 weeks). The transient reduction or inhibition of one or more aspects of the immune,response enhances the prophylactic and/or therapeutic capabilities of a tissue protective cytokine.

In one embodiment of the invention, an immunomodulatory agent that reduces or depletes T cells, preferably memory T cells, is administered to a subject with inflammation in accordance with the methods of the invention. See, e.g., U.S. Pat. No. 4,658,019. In another embodiment of the invention, an immunomodulatory agent that inactivates CD8$^+$ T cells is administered to a subject with inflammation in accordance with the methods of the invention. In a specific embodiment, anti-CD8 antibodies are used to reduce or deplete CD8$^+$ T cells.

The CD40 ligand (CD40L)-CD40 interaction is a desirable point to block the immune response because of its broad activity in both T helper cell activation and function as well as the absence of redundancy in its signaling pathway. Thus, in a specific embodiment of the invention, the interaction of CD40L with CD40 is transiently blocked at the time of administration of one or more of the immunoriodulatory agents. This can be accomplished by treating with an agent which blocks the CD40 ligand on the TH cell and interferes with the normal binding of CD40 ligand on the T helper cell with the CD40 antigen on the B cell. An antibody to CD40 ligand (anti-CD40L) (available from Bristol-Myers Squibb Co; see, e.g., European patent application 555,880, published Aug. 18, 1993) or a soluble CD40 molecule can be selected and used as an immunomodulatory agent in accordance with the methods of the invention.

Other examples of immunomodulatory agents which can be used in accordance with the invention include, but are not limited to, corticosteroids, azathioprine, mycophenolate mofetil, cyclosporin A, hydrocortisone, FK506, methotrexate, leflunomide, and cyclophosphamide. A short course of cyclophosphamide has been demonstrated to successfully interrupt both $CD4^+$ and $CD8^+$ T cell activation to adenoviral capsid protein (Jooss et al., 1996, Hum. Gene Ther. 7:1555-1566). Hydrocortisone or cyclosporin A treatment has been successfully used to decrease the induction of cytokines, some of which may be involved in the clearance of bacterial infections and inflammation.

Nucleic acid molecules encoding proteins, polypeptides, or peptides with immunomodulatory activity or proteins, polypeptides, or peptides with immunomodulatory activity can be administered to a subject with inflammation in accordance with the methods of the invention. Further, nucleic acid molecules encoding derivatives, analogs, fragments or variants of proteins, polypeptides, or peptides with immunomodulatory activity, or derivatives, analogs, fragments or variants of proteins, polypeptides, or peptides with immunomodulatory activity can be administered to a subject with inflammation in accordance with the methods of the invention. Prefereably, such derivatives, analogs, variants and fragments retain the immunomodulatory activity of the full-length wild-type protein, polypeptide, or peptide.

Proteins, polypeptides, or peptides that can be used as immunomodulatory agents can be produced by any technique well-known in the art or described herein. See, e.g., Chapter 16 Ausubel et al. (eds.), 1999, Short Protocols in Molecular Biology, Fourth Edition, John Wiley & Sons, NY, which describes methods of producing proteins, polypeptides, or peptides, and which is incorporated herein by reference in its entirety. Antibodies which can be used as immunomodulatory agents can be produced by, e.g., methods described in U.S. Pat. No. 6,245,527 and in Harlow and Lane Antibodies: A Laboratory Manual, Cold Spring Harbor Laboratory Press, Cold Spring Harbor, N.Y., 1988, which are incorporated herein by reference in their entirety. Preferably, agents that are commercially available and known to function as immunomoulatory agents are used in the compositions and methods of the invention. The inuunomodulatory activity of an agent can be determined in vitr-o and/or in vivo by any technique well-known to one skilled in the art, including, e.g., by CTL assays, proliferation assays, and immunoassays (e.g. ELISAs) for the expression of particular proteins such as co-stimulatory molecules and cytokines.

The specific compositions and methods of the invention may be used to treat conditions of, and damage to, retinal tissue. Such disorders include, but are not limited to retinal ischemia, macular degeneration, retinal detachment, retinitis pigmentosa, arteriosclerotic retinopathy, hypertensive retinopathy, retinal artery blockage, retinal vein blockage, hypotension, and diabetic retinopathy.

In another embodiment, the methods and principles of the invention may be used to protect or treat injury resulting from radiation damage to excitable tissue. A further utility of the methods of the present invention is in the treatment of neurotoxin poisoning, such as domoic acid shellfish poisoning, neurolathyrism, and Guam disease, amyotrophic lateral sclerosis, and Parkinson's disease.

As mentioned above, the present invention is also directed to a method for enhancing excitable tissue function in a mammal by peripheral administration of a tissue protective cytokine as described above. Various diseases and conditions are amenable to treatment using this method, and further, this method is useful for enhancing cognitive function in the absence of any condition or disease. These uses of the present invention are describe in further detail below and include enhancement of learning and training in both human and non-human mammals.

Conditions and diseases treatable by the methods of this aspect of the present invention directed to the central nervous system include but are not limited to mood disorders, anxiety disorders, depression, autism, attention deficit hyperactivity disorder, and cognitive dysfunction. These conditions benefit from enhancement of neuronal function. Other disorders treatable in accordance with the teachings of the present invention include sleep disruption, for example, sleep apnea and travel-related disorders; subarachnoid and aneurismal bleeds, hypotensive shock, concussive injury, septic shock, anaphylactic shock, and sequelae of various encephalitides and meningitides, for example, connective tissue disease-related cerebritides such as lupus. Other uses include prevention of or protection from poisoning by neurotoxins, such as domoic acid shellfish poisoning, neurolathyrism, and Guam disease, amyotrophic lateral sclerosis, Parkinson's disease; postoperative treatment for embolic or ischemic injury; whole brain irradiation; sickle cell crisis; and eclampsia.

A further group of conditions treatable by the methods of the present invention include mitochondrial dysfumction, of either a hereditary or acquired nature, which are the cause of a variety of neurological diseases typified by neuronal injury and death. For example, Leigh disease (subacute necrotizing encephalopathy) is characterized by progressive visual loss and encephalopathy, due to neuronal drop out, and myopathy. In these cases, defective mitochondrial metabolism fails to supply enough high energy substrates to fuel the metabolism of excitable cells. An erythropoietin receptor activity modulator optimizes failing function in a variety of mitochondrial diseases. As mentioned above, hypoxic conditions adversely affect excitable tissues. The excitable tissues include, but are not limited to, central nervous system tissue, peripheral nervous system tissue, and heart tissue. In addition to the conditions described above, the methods of the present invention are useful in the treatment of inhalation poisoning such as carbon monoxide and smoke inhalation, severe asthma, adult respiratory distress syndrome, and choking and near drowning. Further conditions which create hypoxic conditions or by other means induce excitable tissue damage include hypoglycemia that may occur in inappropriate dosing of insulin, or with insulin-producing neoplasms (insulinoma).

Various neuropsychologic disorders which are believed to originate from excitable tissue damage are treatable by the instant methods. Chronic disorders in which neuronal damage is involved and for which treatment by the present invention is provided include disorders relating to the central nervous system and/or peripheral nervous system including age-related loss of cognitive function and senile dementia, chronic seizure disorders, Alzheimer's disease, Parkinson's disease, dementia, memory loss, amyotrophic lateral sclerosis, multiple sclerosis, tuberous sclerosis, Wilson's Disease, cerebral and progressive supranuclear palsy, Guam disease, Lewy body dementia, prion diseases, such as spongiform encephalopathies, e.g., Creutzfeldt-Jakob disease, Huntington's disease, myotonic dystrophy, Freidrich's ataxia and other ataxias, as well as Gilles de la Tourette's syndrome, seizure disorders such as epilepsy and chronic seizure disorder, stroke, brain or spinal cord trauma, AIDS dementia, alcoholism, autism, retinal ischemia, glaucoma, autonomic function disorders such as hypertension and sleep disorders, and neuropsychiatric disorders that include, but are not limited to schizophrenia, schizoaffective disorder, attention deficit disorder, dysthymic disorder, major depressive disorder, mania, obsessive-compulsive disorder, psychoactive substance use disorders, anxiety, panic disorder, as well as unipolar and bipolar affective disorders. Additional neuropsychiatric and neurodegenerative disorders include, for example, those listed in the American Psychiatric Association's Diagnostic and Statistical manual of Mental Disorders (DSM), the most current version of which in incorporated herein by reference in its entirety.

In another embodiment, recombinant chimeric toxin molecules comprising erythropoietin can be used for therapeutic delivery of toxins to treat a proliferative disorder, such as cancer, or viral disorder, such as subacute sclerosing panencephalitis.

The following table lists additional exemplary, non-limiting indications as to the various conditions and diseases amenable to treatment by the aforementioned tissue protective cytokines.

| Cell, tissue or organ | Dysfunction or pathology | Condition or disease | Type |
|---|---|---|---|
| Heart | Ischemia | Coronary artery disease | Acute, chronic |
|  |  |  | Stable, unstable |
|  |  | Myocardial infarction | Dressler's syndrome |
|  |  | Angina |  |
|  |  | Congenital heart disease | Valvular |
|  |  |  | Cardiomyopathy |
|  |  | Prinzmetal angina |  |
|  |  | Cardiac rupture | Aneurysmatic |
|  |  |  | Septal perforation |
|  |  | Angiitis |  |
|  | Arrhythmia | Tachy-, bradyarrhythmia | Stable, unstable |
|  |  | Supraventricular, ventricular | Hypersensitive carotid sinus node |
|  |  | Conduction abnormalities |  |
|  | Congestive heart failure | Left, right, bi-ventricular | Cardiomyopathies, such as idiopathic familial, infective, metabolic, storage disease, deficiencies, connective tissue disorder, infiltration and granulomas, neurovascular |
|  |  | Myocarditis | Autoimmune, infective, idiopathic |
|  |  | Cor pulmonale |  |
|  | Blunt and penetrating trauma |  |  |
|  | Toxins | Cocaine |  |
| Vascular | Hypertension | Primary, secondary |  |
|  | Decompression sickness |  |  |
|  | Fibromuscular hyperplasia |  |  |
|  | Aneurysm | Dissecting, ruptured, enlarging |  |
| Lungs | Obstructive | Asthma |  |
|  |  | Chronic bronchitis, Emphysema and airway obstruction |  |
|  | Ischemic lung disease | Pulmonary embolism, Pulmonary thrombosis, Fat embolism |  |
|  | Environmental lung diseases |  |  |
|  | Ischemic lung disease | Pulmonary embolism Pulmonary thrombosis |  |
|  | Interstitial lung disease | Idiopathic pulmonary fibrosis |  |
|  | Congenital | Cystic fibrosis |  |
|  | Cor pulmonale |  |  |
|  | Trauma |  |  |
|  | Pneumonia and pneumonitides | Infectious, parasitic, toxic, traumatic, burn, aspiration |  |
|  | Sarcoidosis |  |  |
| Pancreas | Endocrine | Diabetes mellitus, type I and II | Beta cell failure, dysfunction |
|  |  |  | Diabetic neuropathy |
|  |  | Other endocrine cell failure of the pancreas |  |
|  | Exocrine | Exocrine pancreas failure | Pancreatitis |
| Bone | Osteopenia | Primary | Hypogonadism |
|  |  | secondary | immobilisation |
|  |  |  | Postmenopausal |
|  |  |  | Age-related |
|  |  |  | Hyperparathyroidism |
|  |  |  | Hyperthyroidism |
|  |  |  | Calcium, magnesium, phosphorus and/or vitamin D deficiency |
|  | Osteomyelitis |  |  |
|  | Avascular necrosis |  |  |
|  | Trauma |  |  |
|  | Paget's disease |  |  |

-continued

| Cell, tissue or organ | Dysfunction or pathology | Condition or disease | Type |
|---|---|---|---|
| Skin | Alopecia | Areata | Primary |
| | | Totalis | Secondary |
| | | | Male pattern baldness |
| | Vitiligo | Localized | Primary |
| | | Generalized | Secondary |
| | Diabetic ulceration | | |
| | Peripheral vascular disease | | |
| | Burn injuries | | |
| Autoimmune disorders | Lupus erythematodes, Sjiogren, Rheumatoid arthritis, Glomerulonephritis, Angiitis | | |
| | Langerhan's histiocytosis | | |
| Eye | Optic neuritis | | |
| | Blunt and penetrating injuries, Infections, Sarcoid, Sickle C disease, Retinal detachment, Temporal arteritis | | |
| | Retinal ischemia, macular degeneration, retinal detachment, retinitis pigmentosa, arteriosclerotic retinopathy, hypertensive retinopathy, retinal artery blockage, retinal vein blockage, hypotension, and diabetic retinopathy. | | |
| Embryonic and fetal disorders | Asphyxia | | |
| | Ischemia | | |
| CNS | Chronic fatigue syndrome, acute and chronic hypoosmolar and hyperosmolar syndromes, AIDS Dementia, Electrocution | | |
| | Encephalitis | Rabies, Herpes | |
| | Meningitis | | |
| | Subdural hematoma | | |
| | Nicotine addiction | | |
| | Drug abuse and withdrawal | Cocaine, heroin, crack, marijuana, LSD, PCP, poly-drug abuse, ecstasy, opioids, sedative hypnotics, amphetamines, caffeine | |
| | Obsessive-compulsive disorders | | |
| | Spinal stenosis, Transverse myelitis, Guillian Barre, Trauma, Nerve root compression, Tumoral compression, Heat stroke | | |
| ENT | Tinnitus | | |
| | Meuniere's syndrome | | |
| | Hearing loss | | |
| | Traumatic injury, barotrauma | | |
| Kidney | Renal failure | Acute, chronic | Vascular/ischemic, interstitial disease, diabetic kidney disease, nephrotic syndromes, infections |
| | Henoch S. Purpura | | |
| Striated muscle | Autoimmune disorders | Myasthenia gravis | |
| | | Dermatomyositis | |
| | | Polymyositis | |
| | Myopathies | Inherited metabolic, endocrine and toxic | |
| | Heat stroke | | |
| | Crush injury | | |
| | Rhabdomylosis | | |
| | Mitochondrial disease | | |
| | Infection | Necrotizing fasciitis | |

| Cell, tissue or organ | Dysfunction or pathology | Condition or disease | Type |
|---|---|---|---|
| Sexual dysfunction | Central and peripheral | Impotence secondary to medication | |
| Liver | Hepatitis<br>Ischemic disease<br>Cirrhosis, fatty liver<br>Infiltrative/metabolic diseases | Viral, bacterial, parasitic | |
| Gastrointestinal | Ischemic bowel disease<br>Inflammatory bowel disease<br>Necrotizing enterocolitis | | |
| Organ transplantation | Treatment of donor and recipient | | |
| Reproductive tract | Infertility | Vascular<br>Autoimmune<br>Uterine abnormalities<br>Implantation disorders | |
| Endocrine | Glandular hyper- and hypofunction | | |

As mentioned above, these diseases, disorders or conditions are merely illustrative of the range of benefits provided by the tissue protective cytokines of the invention. Accordingly, this invention generally provides therapeutic or prophylactic treatment of the consequences of mechanical trauma or of human diseases. Therapeutic or prophylactic treatment for diseases, disorders or conditions of the CNS and/or peripheral nervous system are preferred. Therapeutic or prophylactic treatment for diseases, disorders or conditions which have a psychiatric component is provided. Therapeutic or prophylactic treatment for diseases, disorders or conditions including but not limited to those having an ophthalmic, cardiovascular, cardiopulmonary, respiratory, kidney, urinary, reproductive, gastrointestinal, endocrine, or metabolic component is provided.

One of ordinary skill in the art would understand that the pharmaceutical composition of the present invention may be made of a mixture of the tissue protective cytokines of the present invention as well as erythropoietin.

In one embodiment, such a pharmaceutical composition of erythropoietin or tissue protective cytokine may be administered systemically to protect or enhance the target cells, tissue or organ. Such administration may be parenterally, via inhalation, or transmucosally, e.g., orally, nasally, rectally, intravaginally, sublingually, submucosally or transdermally. Preferably, administration is parenteral, e.g., via intravenous or intraperitoneal injection, and also including, but is not limited to, intra-arterial, intramuscular, intradermal and subcutaneous administration.

For other routes of administration, such as by use of a perfusate, injection into an organ, or other local administration, a pharmaceutical composition will be provided which results in similar levels of a tissue protective cytokine as described above. A level of about 15 pM-30 nM is preferred.

The pharmaceutical compositions of the invention may comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized foreign pharmacopeia for use in animals, and more particularly in humans. The term "carrier" refers to a diluent, adjuvant, excipient, or vehicle with which the therapeutic is administered. Such pharmaceutical carriers can be sterile liquids, such as saline solutions in water and oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

Pharmaceutical compositions adapted for oral administration may be provided as capsules or tablets; as powders or granules; as solutions, syrups or suspensions (in aqueous or non-aqueous liquids); as edible foams or whips; or as emulsions. Tablets or hard gelatine capsules may comprise lactose, starch or derivatives thereof, magnesium stearate, sodium saccharine, cellulose, magnesium carbonate, stearic acid or salts thereof. Soft gelatine capsules may comprise vegetable oils, waxes, fats, semi-solid, or liquid polyols etc. Solutions and syrups may comprise water, polyols and sugars.

An active agent intended for oral administration may be coated with or admixed with a material that delays disintegration and/or absorption of the active agent in the gastrointestinal tract (e.g., glyceryl monostearate or glyceryl distearate may be used). Thus, the sustained release of an active agent may be achieved over many hours and, if necessary, the active agent can be protected from being degraded within the stomach. Pharmaceutical compositions for oral administration may be formulated to facilitate release of an active agent at a particular gastrointestinal location due to specific pH or enzymatic conditions.

Pharmaceutical compositions adapted for transdermal administration may be provided as discrete patches intended to remain in intimate contact with the epidermis of the recipient for a prolonged period of time. Pharmaceutical compositions adapted for topical administration may be provided as ointments, creams, suspensions, lotions, powders, solutions, pastes, gels, sprays, aerosols or oils. For topical administration to the skin, mouth, eye or other external tissues a topical ointment or cream is preferably used. When formulated in an ointment, the active ingredient may be employed with either a paraffinic or a water-miscible ointment base. Alternatively, the active ingredient may be formulated in a cream with an oil-in-water base or a water-in-oil base. Pharmaceutical compositions adapted for topical administration to the eye include eye drops. In these compositions, the active ingredient can be dissolved or suspended in a suitable carrier, e.g., in an aqueous solvent. Pharmaceutical compositions adapted for topical administration in the mouth include lozenges, pastilles and mouthwashes.

Pharmaceutical compositions adapted for nasal and pulmonary administration may comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, compositions adopted for nasal administration may comprise liquid carriers, e.g., nasal sprays or nasal drops. Alternatively, inhalation of compounds directly into the lungs may be accomplished by inhalation deeply or installation through a mouthpiece into the oropharynx. These compositions may comprise aqueous or oil solutions of the active ingredient. Compositions for administration by inhalation may be supplied in specially adapted devices including, but not limited to, pressurized aerosols, nebulizers or insufflators, which can be constructed so as to provide predetermined dosages of the active ingredient. In a preferred embodiment, pharmaceutical compositions of the invention are administered into the nasal cavity directly or into the lungs via the nasal cavity or oropharynx.

Pharmaceutical compositions adapted for rectal administration may be provided as suppositories or enemas. Pharmaceutical compositions adapted for vaginal administration may be provided as pessaries, tampons, creams, gels, pastes, foams or spray formulations.

Pharmaceutical compositions adapted for parenteral administration include aqueous and non-aqueous sterile injectable solutions or suspensions, which may contain antioxidants, buffers, bacteriostats and solutes that render the compositions substantially isotonic with the blood of an intended recipient. Other components that may be present in such compositions include water, alcohols, polyols, glycerine and vegetable oils, for example. Compositions adapted for parenteral administration may be presented in unit-dose or multi-dose containers, for example sealed ampules and vials, and may be stored in a freeze-dried (lyophilized) condition requiring only the addition of a sterile liquid carrier, e.g., sterile saline solution for injections, immediately prior to use. Extemporaneous injection solutions and suspensions may be prepared from sterile powders, granules and tablets. In one embodiment, an autoinjector comprising an injectable solution of an erythropoietin may be provided for emergency use by ambulances, emergency rooms, and battlefield situations, and even for self-administration in a domestic setting, particularly where the possibility of traumatic amputation may occur, such as by imprudent use of a lawn mower. The likelihood that cells and tissues in a severed foot or toe will survive after reattachment may be increased by administering erythropoietin or a tissue protective cytokine to multiple sites in the severed part as soon as practicable, even before the arrival of medical personnel on site, or arrival of the afflicted individual with severed toe in tow at the emergency room.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically-sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile saline can be provided so that the ingredients may be mixed prior to administration.

Suppositories generally contain active ingredient in the range of 0.5% to 10% by weight; oral formulations preferably contain 10% to 95% active ingredient.

A perfusate composition may be provided for use in transplanted organ baths, for in situ perfusion, or for administration to the vasculature of an organ donor prior to organ harvesting. Such pharmaceutical compositions may comprise levels of erythropoietin, tissue protective cytokines, or a form of either erythropoietin or tissue protective cytokines not suitable for acute or chronic, local or systemic administration to an individual, but will serve the functions intended herein in a cadaver, organ bath, organ perfusate, or in situ perfusate prior to removing or reducing the levels of the erythropoietin contained therein before exposing or returning the treated organ or tissue to regular circulation. The erythropoietin for this aspect of the invention may be any erythropoietin, such as naturally-occurring forms such as human erythropoietin, or any of tissue protective cytokines hereinabove described, such as asialoerythropoietin and phenylglyoxal-erythropoietins, as non-limiting examples.

The present invention provides pharmaceuitical compositions for the treatment, prophylaxis, and amelioration of one or more symptoms associated with inflammation. In a specific embodiment, a composition comprises one or more tissue protective cytokines. In another embodiment, a composition comprises one or more tissue protective cytokines and one or more prophylactic or therapeutic agents other than tissue protective cytokines, said prophylactic or therapeutic agents known to be useful for, or having been or currently being used in the prevention, treatment or amelioration of one or more symptoms associated inflammation.

In a preferred embodiment, a composition of the invention is a pharmaceutical composition. Such compositions comprise a prophylactically or therapeutically effective amount of one or more prophylactic or therapeutic agents (e.g., a tissue protective cytokine or other prophylactic or therapeutic agent), and a pharmaceutically acceptable carrier. In one embodiment, the term "therapeutically effective amount" means including an amount of an agent that is not necessarily effective when the agent is administered alone but is effective when co-administered with another agent.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In particular, the invention provides that one or more of the prophylactic or therapeutic agents, or pharmaceutical compositions of the invention is packaged in a hermetically sealed container such as an ampoule or sachette indicating the quantity of the agent. In one embodiment, one or more of the prophylactic or therapeutic agents, or pharmaceutical compositions of the invention is supplied as a dry sterilized lyophilized powder or water free concentrate in a hermetically sealed container and can be reconstituted, e.g., with water or saline to the appropriate concentration for administration to a subject. Preferably, one or more of the prophylactic or therapeutic agents, or pharmaceutical compositions of the invention is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, at least 75 mg, or at least 100 mg. The lyophilized prophylactic or therapeutic agents, or pharmaceutical compositions of the invention should be stored at between 2 and 8° C. in its original container and the prophylactic or therapeutic agents, or pharmaceutical compositions of the invention should be administered within 1 week, preferably within 5 days, within 72 hours, within 48 hours, within 24 hours, within 12 hours, within 6 hours, within 5 hours, within 3 hours, or within 1 hour after being reconstituted. In an alternative embodiment, one or more of the prophylactic or therapeutic agents, or pharmaceutical compositions of the invention is supplied in liquid form in a hermetically sealed container indicating the quantity and concentration of the agent. Preferably, the liquid form of the administered composition is supplied in a hermetically sealed container at least 0.25 mg/ml, more preferably at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml or at least 100 mg/ml. The liquid form should be stored at between 2° C. and 8° C. in its original container.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

Generally, the ingredients of the compositions of the invention are derived from a subject that is the same species origin or species reactivity as recipient of such compositions. Thus, in a preferred embodiment, human or humanized antibodies are administered to a human for therapy or prophylaxis.

In another embodiment, for example, a tissue protective cytokine can be delivered in a controlled-release system. For example, the polypeptide may be administered using intravenous infusion, an implantable osmotic pump, a transdermal patch, liposomes, or other modes of administration. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, the compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); WO 91/04014; U.S. Pat. No. 4,704,355; Lopez-Berestein, ibid., pp. 317-327; see generally ibid.). In another embodiment, polymeric materials can be used (see Medical Applications of Controlled Release, Langer and Wise (eds.), CRC Press: Boca Raton, Fla., 1974; Controlled Drug Bioavailability, Drug Product Design and Performance, Smolen and Ball (eds.), Wiley: New York (1984); Ranger and Peppas, J. Macromol. Sci. Rev. Macromol. Chem. 23:61, 1953; see also Levy et al., 1985, Science 228:190; During et al., 1989, Ann. Neurol. 25:351; Howard et al., 1989, J. Neurosurg. 71:105).

In yet another embodiment, a controlled release system can be placed in proximity of the therapeutic target, i.e., the target cells, tissue or organ, thus requiring only a fraction of the systemic dose (see, e.g., Goodson, pp. 115-138 in Medical Applications of Controlled Release, vol. 2, supra, 1984). Other controlled release systems are discussed in the review by Langer (1990, Science 249:1527-1533).

In another embodiment, a tissue protective cytokine, as properly formulated, can be administered by nasal, oral, rectal, vaginal, or sublingual administration.

In a specific embodiment, it may be desirable to administer erythropoietin and/or the tissue protective cytokines of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or fibers.

Selection of the preferred effective dose will be readily determinable by a skilled artisan based upon considering several factors, which will be known to one of ordinary skill in the art. Such factors include the particular form of erythropoietin or the tissue protective cytokine, and its pharmacokinetic parameters such as bioavailability, metabolism, half-life, etc., which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether administration is acute or chronic, concomitant medications, and other factors well known to affect the efficacy of administered pharmaceutical agents. Thus the precise dosage should be decided according to the judgment of the practitioner and each patient's circumstances, e.g., depending upon the condition and the immune status of the individual patient, and according to standard clinical techniques.

In another aspect of the invention, a perfusate or perfusion solution is provided for perfusion and storage of organs for transplant, the perfusion solution includes an amount of erythropoietin or a tissue protective cytokine effective to protect responsive cells and associated cells, tissues or organs. Transplant includes but is not limited to xenotransplantation, where an organ (including cells, tissue or other bodily part) is harvested from one donor and transplanted into a different recipient; and autotransplant, where the organ is taken from one part of a body and replaced at another, including bench surgical procedures, in which an organ may be removed, and while ex vivo, resected, repaired, or otherwise manipulated, such as for tumor removal, and then returned to the original location. In one embodiment, the perfusion solution is the University of Wisconsin (UW) solution (U.S. Pat. No. 4,798, 824) which contains from about 1 to about 25 U/ml erythropoietin, 5% hydroxyethyl starch (having a molecular weight of from about 200,000 to about 300,000 and substantially free of ethylene glycol, ethylene chorohydrin, sodium chloride and acetone); 25 mM $KH_2PO_4$; 3 mM glutathione; 5 mM adenosine; 10 mM glucose; 10 mM HEPES buffer, 5 mM magnesium gluconate; 1.5 mM $CaCl_2$; 105 mM sodium gluconate; 200,000 units penicillin; 40 units insulin; 16 mg dexamethasone; 12 mg Phenol Red; and has a pH of 7.4-7.5 and an osmolality of about 320 mOsm/l. The solution is used to maintain cadaveric kidneys and pancreases prior to transplant. Using the solution, preservation can be extended beyond the 30-hour limit recommended for cadaveric kidney preservation. This particular perfusate is merely illustrative of a number of such solutions that can be adapted for the present use by inclusion of an effective amount of erythropoietin and/or a tissue protective cytokine. In a further embodiment, the perfusate solution contains from about 1 to about 500 ng/ml erythropoietin, or from about 40 to about 320 ng/ml erythropoietin. As mentioned above, any form of erytiropoietin or tissue protective cytokines can be used in this aspect of the invention.

While the preferred recipient of a tissue protective cytokine for the purposes herein throughout is a human, the methods herein apply equally to other mammals, particularly domesticated animals, livestock, companion, and zoo animals. However, the invention is not so limiting and the benefits can be applied to any mammal.

In further aspects of the e-vivo invention, erythropoietin and any tissue protective cytokine such as but not limited to the ones described above may be employed.

In another aspect of the invention, methods and compositions for enhancing the viability of cells, tissues or organs which are not isolated from the vasculature by an endothelial cell barrier are provided by exposing the cells, tissue or organs directly to a pharmaceutical composition comprising erythropoietin or a tissue protective cytokine, or administering or contacting a pharmaceutical composition containing erythropoietin or a tissue protective cytokine to the vasculature of the tissue or organ. Enhanced activity of responsive cells in the treated tissue or organ is responsible for the positive effects exerted.

As described above, the invention is based, in part, on the discovery that erythropoietin molecules can be transported from the luminal surface to the basement membrane surface of endothelial cells of the capillaries of organs with endothelial cell tight junctions, including, for example, the brain, retina, and testis. Thus, responsive cells across the barrier are susceptible targets for the beneficial effects of erythropoietin or tissue protective cytokines, and others cell types or tissues or organs that contain and depend in whole or in part on responsive cells therein are targets for the methods of the invention. While not wishing to be bound by any particular theory, after transcytosis of erythropoietin or the tissue protective cytokine, erythropoietin or the tissue protective cytokine can interact with an erythropoietin receptor on a responsive cell, for example, neuronal, retinal, muscle, heart, lung, liver, kidney, small intestine, adrenal cortex, adrenal medulla, capillary endothelial, testes, ovary, or endometrial cell, and receptor binding can initiate a signal transduction cascade resulting in the activation of a gene expression program within the responsive cell or tissue, resulting in the protection of the cell or tissue, or organ, from damage, such as by toxins, chemotherapeutic agents, radiation therapy, hypoxia, etc. Thus, methods for protecting responsive cell-containing tissue from injury or hypoxic stress, and enhancing the function of such tissue are described in detail herein below.

In the practice of one embodiment of the invention, a mammalian patient is undergoing systemic chemotherapy for cancer treatment, including radiation therapy, which commonly has adverse effects such as nerve, lung, heart, ovarian or testicular damage. Administration of a pharmaceutical composition comprising erythropoietin and/or a tissue protective cytokine as described above is performed prior to and during chemotherapy and/or radiation therapy, to protect various tissues and organs from damage by the chemotherapeutic agent, such as to protect the testes. Treatment may be continued until circulating levels of the chemotherapeutic agent have fallen below a level of potential danger to the mammalian body.

In the practice of another embodiment of the invention, various organs were planned to be harvested from a victim of an automobile accident for transplant into a number of recipients, some of which required transport for an extended distance and period of time. Prior to organ harvesting, the victim was infused with a pharmaceutical composition comprising erythropoietin and/or tissue protective cytokines as described herein. Harvested organs for shipment were perfused with a perfusate containing erythropoietin and/or tissue protective cytokines as described herein, and stored in a bath comprising erythropoietin and/or tissue protective cytokines. Certain organs were continuously perfused with a pulsatile perfusion device, utilizing a perfilsate containing erythropoietin and/or tissue protective cytokines in accordance with the present invention. Minimal deterioration of organ function occurred during the transport and upon implant and reperfilsion of the organs in situ.

In another embodiment of the invention, a surgical procedure to repair a heart valve required temporary cardioplegia and arterial occlusion. Prior to surgery, the patient was infused with a tissue protective cytokine, 4 µg of carbamylated asialoerythropoietin per kg body weight. Such treatment prevented hypoxic ischemic cellular damage, particularly after yeperfusion.

In another embodiment of the invention, in any surgical procedure, such as in cardiopulmonary bypass surgery, a naturally-occurring erythropoietin or a tissue protective cytokine of the invention can be used. In one embodiment, administration of a pharmaceutical composition comprising erythropoietin and/or tissue protective cytokines as described above is performed prior to, during, and/or following the bypass procedure, to protect the function of brain, heart, and other organs.

In the foregoing examples in which naturally-occurring erythropoietin and/or a tissue protective cytokine of the invention is used for ex-vivo applications, or to treat responsive cells such as neuronal tissue, retinal tissue, heart, lung, liver, kidney, small intestine, adrenal cortex, adrenal medulla, capillary endothelial, testes, ovary, or endometrial cells or tissue, the invention provides a pharmaceutical composition in dosage unit form adapted for protection or enhancement of responsive cells, tissues or organs distal to the vasculature which comprises an amount within the range from about 1 pg to 5 mg, 500 pg to 5mg, 1 ng to 5 mg, 500 ng to 5 mg, 1 µg to 5 mg, 500 µg to 5 mg, or 1 mg to 5 mg of a tissue protective cytokine, and a pharmaceutically acceptable carrier. In a preferred embodiment, the amount of tissue protective cytokine is within the range from about 1 pg to 1 mg. In a preferred embodiment, the formulation contains tissue protective cytokines that are non-erythropoietic.

In a further aspect of the invention, administration of tissue protective cytokines was found to restore cognitive function in animals having undergone brain trauma. After a delay of either 5 days or 30 days, administration of erythropoietin was still able to restore function as compared to sham-treated animals, indicating the ability of an erythropoietin to regenerate or restore brain activity. Thus, the invention is also directed to the use of erythropoietin and/or tissue protective cytokines for the preparation of a pharmaceutical composition for the treatment of brain trauma and other cognitive dysfunctions, including treatment well after the injury (e.g. three days, five days, a week, a month, or longer). The invention is also directed to a method for the treatment of cognitive dysfumction following injury by administering an effective amount of erythropoietin and/or tissue protective cytokines. Any erythropoietin and/or tissue protective cytokine as described herein may be used for this aspect of the invention.

Furthermore, this restorative aspect of the invention is directed to the use of any erythropoietins and/or tissue protective cytokines herein for the preparation of a pharmaceutical composition for the restoration of cellular, tissue or organ dysfunction, wherein treatment is initiated after, and well after, the initial insult responsible for the dysfunction. Moreover, treatment using erythropoietin and/or tissue protective cytokines of the invention can span the course of the disease or condition during the acute phase as well as a chronic phase.

In the instance wherein an erythropoietin of the invention has erythropoietic activity, in a preferred embodiment, erythropoietin may be administered systemically at a dosage between about 1 µg and about 100 µg/kg body weight, preferably about 5 -50 µg/kg-body weight, most preferably about 10-30 µg/kg-body weight, per administration. This effective dose should be sufficient to achieve serum levels of erythropoietin greater than about 10,000, 15,000, or 20,600 mU/ml (80, 120, or 160 ng/ml) of serum after erythropoietin administration. Such serum levels may be achieved at about 1, 2, 3, 4, 5, 6, 7, 8, 9, or 10 hours post-administration. Such dosages may be repeated as necessary. For example, administration may be repeated daily, as long as clinically necessary, or after an appropriate interval, e.g., every 1 to 12 weeks, preferably, every 1 to 3 weeks. In one embodiment, the effective amount of erythropoietin and a pharmaceutically acceptable carrier may be packaged in a single dose vial or other container. In another embodiment, the tissue protective cytokines, which are capable of exerting the activities described herein but not causing an increase in hemoglobin concentration or hematocrit, are used. Such tissue protective cytokines are preferred in instances wherein the methods of the present invention are intended to be provided chronically. In another embodiment, an erythropoietin is given at a dose greater than that necessary to maximally stimulate erythropoiesis. As noted above, a tissue protective cytokine of the invention does not necessarily have erythropoietic activity, and therefore the above dosages expressed in hematopoietic units are merely exemplary for erythropoietins that are erythropoietic; hereinabove weight equivalents for dosages are provided which are applicable to tissue protective cytokines.

In one embodiment, the amount of the composition of the invention which will be effective in the treatment, prevention or amelioration of one or more symptoms associated with inflammation can be determined by standard clinical techniques. The precise dose to be employed in the formulation will also depend on the route of administration, and the seriousness of the condition, and should be decided according to the judgment of the practitioner and each mammal's circumstances. Effective doses may be extrapolated from dose-response curves derived from in vitro or animal model test systems.

In a specific embodiment, the dosage of the composition of the invention or a prophylactic or therapeutic agent administered to prevent, treat or ameliorate one or more symptoms associated with an inflammatory disorder in a mammal is 150 µg/kg or less, preferably 125 µg/kg or less, 100 µg/kg or less, 95 µg/kg or less, 90 µg/kg or less, 85 µg/kg or less, 80 µg/kg or less, 75 µg/kg or less, 70 µg/kg or less, 65 µg/kg or less, 60 µg/kg or less, 55 µg/kg or less, 50/µg/kg or less, 45 µg/kg or less, 40 µg/kg or less, 35 µg/kg or less, 30 µg/kg or less, 25 µg/kg or less, 20 µg/kg or less, 15 µg/kg or less, 10 µg/kg or less, 5 µg/kg or less, 2.5 µg/kg or less, 2 µg/kg or less, 1.5 µg/kg or less, 1 µg/kg or less, 0.5 µg/kg or less, or 0.5 µg/kg or less of a mammal's body weight. In another embodiment, the dosage of the composition of the invention or a prophylactic or therapeutic agent administered to prevent, treat or ameliorate one or more symptoms associated with inflammation in a mammal is a unit dose of 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7m g, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

In yet another embodiment, a subject is administered one or more doses of a prophylactically or therapeutically effective amount of one or more immunomodulatory agents, wherein the dose of a prophylactically or therapeutically effective amount of said agent(s) administered to said subject achieves in said subject a mean absolute lymphocyte count of approximately 500 cells/mm$^3$ to below 1500 cells/mm$^3$, preferably below 1400 cells/mm$^3$, below 1300 cells/mm$^3$, below 1250 cells/mm$^3$, below 1200 cells/mm$^3$, below 1100 cells/mm$^3$ or below 1000 cell/mm$^3$/mm$^3$.

The present invention is further directed to a method for facilitating the transport of a molecule across an endothelial cell barrier in a mammal by administering a composition which comprises the particular molecule in association with an erythropoietin or tissue protective cytokine as described hereinabove. As described above, tight junctions between endothelial cells in certain organs in the body create a barrier to the entry of certain molecules. For treatment of various conditions within the barriered organ, means for facilitating passage of pharmaceutical agents is desired. Erythropoietin or tissue protective cytokines of the invention are useful as carriers for delivering other molecules across the blood-brain and other similar barriers. A composition comprising a molecule desirous of crossing the barrier with erythropoietin or a tissue protective cytokine is prepared and peripheral administration of the composition results in the transcytosis of the composition across the barrier. The association between the molecule to be transported across the barrier and the erythropoietin or tissue protective cytokine may be a labile covalent bond, in which case the molecule is released from association with the erythropoietin or tissue protective cytokine after crossing the barrier. If the desired pharmacological activity of the molecule is maintained or unaffected by association with erythropoietin and or tissue protective cytokine, such a complex can be administered.

The skilled artisan will be aware of various means for associating molecules with erythropoietin or a tissue protective cytokine of the invention and the other agents described above, by covalent, non-covalent, and other means. Furthermore, evaluation of the efficacy of the composition can be readily determined in an experimental system. Association of molecules with erythropoietin or a tissue protective cytokine may be achieved by any number of means, including labile, covalent binding, cross-linking, etc. Biotin/avidin interactions may be employed; for example, a biotinylated erythropoietin of the invention may be complexed with a labile conjugate of avidin and a molecule desirably transported. As mentioned above, a hybrid molecule may be prepared by recombinant or synthetic means, for example, a fusion or chimeric polypeptide which includes both the domain of the molecule with desired pharmacological activity and the domain responsible for erythropoietin receptor activity modulation. Protease cleavage sites may be included in the molecule.

A molecule may be conjugated to erythropoietin or a tissue protective cytokine of the invention through a polyfunctional molecule, i. e., a polyfunctional crosslinker. As used herein, the term "polyfunctional molecule" encompasses molecules having one functional group that can react more than one time in succession, such as formaldehyde, as well as molecules with more than one reactive group. As used herein, the term "reactive group" refers to a functional group on the crosslinker that reacts with a functional group on a molecule (e.g., peptide, protein, carbohydrate, nucleic acid, particularly a hormone, antibiotic, or anti-cancer agent to be delivered across an endothelial cell barrier) so as to form a covalent bond between the cross-linker and that molecule. The term "functional group" retains its standard meaning in organic chemistry. The polyfunctional molecules that can be used are preferably biocompatible linkers, i.e., they are noncarcinogenic, nontoxic, and substantially non-immunogenic in vivo. Polyfunctional cross-linkers such as those known in the art and described herein can be readily tested in animal models to determine their biocompatibility. The polyfunctional molecule is preferably bifunctional. As used herein, the term "bifunctional molecule" refers to a molecule with two reactive groups. The bifunctional molecule may be heterobifunctional or homobifunctional. A heterobifunctional cross-linker allows for vectorial conjugation. It is particularly preferred for the polyfunctional molecule to be sufficiently soluble in water for the cross-linking reactions to occur in aqueous solutions such as in aqueous solutions buffered at pH 6 to 8, and for the resulting conjugate to remain water soluble for more effective bio-distribution. Typically, the polyfunctional molecule covalently bonds with an amino or a sulhydryl functional group. However, polyfunctional molecules reactive with other functional groups, such as carboxylic acids or hydroxyl groups, are contemplated in the present invention.

The homobifunctional molecules have at least two reactive functional groups, which are the same. The reactive functional groups on a homobifunctional molecule include, for example, aldehyde groups and active ester groups. Homobifunctional molecules having aldehyde groups include, for example, glutaraldehyde and subaraldehyde. The use of glutaraldehyde as a cross-linking agent was disclosed by Poznansky et al., Science 223, 1304-1306 (1984). Homobifunctional molecules having at least two active ester units include esters of dicarboxylic acids and N-hydroxysuccinimide. Some examples of such N-succinimidyl esters include disuccinimidyl suberate and dithio-bis-(succinimidyl propionate), and their soluble bis-sulfonic acid and bis-sulfonate salts such as their sodium and potassium salts. These homobifunctional reagents are available from Pierce, Rockford, Ill.

The heterobifunctional molecules have at least two different reactive groups. The reactive groups react with different functional groups, e.g., present on the erythropoietin and the molecule. These two different functional groups that react with the reactive group on the heterobifulnctional cross-linker are usually an amino group, e.g., the epsilon amino group of lysine; a sulfhydryl group, e.g., the thiol group of cysteine; a carboxylic acid, e.g., the carboxylate on aspartic acid; or a hydroxyl group, e.g., the hydroxyl group on serine.

Of course, certain of the various tissue protective cytokines of the invention, and erythropoietin, may not have suitable reactive groups available for use with certain cross-linking agent; however, one of skill in the art will be amply aware of the choice of cross-linking agents based on the available groups for cross-linkiing in erythropoietin or tissue protective cytokines of the invention.

When a reactive group of a heterobifuictional molecule forms a covalent bond with an amino group, the covalent bond will usually be an amido or imido bond. The reactive group that forms a covalent bond with an amino group may, for example, be an activated carboxylate group, a halocarbonyl group, or an ester group. The preferred halocarbonyl group is a chlorocarbonyl group. The ester groups are preferably reactive ester groups such as, for example, an N-hydroxy-succinimide ester group.

The other functional group typically is either a thiol group, a group capable of being converted into a thiol group, or a group that forms a covalent bond with a thiol group. The covalent bond will usually be a thioether bond or a disulfide. The reactive group that forms a covalent bond with a thiol group may, for example, be a double bond that reacts with thiol groups or an activated disulfide. A reactive group containing a double bond capable of reacting with a thiol group is the maleimido group, although others, such as acrylonitrile, are also possible. A reactive disulfide group may, for example, be a 2-pyridyldithio group or a 5,5'-dithio-bis-(2-nitrobenzoic acid) group. Some examples of heterobifunctional reagents containing reactive disulfide bonds include N-succinimidyl 3-(2-pyridyl-dithio) propionate (Carlsson, et al., 1978, Biochem J., 173:723-737), sodium S-4-succinrimidyloxycarbonyl-alpha-methylbenzylthiosulfate, and 4-succinimidyloxycarbonyl-alpha-methyl-(2-pyridyldithio)toluene. N-succinimidyl 3-(2-pyridyldithio) propionate is preferred. Some examples of heterobifunctional reagents comprising reactive groups having a double bond that reacts with a thiol group include succinimidyl 4-(N-maleimidomethyl)cyclohexane-1-carboxylate and succinimidyl m-maleimidobenzoate.

Other heterobifunctional molecules include succinimidyl 3-(maleimido) propionate, sulfosuccinimidyl 4-(p-maleimido-phenyl) butyrate, sulfosuccinimidyl 4-(N-maleimidomethyl-cyclohexane)-1-carboxylate, maleimidobenzoyl-N-hydroxy-succinimide ester. The sodium sulfonate salt of succinimidyl m-maleimidobenzoate is preferred. Many of the above-mentioned heterobifunctional reagents and their sulfonate salts are available from Pierce Chemical Co., Rockford, Ill. USA.

The need for the above-described conjugated to be reversible or labile may be readily determined by the skilled artisan. A conjugate may be tested in vitro for both the erythropoietin, and for the desirable pharmacological activity. If the conjugate retains both properties, its suitability may then be tested in vivo. If the conjugated molecule requires separation from erythropoietin or the tissue protective cytokine for activity, a labile bond or reversible association with erythropoietin or the tissue protective cytokine will be preferable. The lability characteristics may also be tested using standard in vitro procedures before in vivo testing.

Additional information regarding how to make and use these as well as other polyfunctional reagents may be obtained from the following publications or others available in the art:

1. Carlsson, 3. et al., 1978, Biochem. J. 173:723-737.
2. Cumber, J. A. et al., 1985, Methods in Enzymology 112:207-224.
3. Jue, R. et al., 1978, Biochem 17:5399-5405.
4. Sun, T. T. et al., 1974, Biochem. 13:2334-2340.
5. Blattler, W. A. et al., 1985, Biochem. 24:1517-152.
6. Liu, F. T. et al., 1979, Biochem. 18:690-697.
7. Youle, R. J. and Neville, D. M. Jr., 1980, Proc. Natl. Acad. Sci. U.S.A. 77:5483-5486.
8. Lerner, R. A. et al., 1981, Proc. Natl. Acad. Sci. U.S.A. 78:3403-3407.
9. Jung, S. M. and Moroi, M., 1983, Biochem. Biophys. Acta 761:162.
10. Caulfield, M. P. et al., 1984, Biochem. 81:7772-7776.
11. Staros, J. V., 1982, Biochem. 21:3950-3955.
12. Yoshitake, S. et al., 1979, Eur. J. Biochem. 101:395-399.
13. Yoshitake, S. et al., 1982, J. Biochem. 92:1413-1424.
14. Pilch, P. F. and Czech, M. P., 1979, J. Biol. Chem. 254:3375-3381.
15. Novick, D. et al., 1987, J. Biol. Chem. 262:8483-8487.
16. Lomant, A. J. and Fairbanks, G., 1976, J. Mol. Biol. 104:243-261.
17. Hamada, H. and Tsuruo, T., 1987, Anal. Biochem. 160:483-488.
18. Hashida, S. et al., 1984, J. Applied Biochem. 6:56-63.

Additionally, methods of cross-linking are reviewed by Means and Feeney, 1990, Bioconjugate Chem. 1:2-12.

Barriers which are crossed by the above-described methods and compositions of the present invention include but are not limited to the blood-brain barrier, the blood-eye barrier, the blood-testes barrier, the blood-ovary barrier, and the blood-uterus barrier.

Candidate molecules for transport across an endothelial cell barrier include, for example, hormones, such as growth hormone, neurotrophic factors, antibiotics, antivirals, or anti-fungals such as those normally excluded from the brain and other barriered organs, peptide radiopharmaceuticals, antisense drugs, antibodies and antivirals against biologically-active agents, pharmaceuticals, and anti-cancer agents. Non-limiting examples of such molecules include hormones such as growth hormone, nerve growth factor (NGF), brain-derived neurotrophic factor (BDNF), ciliary neurotrophic factor (CNTF), basic fibroblast growth factor (bFGF), transforming growth factor β1 (TGFβ1), transforming growth factor β2 (TGFβ2), transforming growth factor β3 (TGFβ3), interleukin 1, interleukin 2, interleukin 3, and interleukin 6, AZT, antibodies against tumor necrosis factor, and immunosuppressive agents such as cyclosporin. Additionally, dyes or markers may be attached to erythropoietin or one of the tissue protective cytokines of the present invention in order to visualize cells, tissues, or organs within the brain and other barriered organs for diagnostic purposes. As an example, a marker used to visualize plaque within the brain could be attached to erythropoietin or a tissue protective cytokine in order to determine the progression of Alzheimer's disease within a patient.

The present invention is also directed to a composition comprising a molecule to be transported via transcytosis across an endothelial cell tight junction barrier and an erythropoietin or tissue protective cytokine as described above. The invention is further directed to the use of a conjugate between a molecule and an erythropoietin or a tissue protective cytokine as described above for the preparation of a pharmaceutical composition for the delivery of the molecule across a barrier as described above.

In the following examples, various animal models and in-vitro tests of neuroprotection and transcytosis are provided to demonstrate the effectiveness of the tissue protective cytokines of the invention. Such models include in vitro models using P-19 cells to determine the neuroprotective affects of the tissue protective cytokines, and in-vivo water intoxication model in mice to determine the in vivo neuroprotective affects of the tissue protective cytokines of the present invention. For transcytosis, model proteins conjugated to the erythropoietins of the invention are evaluated for transport into the brain following parenteral administration. These tests in in-vitro models and animal models are predictive of the efficacy of the present compounds in other mammalian species including humans. Additionally, Example 1, demonstrates that the human brain has an abundance of erythropoietin receptors that provide the mechanism for the transcytosis of erythropoietin as well as tissue protective cytokines.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

Distribution of Erythropoietin Receptor in Human Brain

Normal human brains removed during surgical procedures (e.g., to provide tumor-free margins in tumor resections) were immediately fixed in 5% acrolein in 0.1 M phosphate buffer (pH 7.4) for 3 h. Sections were cut with a vibrating microtome at 40 micrometer thickness. Immunohistochemical staining was performed using free-floating sections and the indirect antibody peroxidase-antiperoxidase method using a 1:500 dilution of erythropoietin receptor antiserum (obtained from Santa Cruz Biotechnology). Endogenous peroxidase activity was quenched by pretreatment of tissue sections with hydrogen peroxide (3% in methanol for 30 min). Tissue controls were also carried out by primary antibody omission and by using the appropriate blocking peptide (from Santa Cruz Biotech.) to confirm that staining was specific for erythropoietin (EPO) receptor.

FIG. 1 shows that capillaries of the human brain express very high levels of EPO receptor, as determined by immunohistochemistry using specific anti-EPO receptor antibodies. This provides a mechanism whereby EPO is able to penetrate into the brain from the systemic circulation, in spite of the blood brain barrier.

Figure 2:
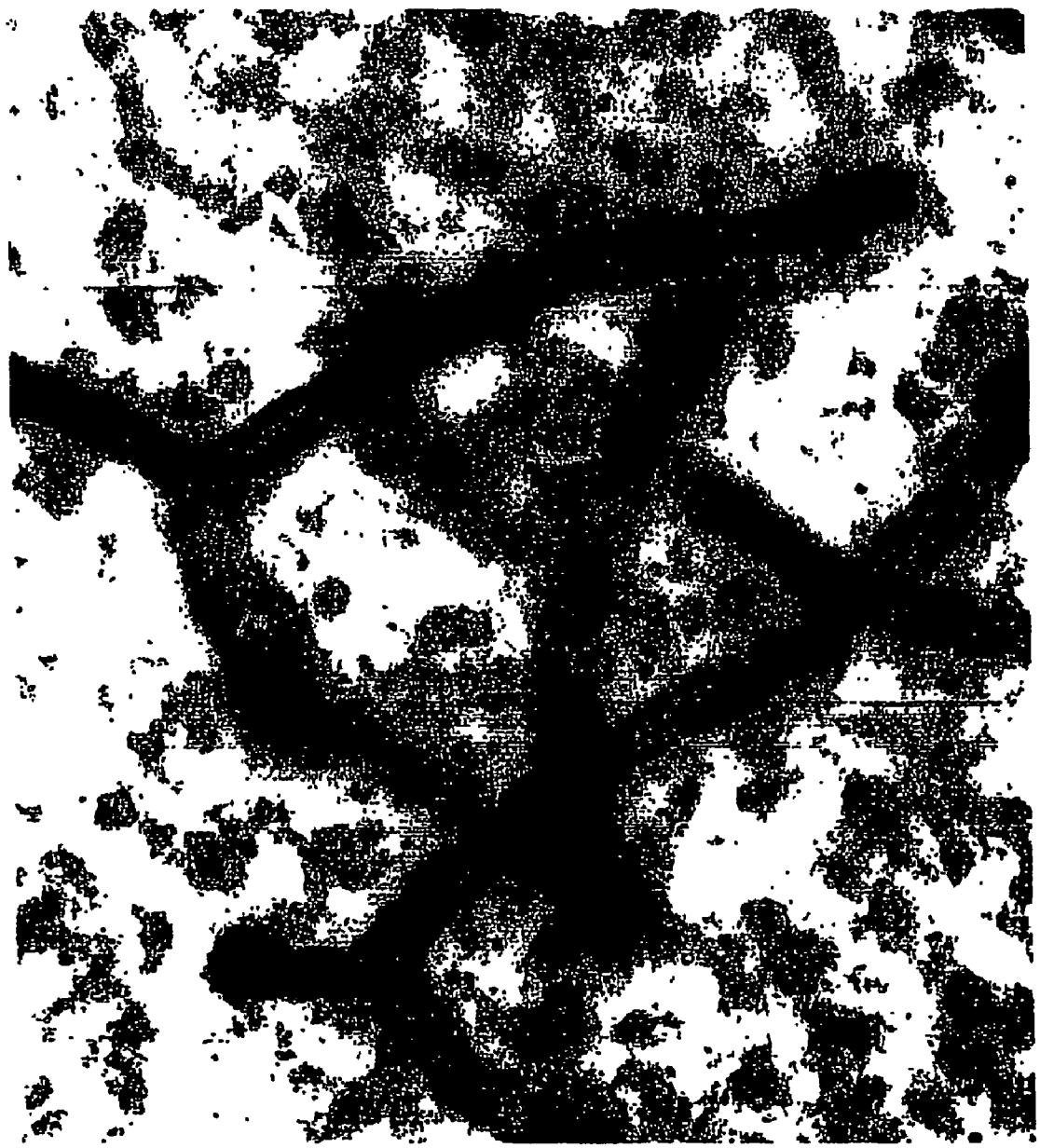
FIG. 2 is a higher power magnification of the image in FIG. 1.

FIG. 2 shows the EPO receptor is densely localized within and around capillaries forming the blood brain barrier in the human brain.

Figure 3:
FIG. 3 shows, using gold-labeled secondary antibodies, the ultramicroscopic distribution of erythropoietin receptors.

A similar protocol as for FIGS. 1 & 2 was performed for FIG. 3, except that 10 micrometer sections were cut from paraffin, the embedded sections fixed by immersion in 4% paraformaldehyde. FIG. 3 shows that there is a high density of EPO receptor at the luminal and anti-luminal surfaces of human brain capillaries, forming the anatomical basis for transport of EPO from the circulation into the brain.

Figure 4:
FIG. 4, prepared similarly to FIG. 3, shows high density erythropoietin receptors at the luminal and anti-luminal surfaces of human brain capillaries.

FIG. 4 was obtained following a similar protocol as in FIG. 3 except that the tissue was sectioned on an ultramicrotome for electron microscopy and the secondary antibody was labeled with colloidal gold particles. This figure shows that EPO receptor is found upon the endothelial surface (*), within cytoplasmic vesicles (arrows) and upon glial endfeet (+) in human brain, providing the anatomical basis for transport of EPO from within the circulation into the brain.

EXAMPLE 2

Tissue Protective Cytokines

Tissue protective cytokines desirable for the uses described herein may be generated by guanidination, carbamylation, amidination, trinitrophenylation, acetylation, succinylation, nitration, or modification of arginine or lysine residues or carboxyl groups, among other procedures as mentioned herein above, of erythropoietin. These modifications produce tissue protective cytokines that maintain their activities for specific organs and tissues but not for others, such as erythrocytes. When erythropoietin is subjected to the above reactions, it has been found that in general the resultant molecule lacks both in-vivo and in-vitro erythropoietic activity (e.g., Satake et al; 1990, *Biochim. Biophys. Acta* 1038:125-9). Some examples of the preparation of tissue protective cytokines are described below. Although the examples below use erythropoietin as the starting material, one of ordinary skill in the art would recognize that erythropoietin derivatives such as desialylated, guanidinated, carbamylated, amidinated, trinitrophenylated, acetylated, succinylated, and nitrated erythropoietin can be used as well.

A. Production of Tissue Protective Cytokines by Desialylating Erythropoietin.

Erythropoietin may be desialylated by the following exemplary procedure. Sialidase (isolatedfrom *Streptococcus* sp 6646K.) is obtained from SELKAGAKU AMERICA (Code No. 120050). Erythropoietin is subjected to desialylation by sialidase (0.05 U/mg EPO) at 37 C for 3 h. The reaction mixture is desalted and concentrated using an Ultrafree Centrifugal Filter Unit. The sample is then applied to an ion exchange column in AKTAprime™ system. The protein is eluted with selected buffers. The eluted fractions containing a significant amount of protein are then subjected to IEF gel analysis. The fractions containing only the top two bands (migrating at pI ~8.5 and ~7.9 on IEF gel) are pooled. The protein content of the pooled fractions was determinned and 1/9 volumes of 10× salt solution (1 M NaCl, 0.2 M sodium citrate, 3 mM citric acid) was added. The sialic acid content of the solution was then determined. No significant sialic content should be detected.

Figure 5:
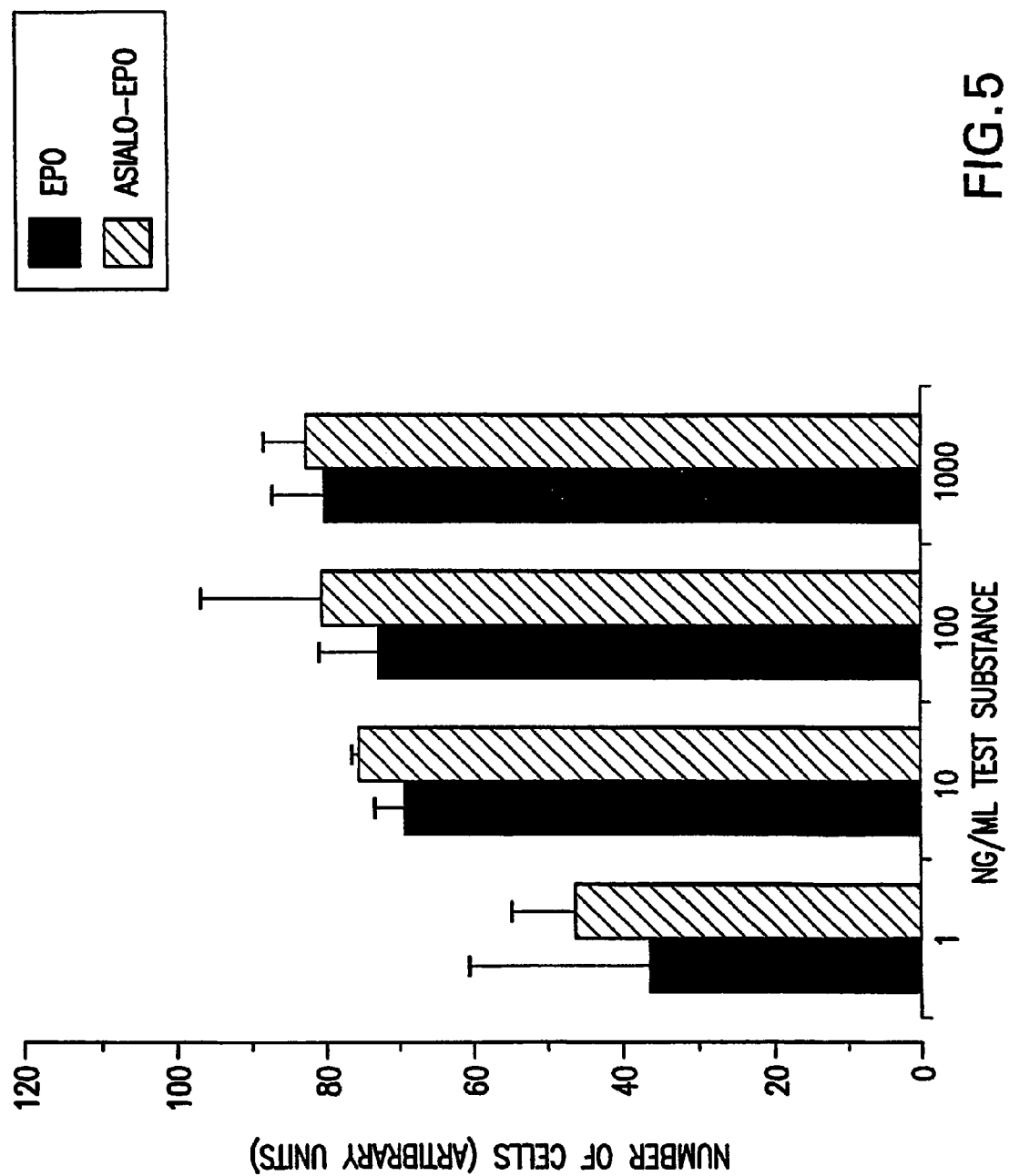
FIG. 5 compares the in-vitro efficacy of erythropoietin and asialoerythropoietin on the viability of serum-starved P19 cells.
Figure 6:
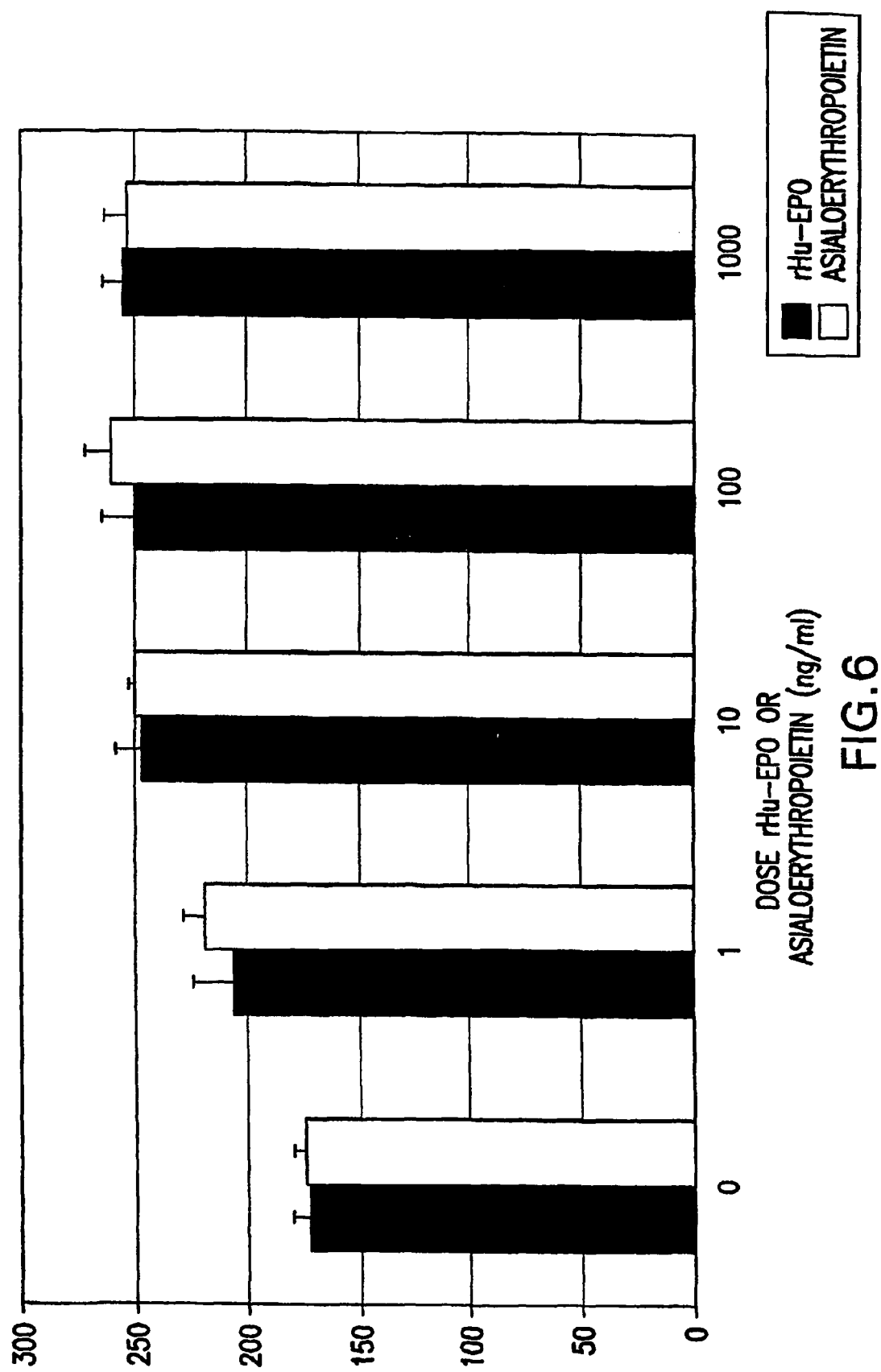
FIG. 6 is another experiment which compares the in-vitro efficacy of erythropoietin and asialoerythropoietin on the viability of serum-starved P19 cells.

Asialoerythropoietin and phenylglyoxalerythropoietin were as effective as native erythropoietin for neural cells in vitro as shown in FIGS. 5-6. In-vitro testing was carried out using neural-like embryonal carcinoma cells (P19) that undergo apoptosis upon the withdrawal of serum. Twenty-four hours before the removal of serum, 1-1000 ng/ml of erythropoietin or a modified erythropoietin was added to the cultures. The following day the medium was removed, the cells washed with fresh, non-serum containing medium, and medium containing the test substance (no serum) added back to the cultures for and additional 48 hours. To determine the number of viable cells, a tetrazolium reduction assay was performed (CellTiter 96; Promega, Inc.). As FIG. 5-6 illustrate, asialoerythropoietin appears to be of equal potency to erythropoietin itself in preventing cell death.

Figure 7:
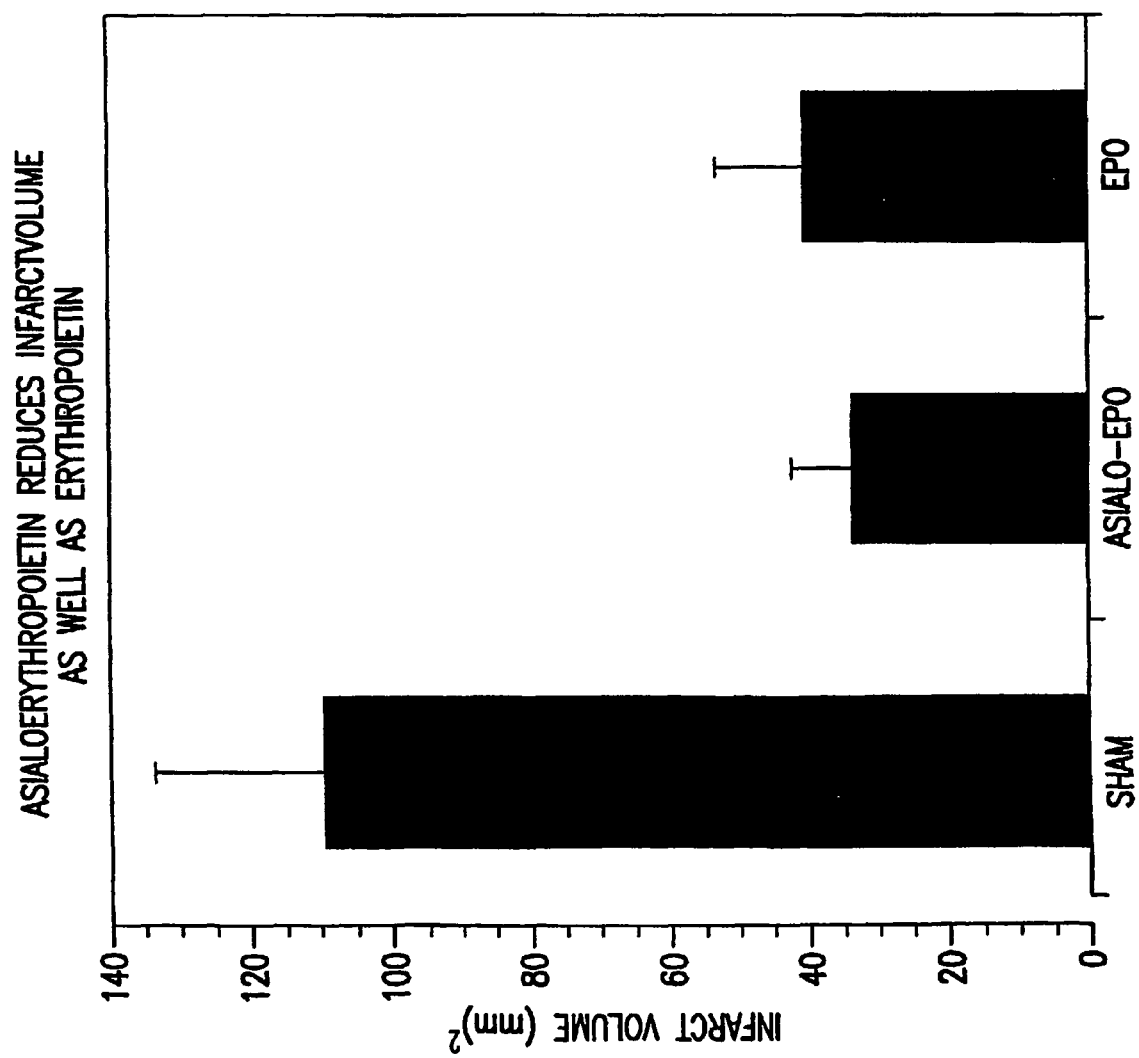
FIG. 7 shows protection of erythropoietin and asialoerythropoietin in a rat focal cerebral ischemia model.
Figure 8:
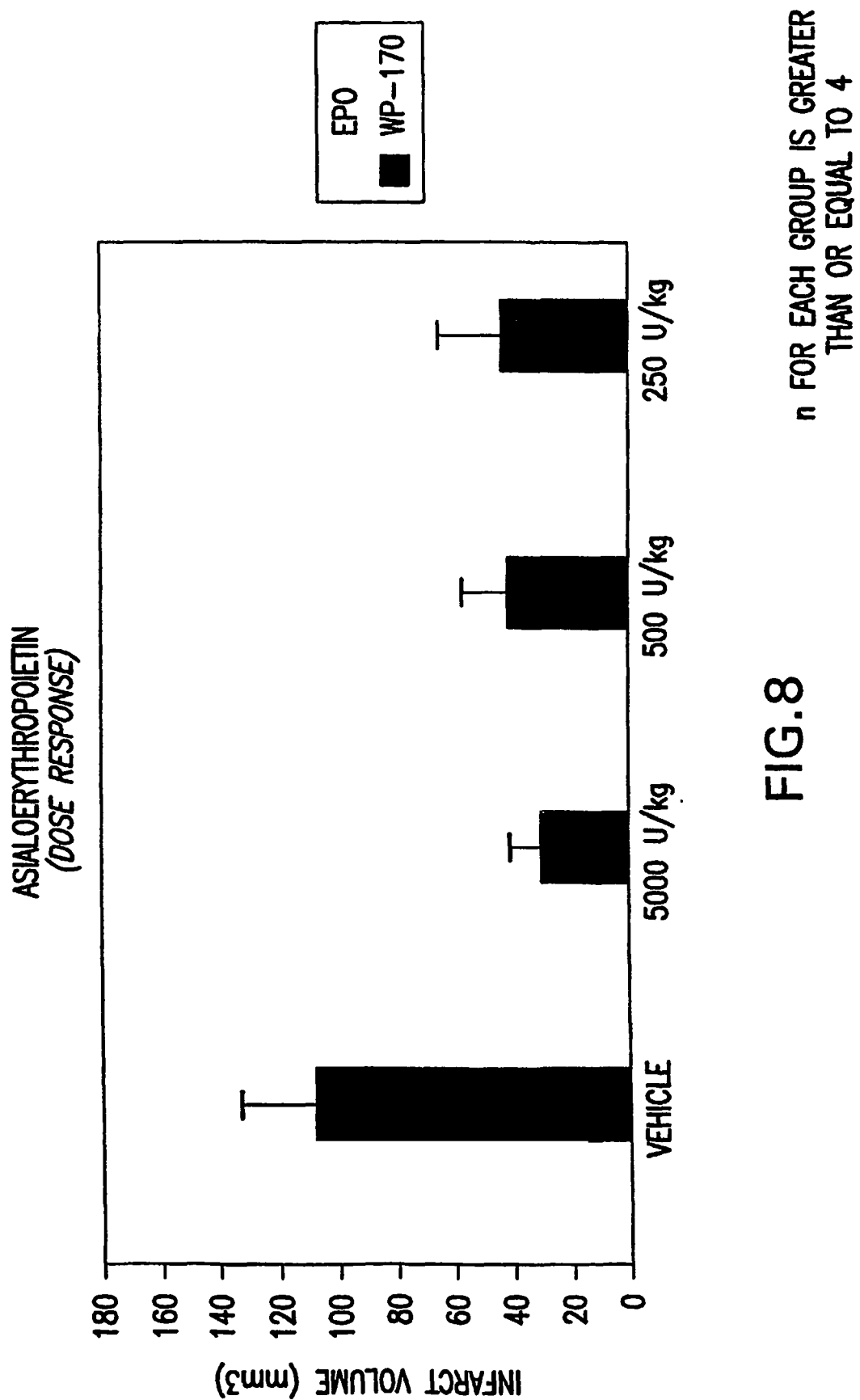
FIG. 8 shows a dose response comparing the efficacy of human erythropoietin and human asialoerythropoietin in middle cerebral artery occlusion in a model of ischermic stroke.

Retention of neuroprotective activity in vivo was confirmed using a rat focal ischemia model in which a reversible lesion in the territory of the middle cerebral artery is performed as described previously (Brines et al., 2000, *Proc. Nat. Acad. Sci. U.S.A.* 97:10526-31). Adult male Sprague-Dawley rats were administered asialoerythropoietin or erythropoietin (5000 U (40 μg)/kgBW intraperitoneally) or vehicle at the onset of the arterial occlusion. Twenty-four hours later, the animals were sacrificed and their brains removed for study. Serial sections were cut and stained with tetrazolium salts to identify living regions of the brain. As shown in FIG. 7, asialoerythropoietin was as effective as native erythropoietin in providing neuroprotection from 1 hour of ischemia FIG. 8 shows the results of another focal ischemia model in which a comparative dose response was performed with erythropoietin and asialoerythropoietin. At the lowest dose of 250 U (2 μg)/kg, asialoerythropoietin afforded protection whereas unmodified erythropoietin did not.

B. Preparation of Tissue Protective Cytokines by Carbamylating Erythropoietin.

Native erythropoietin may be used to prepare the respective carbamylated molecules, in accordance with the following procedure, as described in Jin Zeng (1991). Lysine modification of metallothionein by carbamylation and guanidination. *Methods in Enzymology* 205: 433-437. First, potassium cyanate was recrystallized. A 1 M Borate buffer (pH 8.8) was prepared. An erythropoietin solution was mixed with an equal volume of the borate buffer. Potassium cyanate was added directly to the reaction tube to a final concentration of 0.5 M. The solution was mixed well and incubated at 37 C for 6 h. The solution was then dialyzed thoroughly using distilled water. The product was removed from the dialysis tubing and collected into a fresh tube. The volume was measured and 1/9 volume of 10× salt solution (1 M NaCl, 0.2 M sodium citrate, 3 mM citric acid)is added to the solution. The protein content is determined and the product recovery rate is calculated. The products were analyzed by IEF gel followed by an in vitro test with TF-1 cells.

C. Preparation of Tissue Protective Cytokines by Succinylating Erythropoietin

Native erythropoietin may be used to prepare the respective succinylated molecules, in accordance with the following procedure, as described in Alcalde et al. (2001). Succinylation of cyclodextrin glycosyltransferase from *Thermoanierobacter* sp. 501 enhances its transferase activity using starch as donor. *J. Biotechnology* 86: 71-80. Erythropoietin (100 ug) in 0.5 M NaHCO3 (pH 8.0) was incubated with a 15 molar excess of succinic anhydride at 15 C for 1 hour. The reaction was stopped by dialysis against distilled water.

Another method for succinylating erythropoietin is to dissolve succinic anhydride in dry acetone at 27 mg/ml. The reaction is performed in an eppendorf tube in 10 mM sodium phosphate buffer (pH 8.0). Erythropoietin and 50-fold molar of succinic anhydride are added to the tube. The solution is mixed well and the tube is rotated at 4 C for 1 h. The reaction is stopped by dialysis against 10 mM sodium phosphate buffer, using a Dialysis cassette (Slide-A-Laze 7K, Pierce 66373). The product is removed from the dialysis cassette and collected into a fresh tube. The volume is measured and 1/9 volume of 10× salt solution (1 M NaCl, 0.2 M sodium citrate, 3 mM citric acid) is added. Determine the protein content and calculate the product recovery rate. The products were analyzed by IEF gel followed by an int vitro test with TF-1 cells.

D. Preparation Tissue Protective Cytokine by Acetylating Erythropoietin

Native erythropoietin may be used to prepare the respective acetylated molecules, in accordance with the following procedure, as described in Satake et al (1990). Chemical modification of erythropoietin: an increase in in-vitro activity by guanidination. Biochimica et *Biophysica Acta.* 1038: 125-129.

The reaction was performed in an eppendorf tube in 80 mM sodium phosphate buffer (pH 7.2). Erythropoietin and equal molar of acetic anhydride were added to the tube. After mixing well, the solution was incubated on ice for 1 h. The reaction was stopped by dialysis against water, using a Dialysis cassette (Slide-A-Laze 7K, Pierce 66373). The product was removed from the dialysis cassette and collected into a fresh tube. After measuring the volume of product, 1/9 volume of 10× salt solution (1 M NaCl, 0.2 M sodium citrate, 3 mM citric acid) was added. The protein content is determined, and the product recovery rate was calculated. The product was analyzed by IEF gel followed by an in vitro test with TF-1 cells.

E. Preparation of Tissue Protective Cytokine by Carboxymethylating Lysine of Erythropoietin Native erythropoietin may be used to prepare the respective $N^\epsilon$-(carboxymethyl)lysine (CML) modified molecules in which one or more lysyl residues of the erythropoietin are modified, in accordance with the following procedure, as described in Akhtar et al (1999) Conformational study of $N^\epsilon$-(carboxymethyl)lysine adducts of recombinant a-crystallins. *Current Eye Research,* 18: 270-276.

Glyoxylic acid (200 mM) and NaBH$_3$CN (120 mM) were prepared in sodium phosphate buffer (50 mM, pH 7.5). In an eppendorf tube, erythropoietin was added (in phosphate buffer). The lysine equivalent in the solution (about 8 lysine residues/mol) was then calculated. Next, 3-times greater NaBH$_3$CN and 5 or 10-times greater glyoxylic acid was added to the tube. Each tube was vortexed and incubated at 37 C for 5 h. The samples were dialated against phosphate buffer overnight at 4 C. The volume of each product was measured after dialysis. The protein concentration was determined, and the product recovery rate was calculated. The product was analyzed by IEF gel followed by an in vitro test with TF-1 cells.

F. Preparation of Tissue Protective Cytokine by Iodinating Erythropoietin

Native erythropoietin may be used to prepare the respective iodinated molecules, in accordance with the following procedure, as described in instruction provided by Pierce Chemical Company (Rockford, Ill.) for IODO-Gen Pre-Coated Iodination Tubes (product #28601).

First, 0.1 M of NaI was prepared, and iodination was performed in an IODO-Gen Pre-Coated Iodination Tube (Pierce, 28601), with a total reaction volume of 0.1 ml/tube in sodium phosphate buffer (40 mM, pH 7.4). The protein substrate (erythropoietin) was mixed with sodium phosphate buffer and then transfered to an IODO-Gen Pre-Coated Iodination Tube. NaI was added to a final concentration of 1-2 mM, making the molar ration of NaI/protein as 14-20. The solution was then mixed well and incubated at room temperature for 15 min with gentle agitation. The reaction was stopped by removing the reaction mixture and adding to it a tube containing 3.9 ml of sodium buffer (i.e., a 40-fold dilution). The product was concentrated by a pre-wet Ultrafree centrifugal filter unit. The volume of concentrate was measured and 1/9 volume of 10× salt solution (1 M NaCl, 0.2 M sodium citrate, 3 mM citric acid) was added. The protein concentration was determined, and the product recovery was then calculated. The products were analyzed by IEF gel followed by an in vitro test with TF-1 cells.

Figure 9:
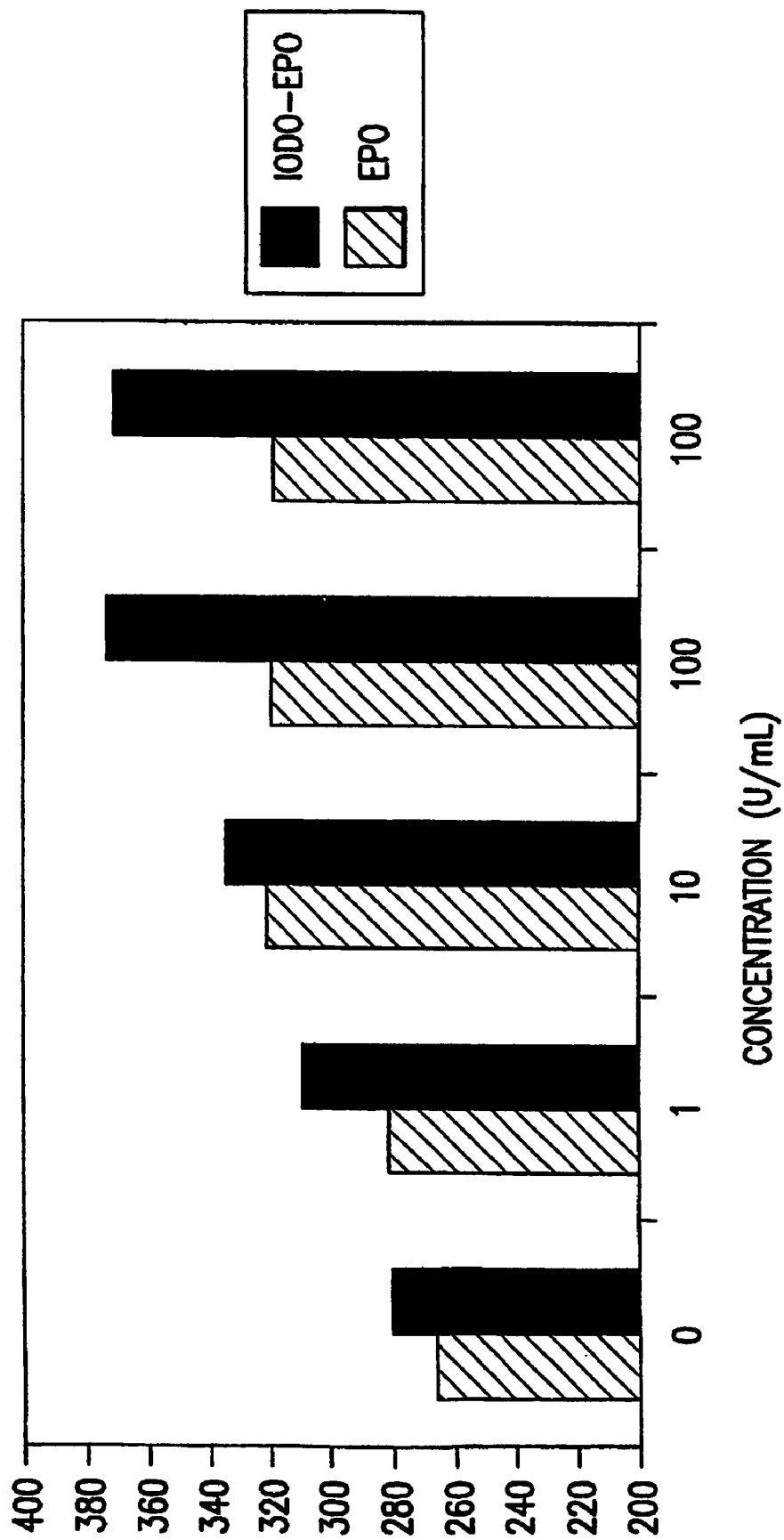
FIG. 9 shows the activity of iodinated erythropoietin in the P19 assay.

2. Another method for iodinating erythropoietin involves incubating one Iodo Bead (Pierce, Rockford, Ill.) in 100 ul PBS (20 mM sodium phosphate, 0.15M NaCl, pH7.5) containing 1 mCi free Na$^{125}$I for 5 minutes. Erythropoietin (100 ug) in 100 ul PBS was then added to the mixture. After a ten minute incubation period at room temperature, the reaction was stopped by removing the 200 ul solution from the reaction vessel (leaving the iodo bead behind). The excess iodine was then removed by gel filtration on a Centricon 10 column. As shown in FIG. 9, iodo-erythropoietin produced in this manner is efficacious in protecting P19 cells from serum withdrawal.

3. Erythropoietin may also be iodinated using Chloramine T. Erythropoietin (100 ug) in 100 ul PBS was added to 500 uCi Na$^{125}$I, and the mixture was then mixed together in an eppendorf tube. 25 ul chloramines T (2 mg/ml) were then added and the mixture was incubated for 1 minute at room temperature. 50 ul of Chloramine T stop buffer (2.4 mg/ml sodium metabisulfite, 10 mg/ml tyrosine, 10% glycerol, 0.1% xylene in PBS was then added. The iodotyrosine and iodinated erythropoietin were then separated by gel filtration on a Centricon 10 column.

Figure 10:
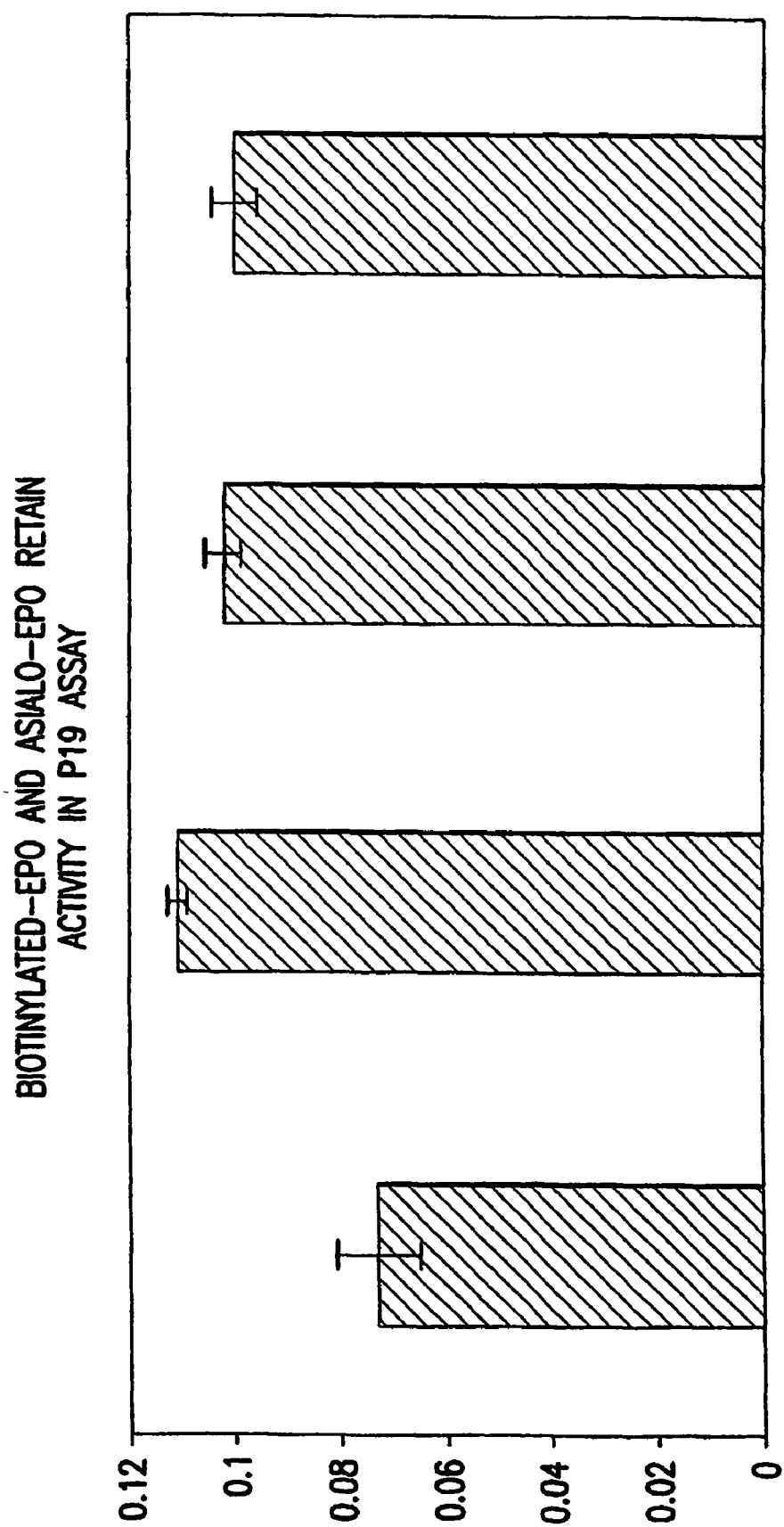
FIG. 10 shows the effect of biotinylated crythropoietin and asialoerythropoietin in the P19 assay.

G. Preparation of Tissue Protective Cytokine by Biotinylating Erythropoietin 1. In "Biotinylated recombinant human erythropoietins: Bioactivity and Utility as a receptor ligand" by Wojchowski et al. Blood, 1989, 74(3):952-8, the authors use three different methods of biotinylating erythropoietin. Biotin is added to (1) the sialic acid moieties (2) carboxylate groups and (3) amino groups. The authors use a mouse spleen cell proliferation assay to demonstrate that (1) the addition of biotin to the sialic acid moieties does not inactivate the biological activity of erythropoietin (2) the addition of biotin to carboxylate groups led to substantial biological inactivation of erythropoietin (3) the addition of biotin to amino groups resulted in complete biological inactivation of erythropoietin. These methods and modifications are fully embraced herein. FIG. 10 shows the activity of biotinylated erythropoietin and asialoerythropoietin in the serum-starved P19 assay.

2. Additionally, native erythropoietin may be used to prepare the respective biotinylated molecules, in accordance with the following procedure, as described in instruction provided by Pierce Chemical Company (Rockford, Ill.) for EZ-Link NHS-LC-Biotin (product #21336).

Immediately before the reaction, EZ-Link NHS-LC-Biotin (pierce, 21336) in DMSO at 2 mg/ml was dissolved. The reaction was performed in a tube (17×100 mm) with total volume of 1 ml containing 50 mM sodium bicarbonate (pH 8.3). Erythropoietin and <10% of EZ-Link NHS-LC-Biotin were added to generate a solution with a molar ratio of Biotin/protein at ~20. The solution was mixed well and incubated on ice for 2 h. The solution was desalted and concentrated using an Ultrafree centrifugal filter unit. The product was then collected into a fresh tube. The volume of the product was measured, and 1/9 volume of 10× salt solution (1 M NaCl, 0.2 M sodium citrate, 3 mM citric acid) was added to the product. The protein content of the product was determined and the product recovery rate was calculated. The products were analyzed by IEF gel followed by an in vitro test with TF-1 cells.

3. The free amino groups of erythropoietin can also be biotinylated using the following method. First, 0.2 mg D-biotinoyl-e-aminocaproic acid-N-hydroxysuccinimide ester (Boehringer Mannheim #1418165) was dissolved in 100 ul DMSO. This solution was then combined with 400 ul PBS containing approximately 0.2 mg erythropoietin in a foil covered tube. After incubating this solution for 4 hours at room temperature, the unreacted biotin was separated by gel filtration on a Centricon 10 column.

It is contemplated that several of these modifications may be performed on erythropoietin or an erythropoietin derivative in order to arrive at a tissue protective cytokine. For example erythropoietin can be desialylated in accordance with the procedure listed above at Example 2(A) and carbamylated in accordance with the procedure listed above at Example 2(B) to generate an asialo carbamoylerythropoietin.

EXAMPLE 3

Preparation of Tissue Protective Cytokines by Other Methods

1. Trinitrophenylation: erythropoietin (100 ug) was modified with 2,4,6-trinitrobenzenesulfonate as described in Plapp et al ("Activity of bovine pancreatic deoxyribonuclease A with modified amino groups" 1971, J. Biol. Chem. 246, 939-845)

2. Arginine modifications: erythropoietin was modified with 2,3 butanedione as described in-Riordan ("Functional arginyl residues in carboxypeptidase A. Modification with butanedione" Riordan J F, Biochemistry 1973, 12(20): 3915-3923).

3. Erythropoietin was modified with cylcohexanone as in Patthy et al ("Identification of functional arginine residues in ribonuclease A and lysozyme" Patthy, L, Smith E L, J. Biol. Chem 1975 250(2): 565-9).

Figure 11:
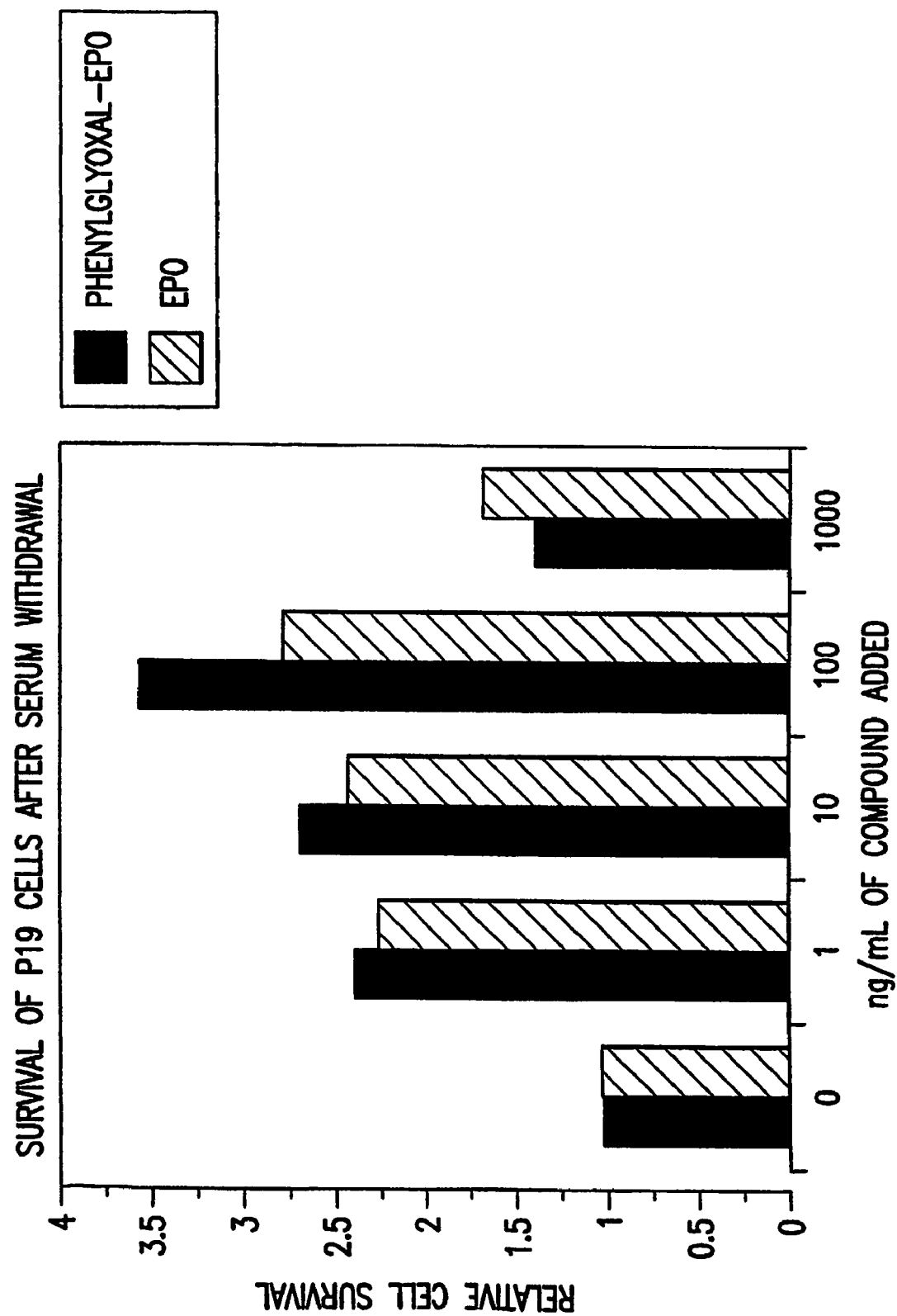
FIG. 11 compares the in-vitro efficacy of erythropoietin and phenylglyoxal-modified erythropoietin on the viability of senum-starved P19 cells.

4. Erythropoietin was modified with phenylglyoxal as described in Werber et al. ("Proceedings: Carboxypeptidase B: modification of functional arginyl residues" Werber, MM, Sokolovsky M Isr J Med Sci 1975 11(11): 1169-70). The phenylglyoxal-modified erythropoietin was tested using the neural-like P19 cell assay described above. As FIG. 11 illustrates, this chemically-modified erythropoietin fully retains its neuroprotective effects.

5. Tyrosine modifications: erythropoietin (100 ug) was incubated with tetranitromethane as previously described in Nestler et al "Stimulation of rat ovarian cell steroidogenesis by high density lipoproteins modified with tetranitromethane" Nestler J E, Chacko G K, Strauss J F 3rd. J Biol Chem 1985 Jun 25;260(12):7316-21).

6. Glutamic acid (and aspartic acid) modifications: In order to modify carboxyl groups, erythropoietin (100 ug) was incubated with 0.02 M EDC in 1M glycinamide at pH 4.5 at room temperature for 60 minutes as described in Carraway et al "Carboxyl group modification in chymotrypsin and chymotrypsinogen." Carraway K L, Spoerl P, Koshland D E Jr. J Mol Biol 1969 May 28;42(1):133-7.

7. Tryptophan residue modifications: erythropoietin (100 ug) was incubated with 20 uM n-bromosuccinimide in 20 mM potassium phosphate buffer (pH 6.5) at room temperature as described in Ali et al., J Biol Chem. 1995 Mar. 3;270(9):4570-4. The number of oxidized tryptophan residues was determined by the method described in Korotchkina (Korotchkina, L G et al Protein Expr Purif. 1995 February;6(1):79-90).

8. Removal of amino groups: In order to remove amino groups of erythropoietin (100 ug) was incubated with in PBS (pH 7.4) containing 20 mM ninhydrin (Pierce Chemical, Rockford, Il), at 37 C for two hours as in Kokkini et al (Kokkini, G., et al "Modification of hemoglobin by ninhydrin" Blood, Vol. 556, No 4 1980: 701-705). Reduction of the resulting aldehyde was accomplished by reacting the product with sodium borohydride or lithium aluminum hydride. Specifically, erythropoietin (100 ug) was incubated with 0.1M sodium borohydride in PBS for 30 minutes at room temperature. The reduction was terminated by cooling the samples on ice for 10 minutes and dialyzing it against PBS, three times, overnight. (Kokkini, G., Blood, Vol. 556, No 4 1980: 701-705). Reduction using lithium aluminum hydride was accomplished by incubating erythropoietin (100 ug) with 0.IM lithium aluminum hydride in PBS for 30 minutes at room temperature. The reduction was terminated by cooling the samples on ice for 10 minutes and dialyzing the samples against PBS, three times, overnight.

9. Disulfide reduction and stabilization: erythropoietin (100 ug) was incubated with 500 mM DTT for 15 minutes at 60 C. 20 mM iodoacetamide in water was then added to the mixture and incubated for 25 minutes, at room temperature in the dark.

10. Limited proteolysis: Erythropoietin can be subjected to a limited chemical proteolysis that targets specific residues. Erythropoietin was reacted with 2-(2-nitrophenylsulfenyl)-3-methyl-3'-bromoindolenine which cleaves specifically after tryptophan residues in a 50 times excess in 50% acetic acid for 48 hours in the dark at room temperature in tubes capped under nitrogen pressure. The reaction was terminated by quenching with tryptophan and desalting.

As noted above, erythropoietin or asialoerythropoietin may be modified, yet multiple modifications as well as additional modifications of the erythropoietin molecule may also be performed without deviating from the spirit of the present invention. Any of the foregoing examples may be carried out with partially desialylated erythropoietin, which may be prepared as described below. For example, any of the aforementioned modified erythropoietins may be modified at one or more arginine residues by using, for example, phenylglyoxal according to the protocol of Takahashi (1977, *J. Biochem.* 81:395402), which may be carried out for variable lengths of time ranging from 0.5 to 3 hrs at room temperature. The reaction was terminated by dialyzing the reaction mixture against water. Use of such modified forms of erythropoietin is fuilly embraced herein.

EXAMPLE 4

Tissue Protective Cytokines Have Neuro Protective Effect

The neuroprotective affects of the tissue protective cytokines of the present invention was evaluated using a water intoxication assay in accordance with Manley et al., 2000, Aquaporin-4 deletion in mice reduces brain edema after acute water intoxication and ischemic stroke, Nat Med 2000 February;6(2):159-63. Female C3H/HEN mice were used. The mice were given 20% of their body weight as water IP with 400 ng/kg bw DDAVP (desmopressin). The mice were administered erythropoietin (A) or a tissue protective cytokine: asialoerythropoietin (B), carbamylated asialoerythropoietin (C), succinylated asialoerythropoietin (D), acetylated asialoerythropoietin (E), iodinated asialoerythropoietin (F), carboxymethylated asialoerythropoietin (G), carbamylated erythropoietin (H), acetylated erythropoietin (I), iodinated erythropoietin (J), or N$^\epsilon$-carboxy methyl erythropoietin (K). The mice were given a 100 microgram/kg dose of erythropoietin or tissue protective cytokine intraperitoneally 24 hrs before administration of the water and again at the time of the water administration. A modified scale from Manley et al. was used to evaluate the mice. The modified scale is as listed below:

| 1. Explores cage/table | |
|---|---|
| Yes | 0 |
| No | 1 |
| 2. Visually tracks objects | |
| Yes | 0 |
| No | 1 |
| 3. Whisker movement | |
| Present | 0 |
| Absent | 1 |
| 4. Leg-tail movements | |
| Normal | 0 |
| Stiff | 1 |
| Paralyzed | 2 |
| 5. Pain withdrawal (toe pinch) | |
| Yes | 0 |
| No | 1 |
| 6. Coordination of movement | |
| Normal | 0 |
| Abnormal | 1 |
| 7. Stops at edge of table | |
| Yes | 0 |
| No | 1 |
| Total score possible: | 8 |

Figure 12:
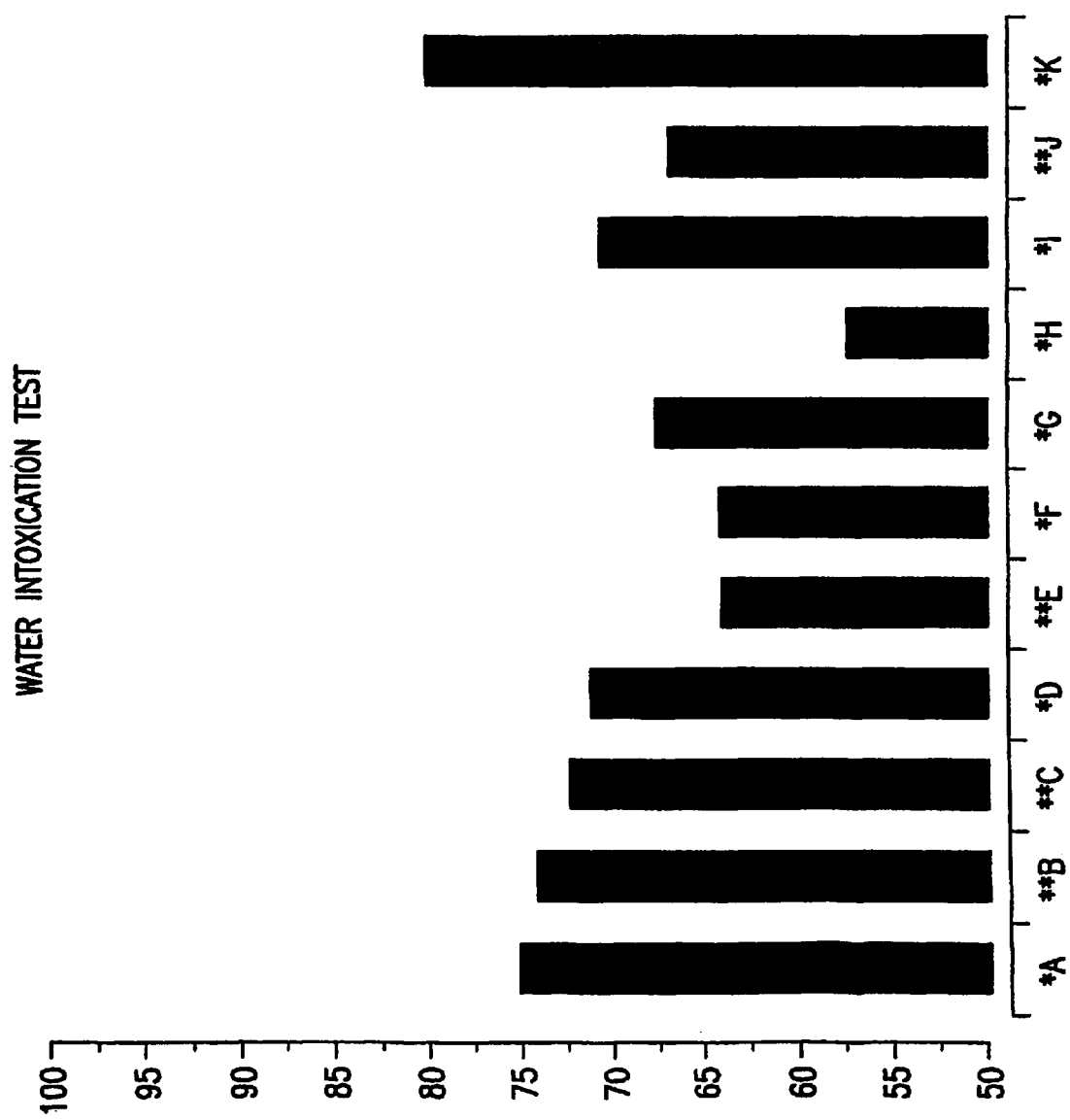
FIG. 12 shows the effect of tissue protective cytokines in the water intoxication assay.

The mice were scored at the following time points: 15, 30, 45, 60, 75, 90, 120, 150, 180 minutes. Score as plotted is the area under the entire time curve, as percent of animals that had received saline only. FIG. 12 shows the scores of the mice who received erythropoietin or one of the tissue protective cytokines of the present invention as a percentage of the score obtained by the control mice. The mice who received the tissue protective cytokines of the present invention exhibited less neurological damage and therefore scored better on the modified scale. FIG. 12 shows that the tissue protective cytokines of the present invention protect neuronal tissue.

EXAMPLE 5

Erythropoietin Crosses the Blood-cerebrospinal Fluid Tight Barrier

Figure 13:
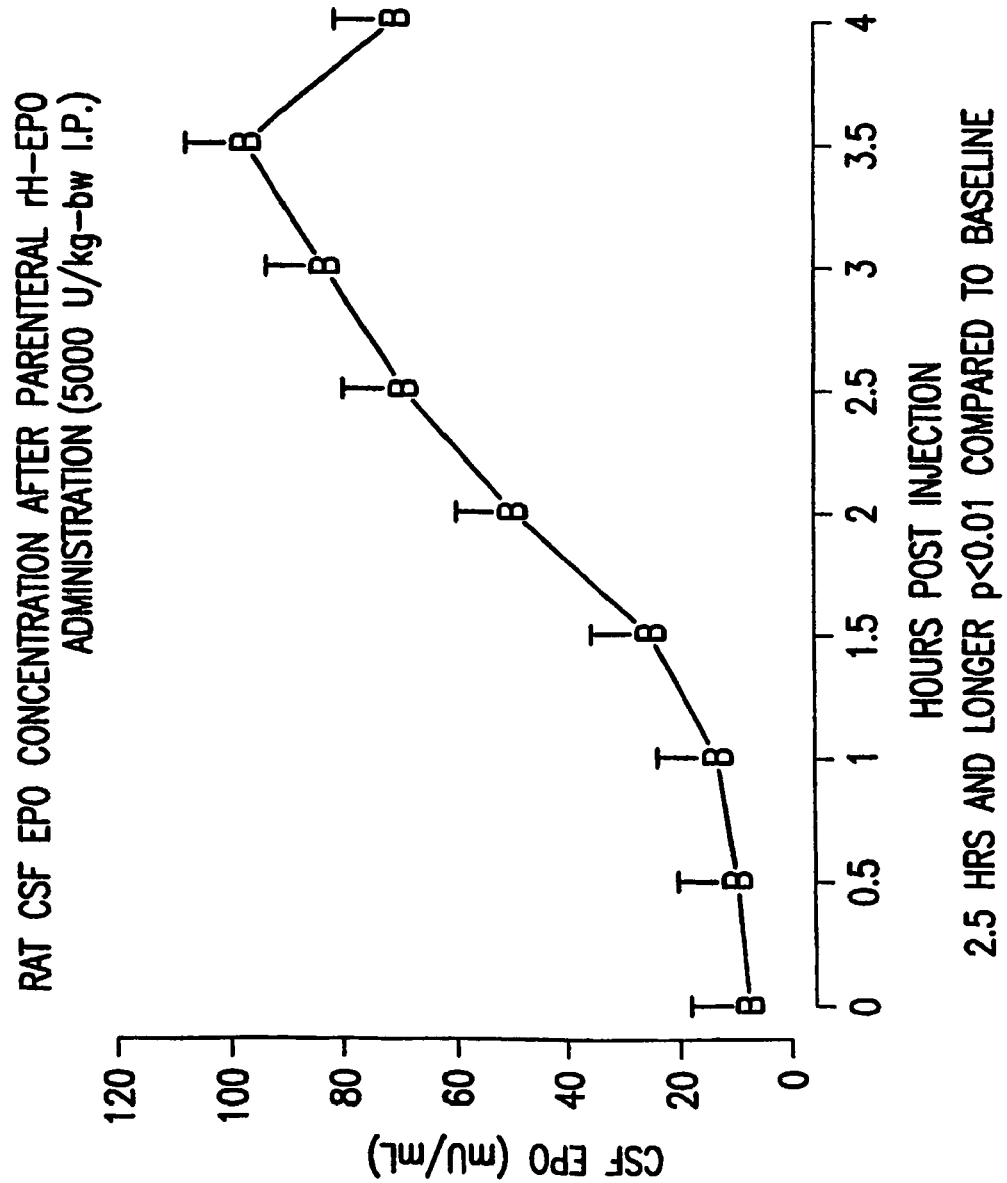
FIG. 13 depicts the translocation of parenterally-administered erythropoietin into the cerebrospinal fluid.

Adult male Sprague-Dawley rats were anesthetized and administered recombinant human erythropoietin intraperitoneally. Cerebrospinal fluid was sampled from the cisterna magna at 30 minute intervals up to 4 hrs and the erythropoietin concentration determined using a sensitive and specific enzyme-linked immunoassay. As illustrated in FIG. 13, the baseline erythropoietin concentration in CSF is 8 mU/ml. After a delay of several hours, the levels of erythropoietin measured in the CSF begin to rise and by 2.5 hours and later are significantly different from the baseline concentration at the $p<0.01$ level. The peak level of about 100 mU/ml is within the range known to exert protective effects in vitro (0.1 to 100 mU/ml). The time to peak occurs at about 3.5 hrs, which is delayed significantly from the peak serum levels (less than 1 hr). The results of this experiment illustrate that significant levels of erythropoietin can be accomplished across a tight cellular junction by bolus parenteral administration of erythropoietin at appropriate concentrations. One of ordinary skill in the art would recognize that similar results would be expected from the tissue protective cytokines of the present invention.

EXAMPLE 6

Maintenance of Function in Heart Prepared for Transplantation

Wistar male rats weighing 300 to 330 g are given erythropoietin (5000 U/kg body weight) or vehicle 24 h prior to removal of the heart for ex vivo studies, done in accordance with the protocol of Delcayre et al., 1992, *Amer. J. Physiol.* 263:H1537-45. Animals are sacrificed with pentobarbital (0.3 mL), and intravenously heparinized (0.2 mL). The hearts are initially allowed to equilibrate for 15 min. The left ventricular balloon is then inflated to a volume that gives an end-diastolic pressure of 8 mm Hg. A left ventricular pressure-volume curve is constructed by incremental inflation of the balloon volume by 0.02 ml aliquots. Zero volume is defined as the point at which the left ventricular end-diastolic pressure is zero. On completion of the pressure-volume curve, the left ventricular balloon is deflated to set end-diastolic pressure back to 8 mmHg and the control period is pursued for 15 min., after check of coronary flow. Then the heart is arrested with 50 mL Celsior+molecule to rest at 4° C. under a pressure of 60 cm $H_2O$. The heart is then removed and stored 5 hours at 4° C. in plastic container filled with the same solution and surrounded with crushed ice.

Figure 14:
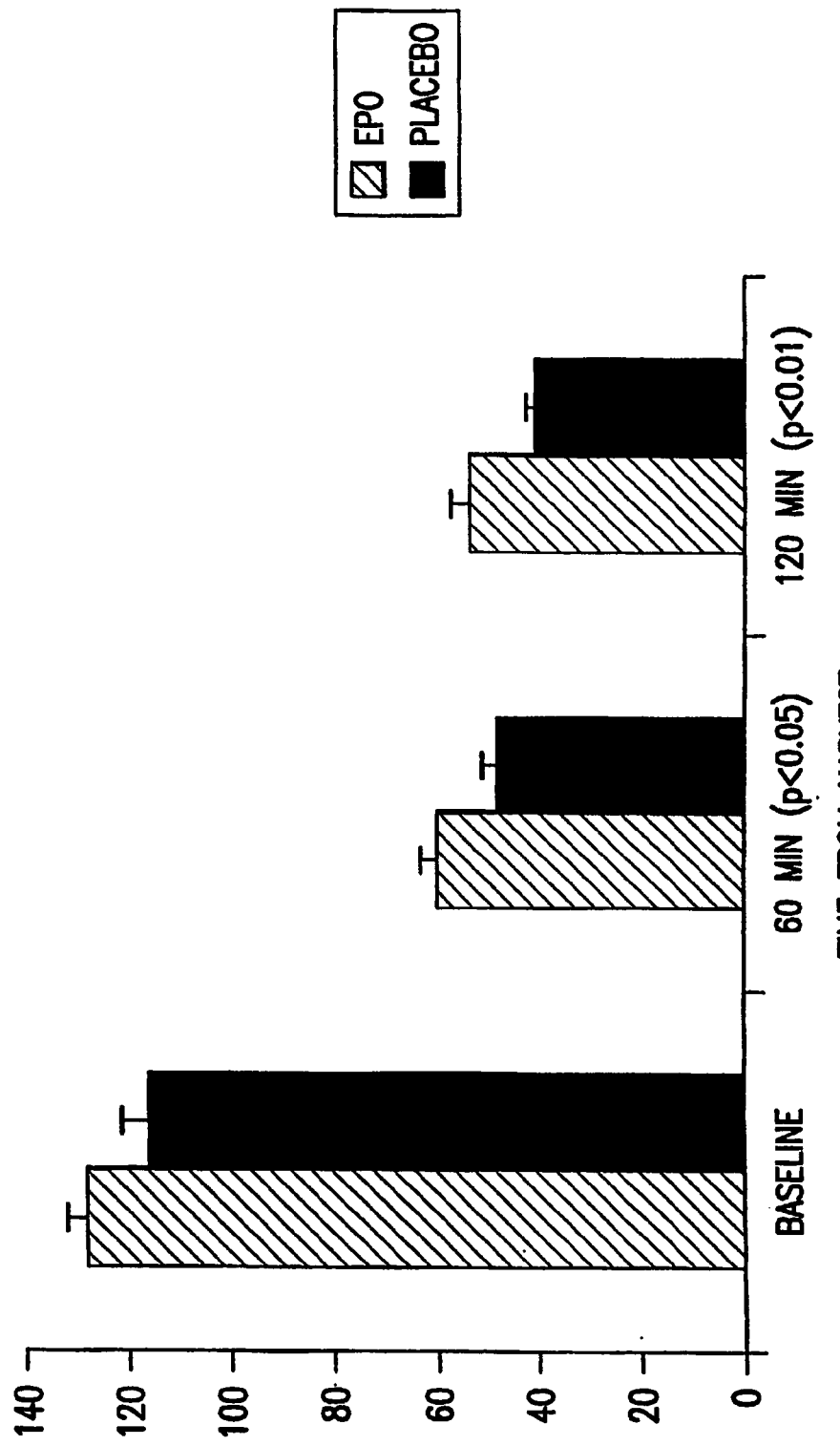
FIG. 14 shows the maintenance of the function of a heart prepared for transplantation by erythropoietin.

On completion of storage, the heart is transferred to a Langendorff apparatus. The balloon catheter is re-inserted into the left ventricle and re-inflated to the same volume as during preischemic period. The heart is re-perfused for at least 2 hours at 37° C. The re-perfusion pressure is set at 50 cm $H_2O$ for 15 min of re-flow and then back to 100 cm $H_2O$ for the 2 next hours. Pacing (320 beats per minute) is re-instituted. Isovolumetric measurements of contractile indexes and diastolic pressure are taken in triplicate at 25, 45, 60, 120 min of reperfusion. At this time point pressure volume curves are performed and coronary effluent during the 45 min reperfilsion collected to measure creatine kinase leakage. The two treatment groups are compared using an unpaired t-test, and a linear regression using the end-diastolic pressure data is used to design compliance curves. As shown in FIG. 14, significant improvement of left ventricular pressure developed occurs after treatment with erythropoietin, as well as improved volume-pressure curve, decrease of left diastolic ventricular pressure and decrease of creatine kinase leakage. Similar results would be expected from treatment with the tissue protective cytokines of the present invention.

EXAMPLE 7

Erythropoietin Protects Myocardium from Ischemic Injury

Figure 15:
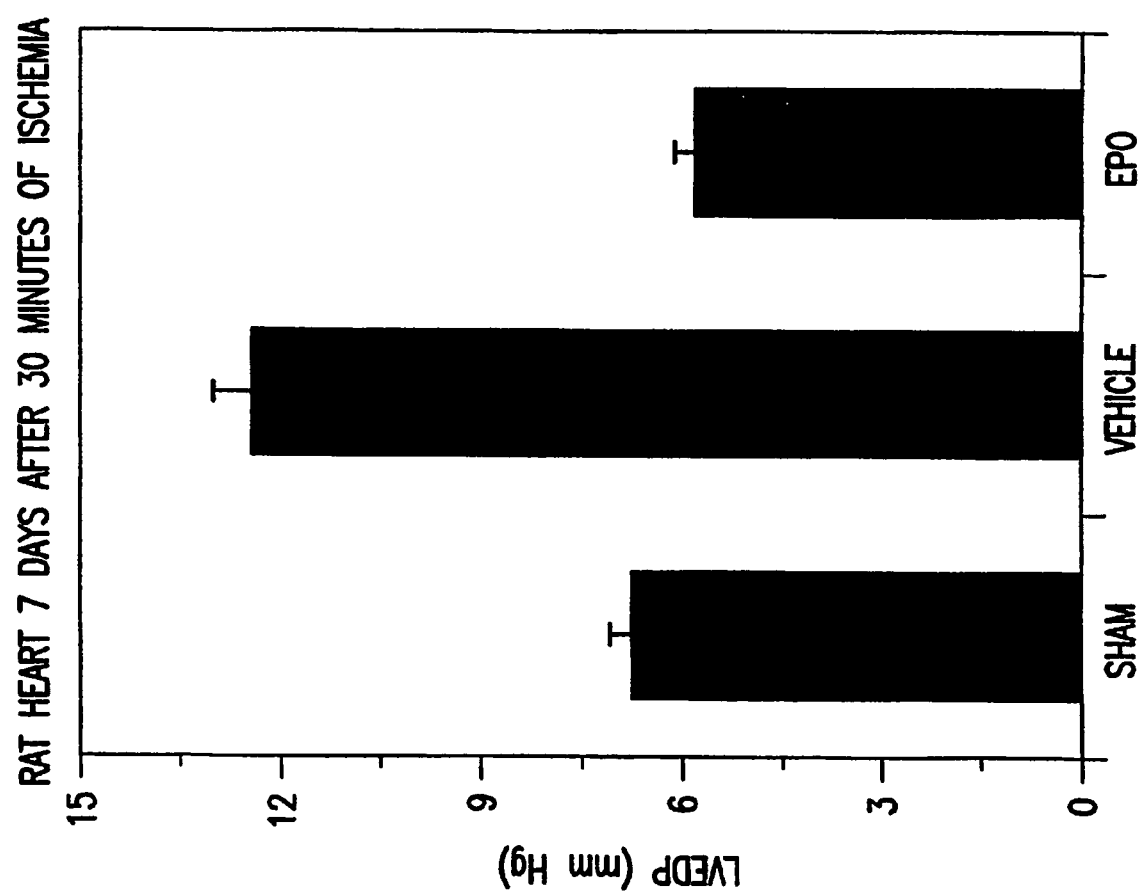
FIG. 15 shows the protection of the myocardium from ischemic damage by erythropoietin after temporary vascular occlusion.

Adult male rats given recombinant human erythropoietin (5000 U (40 µg)/kg body weight) 24 hrs previously are anesthetized and prepared for coronary artery occlusion. An additional dose of erythropoietin is given at the start of the procedure and the left main coronary artery occluded for 30 minutes and then released. The same dose of erythropoietin is given daily for one week after treatment. The animals are then studied for cardiac function. As FIG. 15 illustrates, animals receiving a sham injection (saline) demonstrated a large increase in the left end diastolic pressure, indicative of a dilated, stiff heart secondary to myocardial infarction. In contradistinction, animals receiving erythropoietin suffered no decrement in cardiac function, compared to sham operated controls (difference significant at the p <0.01 level). Similar results would be expected from treatment with the tissue protective cytokines of the present invention.

EXAMPLE 8

Protection of Retinal Ischemia by Peripherally-administered Erythropoietin

Figure 16:
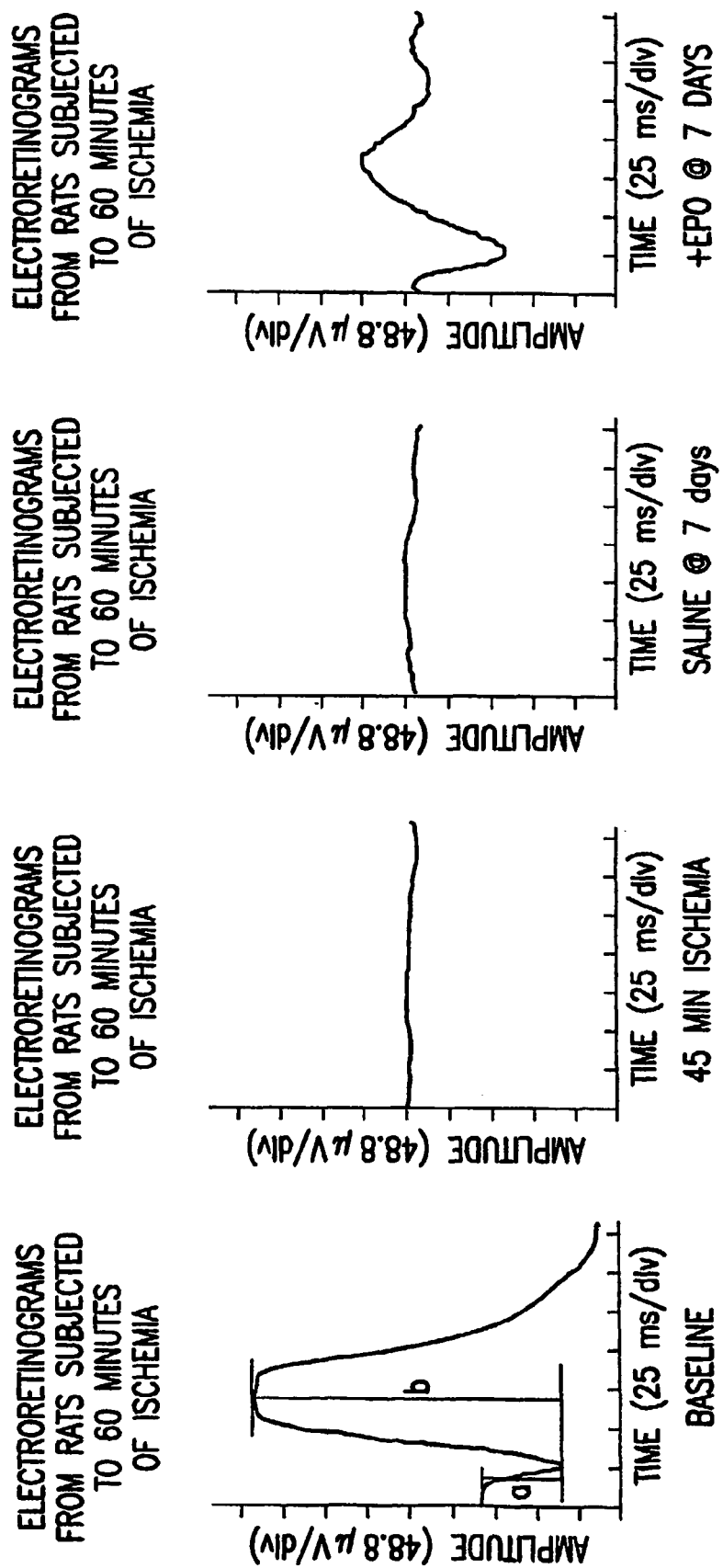
FIG. 16A-16D depicts the effects of erythropoietin treatment in a rat glaucoma model.
Figure 17:
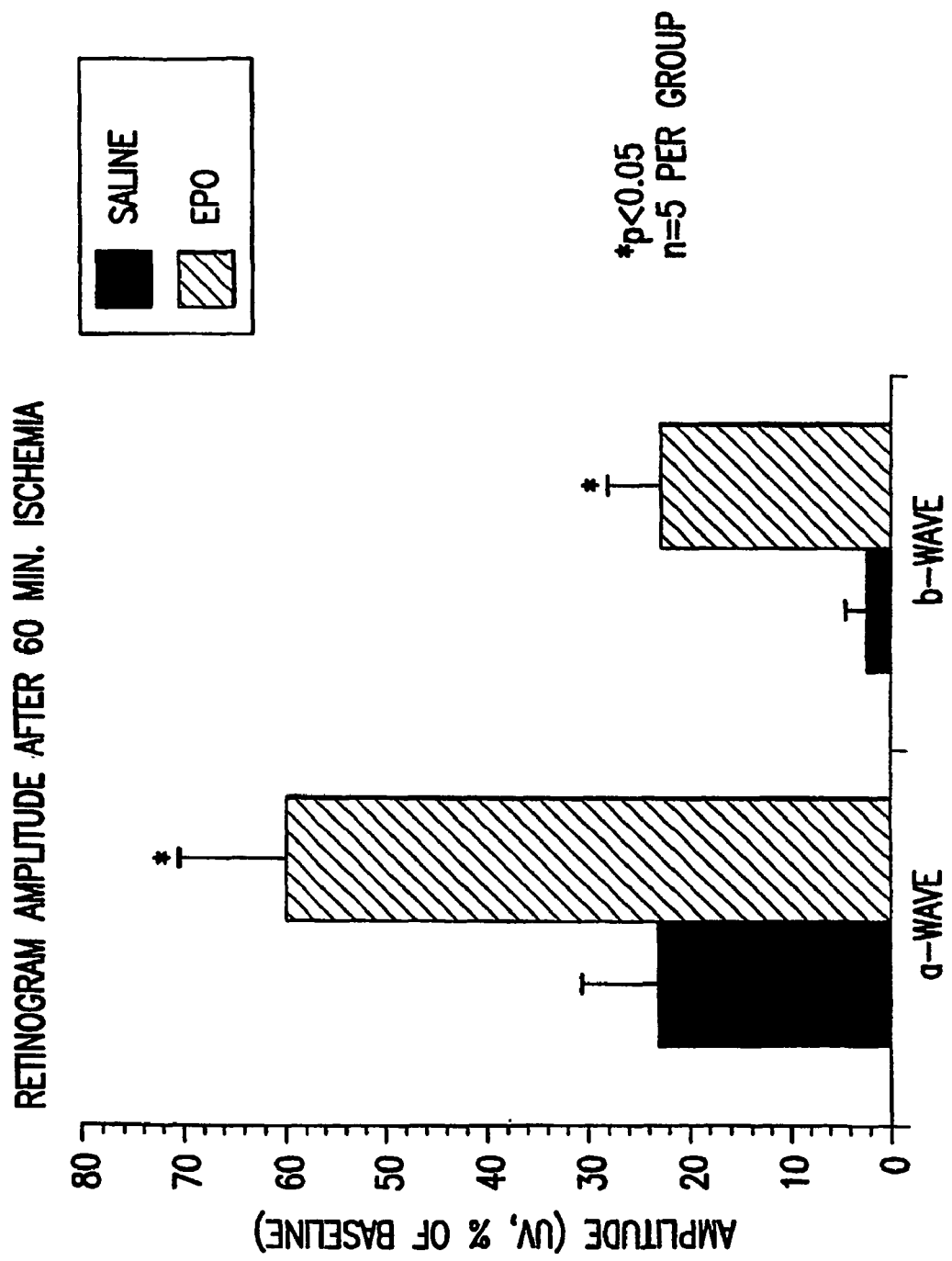
FIG. 17 shows the extent of preservation of retinal function by erythropoietin in the rat glaucoma model.

Retinal cells are very sensitive to ischemia such that many will die after 30 minutes of ischemic stress. Further, subacute or chronic ischemia underlies the deterioration of vision which accompanies a number of common human diseases, such as diabetes mellitus, glaucoma, and macular degeneration. At the present time there are no effective therapies to protect cells from ischemia. A tight endothelial barrier exists between the blood and the retina that excludes most large molecules. To test whether peripherally-administered erythropoietin will protect cells sensitive to ischemia, an acute, reversible glaucoma rat model was utilized as described by Rosenbaum et al. (1997; *Vis. Res.* 37:3443-5 1). Specifically, saline was injected into the anterior chamber of the eye of adult male rats to a pressure above systemic arterial pressure and maintained for 60 minutes. Animals were administered saline or 5000 U (40 μg) erythropoietin/kg body weight intraperitoneally 24 hours before the induction of ischemia, and continued as a daily dose for 3 additional days. Electroretinography was performed on dark-adapted rats 1 week after treatment. FIG. 16-17 illustrate that the administration of erythropoietin is associated with good preservation of the electroretinogram (ERG) (Panel D), in contrast to animals treated with saline alone (Panel C), for which very little function remained. FIG. 16 compares the electroretinogram a- and b-wave amplitudes for the erythropoietin-treated and saline-treated groups, and shows significant protection afforded by erythropoietin. Similar results are obtainable from treatment with the tissue protective cytokines of the present invention.

EXAMPLE 9

Figure 18:
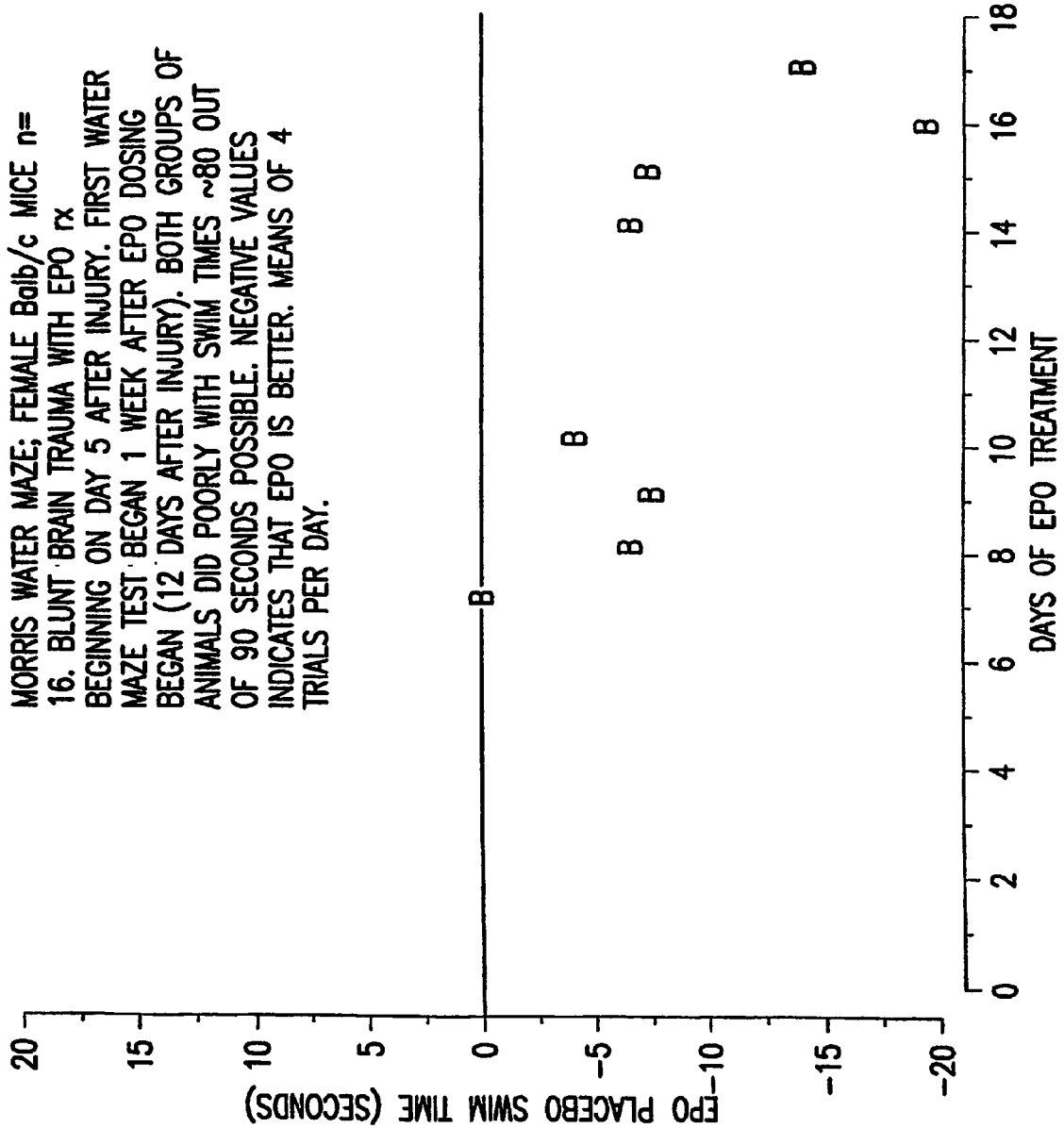
FIG. 18 depicts the restoration of cognitive function following brain trauma by administration of erythropoietin starting five days after trauma.
Figure 19:
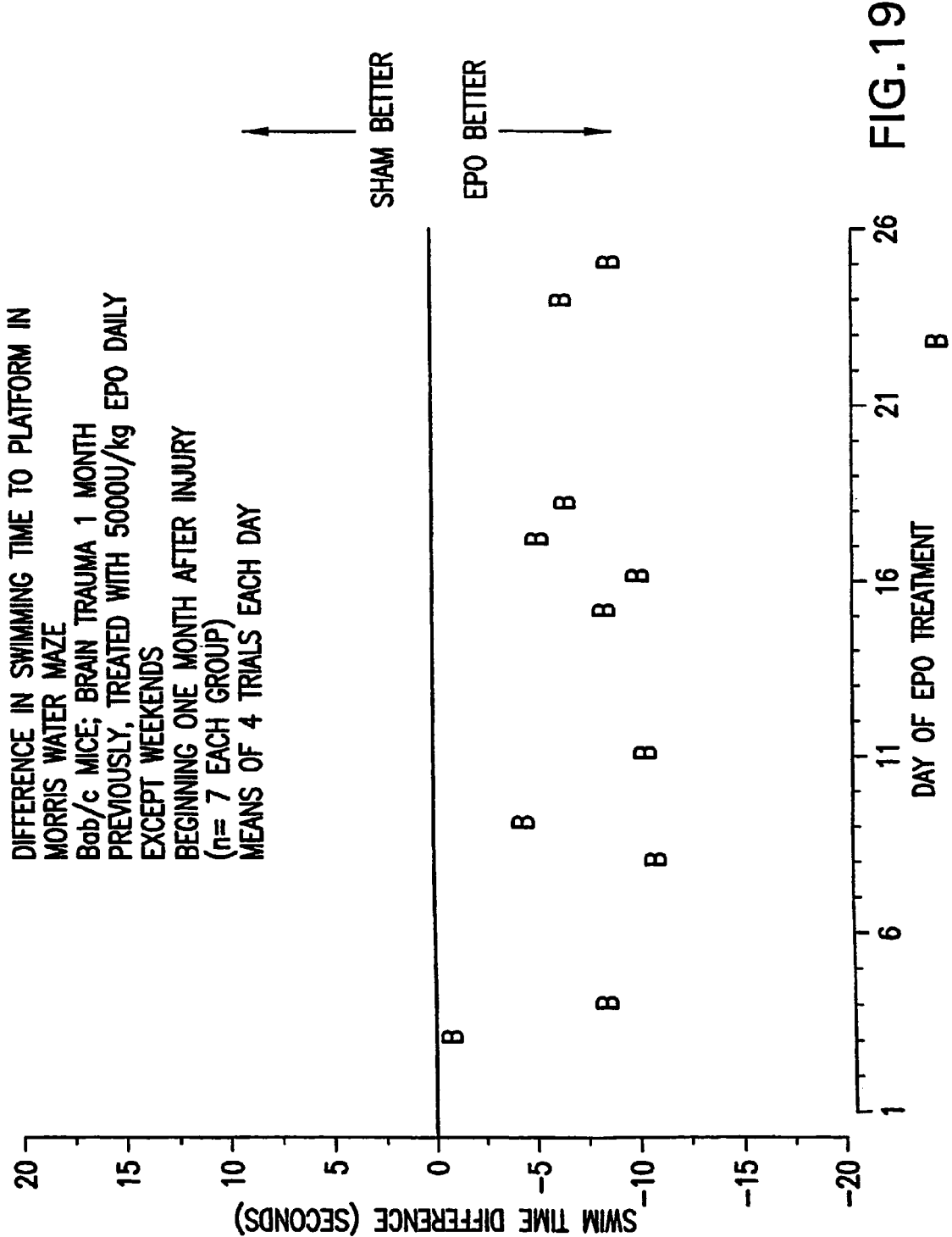
FIG. 19 depicts the restoration of cognitive function following brain trauma by administration of erythropoietin starting 30 days after trauma

Restorative Effects of Erythropoietin on Diminshed Cognitive Function Arising from Brain Injury In a study to demonstrate the ability of erythropoietin to restore diminished cognitive function in mice after receiving brain trauma, female Balb/c mice were subject to blunt brain trauma as described in Brines et al. PNAS 2000, 97; 10295-10672 and five days later, daily erythropoietin administration of 5000 U (40 μg)/kg-bw intraperitoneally was begun. Twelve days after injury, animals were tested for cognitive function in the Morris water maze, with four trials per day. While both treated and untreated animals performed poorly in the test (with swim times of about 80 seconds out of a possible 90 seconds), FIG. 18 shows that the erythropoietin-treated animals performed better (in this presentation, a negative value is better). Even if the initiation of erythropoietin treatment is delayed until 30 days after trauma (FIG. 19), restoration of cognitive function is also seen. Similar results would be expected from treatment with the tissue protective cytokines of the present invention.

EXAMPLE 10

Kainate Model

Figure 20:
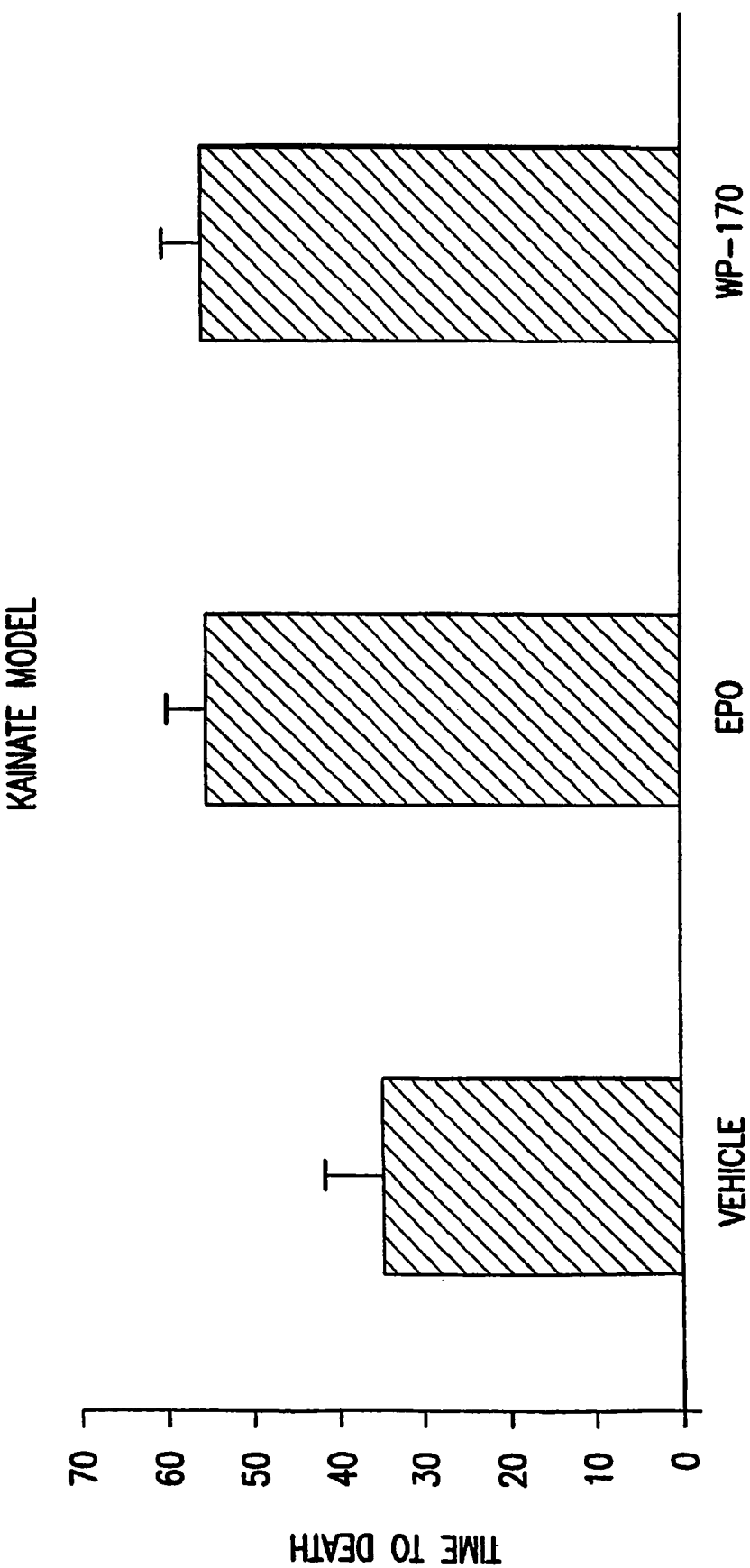
FIG. 20 depicts the efficacy of human asialoerythropoietin in a kainate model of cerebral toxicity.

In the kainate neurotoxicity model, asialoerythropoietin was administered according to the protocol of Brines et al. Proc. Nat. Acad. Sci. U.S.A. 2000, 97; 10295-10672 at a dose of 5000U (40 μg)/kg-bw given intraperitoneally 24 hours before the administration of 25 mg/kg kainate is shown to be as effective as erythropoietin, as shown by time to death (FIG. 20). Similar results are obtainable from treatment with the tissue protective cytokines of the present invention.

EXAMPLE 11

Spinal Cord Injury Models

1. Rat Spinal Cord Compression Testing Erythropoietin and Tissue Protective Cytokines Wistar rats (female) weighing 180-300 g were used in this study. The animals were fasted for 12 h before surgery, and were humanely restrained and anesthesized with an intraperitoneal injection of thiopental sodium (40 mg/kg-bw). After infiltration of the skin bupivacaine 0.25%), a complete single level (T-3) laminectomy was performed through a 2 cm incision with the aid of a dissecting microscope. Traumatic spinal cord injury was induced by the extradural application of a temporary aneurysm clip exerting a 0.6 newton (65 grams) closing force on the spinal cord for 1 minute. After removal of the clip, the skin incision was closed and the animals allowed to recover fully from anethesia and returned to their cages. The rats were monitored continuously with bladder palpation at least twice daily until spontaneous voiding resumed.

40 animals were randomly divided into five groups. Animals in the control group (I) (n=8) received normal saline (via intravenous injection) immediately after the incision is closed. Group (II; n=8) received rhEPO@16 micrograms/kg-bw iv; group (III) received an asialo tissue protective cytokine of the present invention (asialoerythropoietin)@16 micrograms/kg-bw iv, group (IV) received an asialo tissue protective cytokine@30 micrograms/kg-bw iv, and group (V) received an asialo tissue protective cytokine of the present invention (asialoerythropoietin)@30 micrograms/kg-bw; all as a single bolus intravenous injection immediately after removal of the aneurysm clip.

Motor neurological function of the rats will be evaluated by use of the locomotor rating scale of Basso et al. In this scale, animals are assigned a score ranging from 0 (no observable hindlimb movements) to 21 (normal gait). The rats will be tested for functional deficits at 1,12,24, 48, 72 hours and then at 1 week after injury by the same examiner who is blind to the treatment each animal receives.

Figure 21:
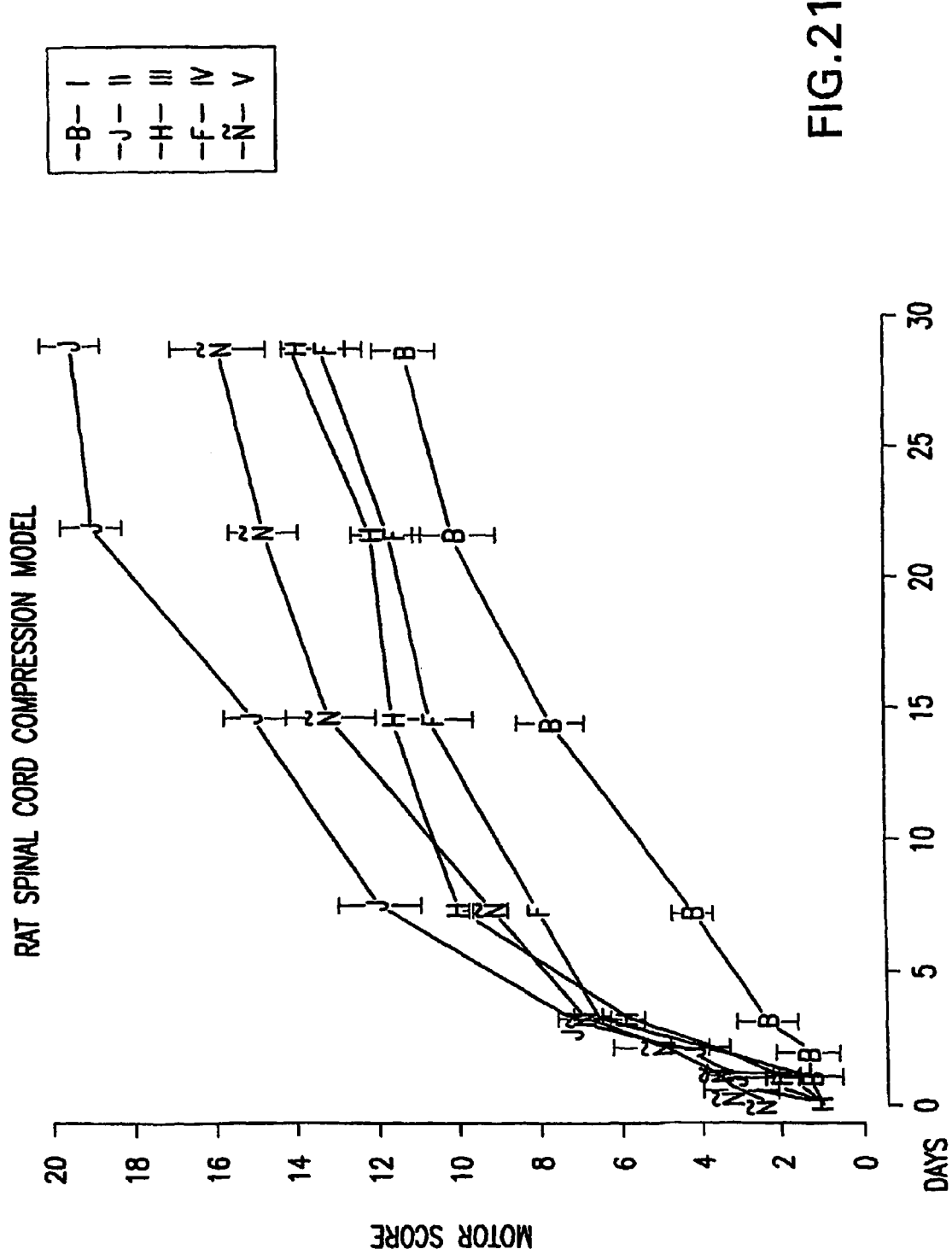
FIG. 21 depicts the efficacy of tissue protective cytokines in a rat spinal cord injury model.

FIG. 21 is a graph demonstrating the locomotor ratings of the rats recovering from the spinal cord trauma over a period of thirty days. As can be seen from the graph, the rats that were given erythropoietin (group II) or tissue protective cytokines (groups III-V) recovered from the injury more readily and demonstrated better overall recovery from the injury than the control rats. Similar results would be expected from the therapeutic treatment with the tissue protective cytokines of the present invention.

2. Rabbit Spinal Cord Ischemia Testing Erythropoietin and a Tissue Protective Cytokine.

36 New Zealand White rabbits (8-12 months old, male) weighing 1.5-2.5 kg were used in this study. The animals were fasted for 12 hours and humanely restrained. Anesthesia induction was via 3 % halothane in 100 % oxygen and maintained with 0.5-1.5 % halothane in a mixture of 50% oxygen and 50% air. An intravenous catheter (22 gauge) was placed in the left ear vein. Ringers lactate was infused at a rate of 4 ml/kg body weight (bw) per hour during the surgical procedure. Preoperatively, cefazoline 10 mg/kg-bw was administered intravenously for prophylaxis of infection. The animals were placed in the right lateral decubitus position, the skin prepared with povidone iodine, infiltrated with bupivacaine (0.25%) and a flank skin incision was made parallel to the spine at the 12th costal level. After incision of the skin and subcutaneous thoracolumbar fascia, the longissimus lumborum and iliocostalis lumborum muscles were retracted. The abdominal aorta was exposed via a left retroperitoneal approach and mobilized just inferior to the left renal artery. A piece of PE-60 tubing was looped around the aorta immediately distal to the left renal artery and both ends passed through a larger rubber tube. By pulling on the PE tubing, the aorta was non-traumatically occluded for 20 minutes. Heparin (400 IU) was administered as an intravenous bolus before aortic occlusion. After 20 minutes of occlusion, the tube and catheter were removed, the incision was closed and the animals were monitored until full recovery and then were serially assessed for neurological function.

36 animals were randomly divided into six groups. In a control group (I), animals (n=6) received normal saline intravenously immediately after release of aortic occlusion. Group (II) received rhEPO@6.5 microgram/kg-bw; group (III) received a tissue protective cytokine (carbamylated erythropoietin)@6.5 microgram/kg-bw; group (IV) received another tissue protective cytokine (asialoerythropoietin)@6.5 microgram/kg-bw; group (V) received the same tissue protective cytokine as group (I) but @20 microgram/lkg-bw; and group (VI) received yet another tissue protective cytokine (asialocarbamylatederythropoietin) @20 microgram/kg-bw all intravenously immediately after reperfusion (n=6 for each group).

Motor function was assessed according to the criteria of Drummond and Moore by an investigator blind to the treatment at 1, 24 and 48 h after reperfusion. A score of 0 to 4 was assigned to each animal as follows: 0=paraplegic with no evident lower extremity motor function; 1=poor lower extremity motor function, weak antigravity movement only; 2=moderate lower extremity function with good antigravity strength but inability to draw legs under body; 3=excellent motor function with the ability to draw legs under body and hop, but not normally; 4=normal motor function. The urinary bladder was evacuated manually in paraplegic animals twice a day.

Figure 22:
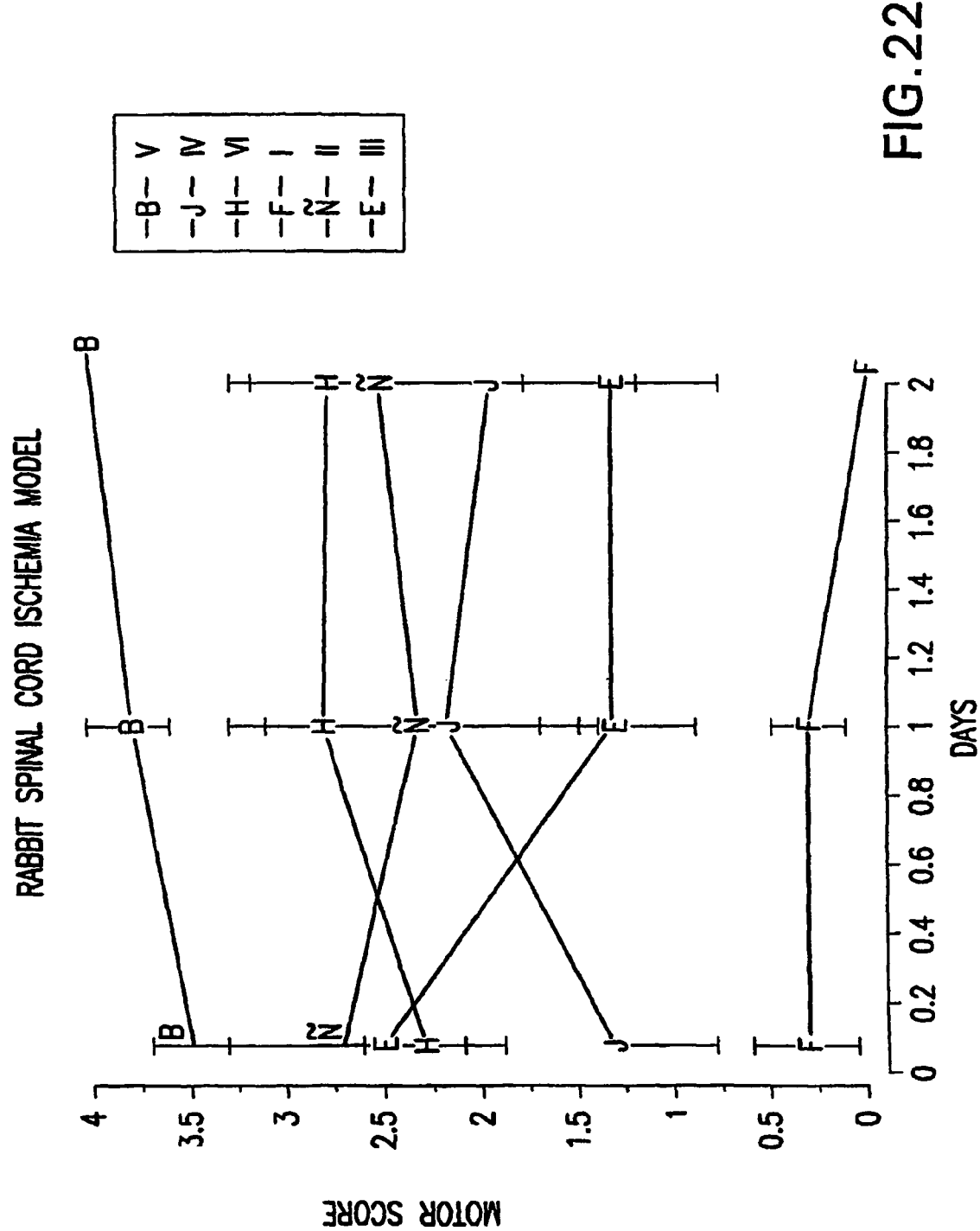
FIG. 22 shows the efficacy of tissue protective cytokines within a rabbit spinal cord injury model.

FIG. 22 is a graph plotting motor function of the recovering rabbits. The graph demonstrates that even over a period of only two days erythropoietin and the tissue protective cytokines of the present invention permit the rabbits to recover more fully from the spinal cord injury. Similar results would be expected from the therapeutic treatment with the tissue protective cytokines of the present invention.

EXAMPLE 12

Anti-Inflammatory Affects of Erythropoietin

In-Vivo Studies:
1. Middle Cerebral Artery Occlusion (MCAO) Studies on Rats.

Male Crl:CD(SD)BR rats weighing 250-280 g were obtained from Charles River, Calco, Italy. Surgery was performed on these rats in accordance with the teachings of Brines, M. L., Ghezzi, P., Keenan, S., Agnello, D., de Lanerolle, N. C., Cerami, C., Itri, L. M., and Cerami, A. 2000 Erythropoietin crosses the blood-brain barrier to protect against experimental brain injury [In Process Citation] Proc Natl Acad Sci USA 97:10526-10531. Briefly, the rats were anesthetized with chloral hydrate (400 mg/kg-bw, i.p.), the carotid arteries were visualized, and the right carotid was occluded by two sutures and cut. A burr hole adjacent and rostral to the right orbit allowed visualization of the MCA, which was cauterized distal to the rhinal artery. To produce a penumbra (borderzone) surrounding this fixed MCA lesion, the contralateral carotid artery was occluded for 1 hour by using traction provided by a fine forceps and then re-opened. PBS or rhEPO (5,000 U/kg-bw, i.p.; previously shown to be protective in this model (1)) were administered immediately after the MCAO. When indicated, TNF and IL-6 were quantified in brain cortex homogenates as previously described (8). MCP-1 was measured in the homogenates using a commercially available ELISA kit (biosource, Camarillo, Calif.).

Twenty-four hours after MCAO, the rats were anesthetized as described above and transcardially perfused with 100 ml saline followed by 250 ml of sodium phosphate buffered 4% paraformaldehyde solution. Brains were rapidly removed, fixed in sodium phosphate buffered 4% paraformaldehyde solution for two hours, transferred to 20% sucrose solution in PBS overnight, then in 30% sucrose solution until they sank and were then frozen in 2-methylbutane at −45° C. Sections (30 µm) were cut on a cryostat (HM 500 OM, Microm) at −20° C. in the transverse plane through the brain and selected every fifth section for histochemistry against the different antigens, or hematoxylin-eosin staining. Free floating sections were processed for immunoreactivity both with anti-glial fibrillary acid protein (GFAP) mouse monoclonal antibody (1:250, Boehringher Mannheim, Monza, Italy) and with anti-cdl lb (MRC OX-42) mouse monoclonal antibody (1:50, Serotec, UK), according to the protocols described by Houser et al. and the manufacturer's protocol respectively. All sections were mounted for light microscopy in saline on coated slides, dehydrated through graded alcohols, fixed in xylene and coverslipped using DPX mountant (BDH, Poole, UK). Adjacent sections were stained with hematoxylin-eosin as described (10).

Figure 23A:
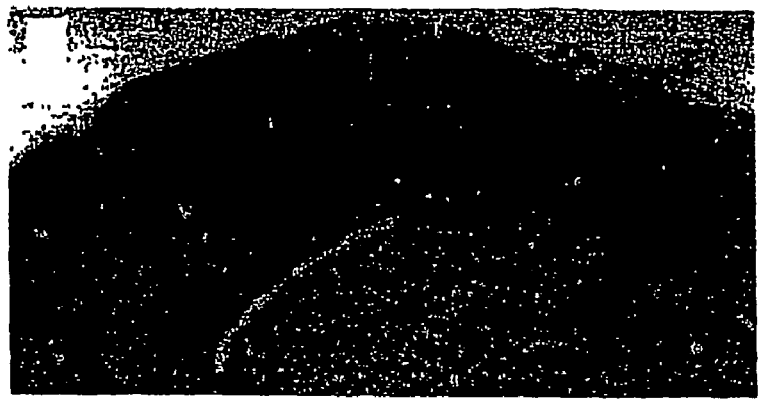
FIG. 23A-23C shows a coronal section of the brain cortical layer stained by hematoxilyn and eosin.
Figure 23B:
Figure 23C:

FIG. 23 shows a coronal section of the brain cortical layer stained by hematoxilyn and eosin. Control rat (A), ischemic rat treated with PBS (B), ischemic rat treated with rhEPO (5,000 U/kg-bw, i.p., immediately following MCAO) (C). The section B shows a marked decrease in tissue staining consistent with inflammation, accompanied by a loss of neuronal component compared to the control (A). Systemic rhEPO administration largely reduces the ischemic damage localizing the cell death or injury in a restricted area (C). (Magnification 2.5×. Size bar=800 µm.)

Figure 24A:
FIG. 24A-24C shows coronal sections of frontal cortex adjacent to the region of infarction stained by GFAP antibody.
Figure 24B:
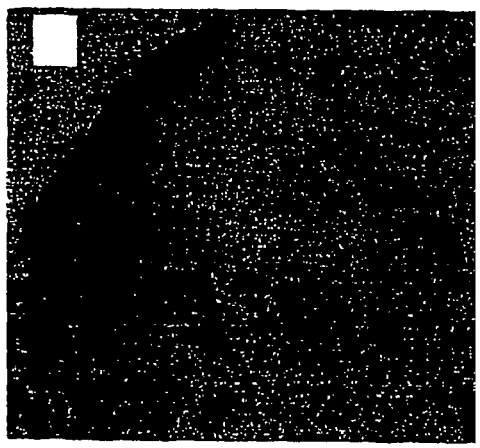
Figure 24C:

FIG. 24 shows coronal sections of frontal cortex adjacent to the region of infarction stained by GFAP antibody. Control rat (A), ischemic rat treated with PBS (B), ischemic rat treated with rhEPO (C). Activated astrocytes are visualized by their GFAP-positive processes (Panel B). There was a marked reduction in number as well as staining intensity of activated astrocytes in a representative rhEPO-treated animal (Panel C). (Magnification 10×. Size bar=200 µm.)

Figure 25A:
FIGS. 25A and 25B shows coronal sections of brain cortical layer stained by OX-42 antibody.
Figure 25B:
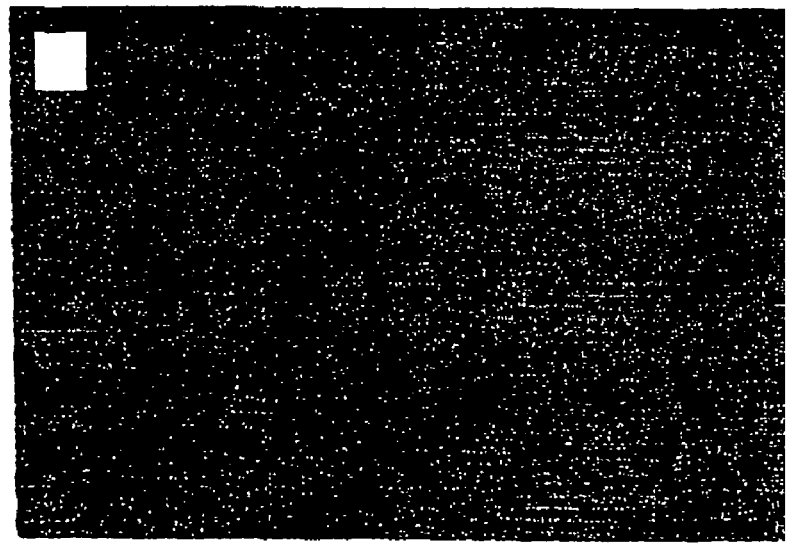

FIG. 25 shows coronal sections of brain cortical layer stained by OX-42 antibody. Ischemic rat treated with PBS (A), ischemic rat treated with rhEPO (B). In the ischemic cerebral hemisphere the cellular staining is especially prominent around the infarcted tissue in both treatment groups, but is much denser and extends further in the saline treated group. (Magnification 20×; Size bar=100 µm).

Figure 26A:
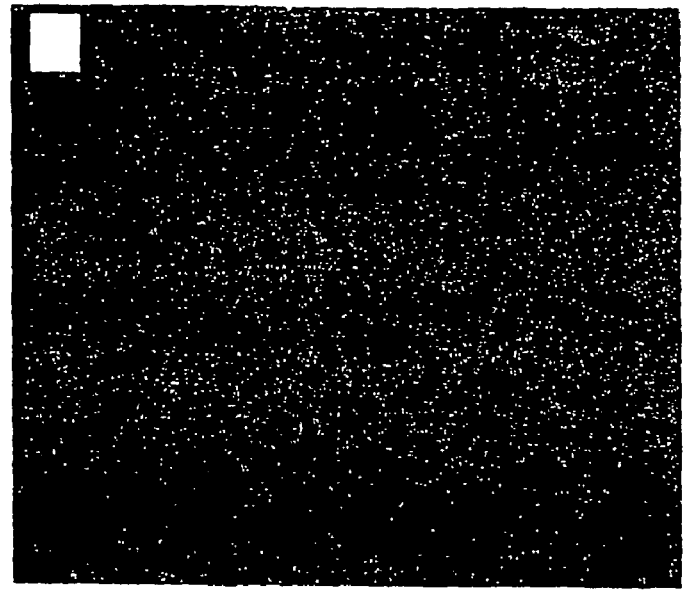
FIGS. 26A and 26B shows coronal sections of brain cortical layer adjacent to the region of infarction stained by OX-42 antibody.
Figure 26B:
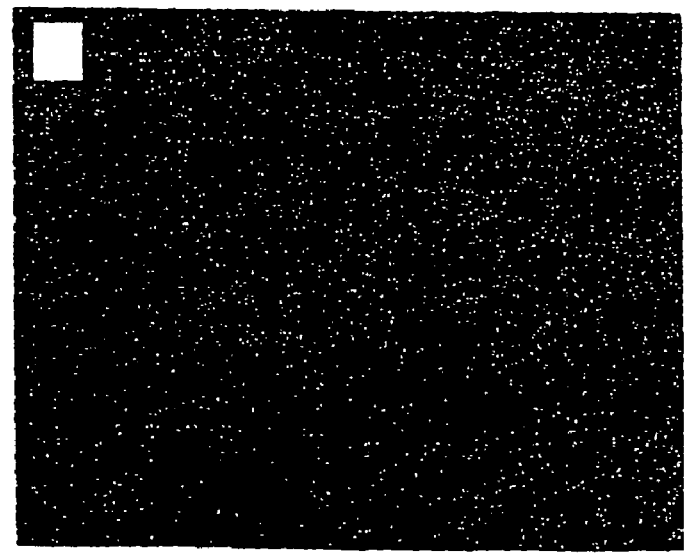

FIG. 26 shows coronal sections of brain cortical layer adjacent to the region of infarction stained by OX-42 antibody. A much higher density of mononuclear inflammatory cells are observed in the tissue from an ischemic rat treated with PBS (A) compared to an ischemic rat treated with rhEPO (B). The infiltrating leukocytes, with typical round shape, potentially will extend the volume of infarction. (Magnification 10×; Size bar=200 µm)

Similar results would be expected from the therapeutic treatment with the tissue protective cytokines of the present invention.

2. Acute Experimental Allergic Encephalomyelitis (EAE) in Lewis Rats

Female Lewis rats, 6-8 weeks of age, were purchased from CHARLES RIVER (Calco, Italy). EAE was induced in rats by injecting 50 µg of guinea pig MBP (SIGMA, St. Louis, Mo.) in water emulsified in equal volumes of complete Freund's adjuvant (CFA, SIGMA) additioned with 7 mg/ml of heat-killed *M. tuberculosis* H37Ra (DIFCO, Detroit, Mich.) in a final volume of 100µ under light ether anesthesia into both hind footpads. Rats were examined in a blinded fashion for signs of EAE and scored as follows: 0, no disease; 1, flaccid tail; 2, ataxia; 3, complete hind limb paralysis with urinary incontinence. Starting from day 3 after immunization, rats were given r-Hu-EPO (EPOetin alfa, PROCRIT, ORTHO BIOTECH Raritan, N.J.) intraperitoneally (i.p.) once a day at the indicated doses, in PBS. Since the clinical-grade EPO contained human serum albumin, control animals were always given PBS containing an identical amount of human serum albumin. Daily administration of 5,000 U/kg-bw of EPO increased the hematocrit by 30% (data not shown). When indicated, rats were injected s.c. once a day from day 3 until day 18 with 1.3 mg/kg-bw dexamethasone (DEX) phosphate disodium salt (SIGMA) corresponding to 1 mg/kg-bw of DEX, dissolved in PBS. When indicated, TNF and IL-6 were quantified in brain and spinal cord homogenates as previously described [Agnello, 2000 #10].

Figure 27:
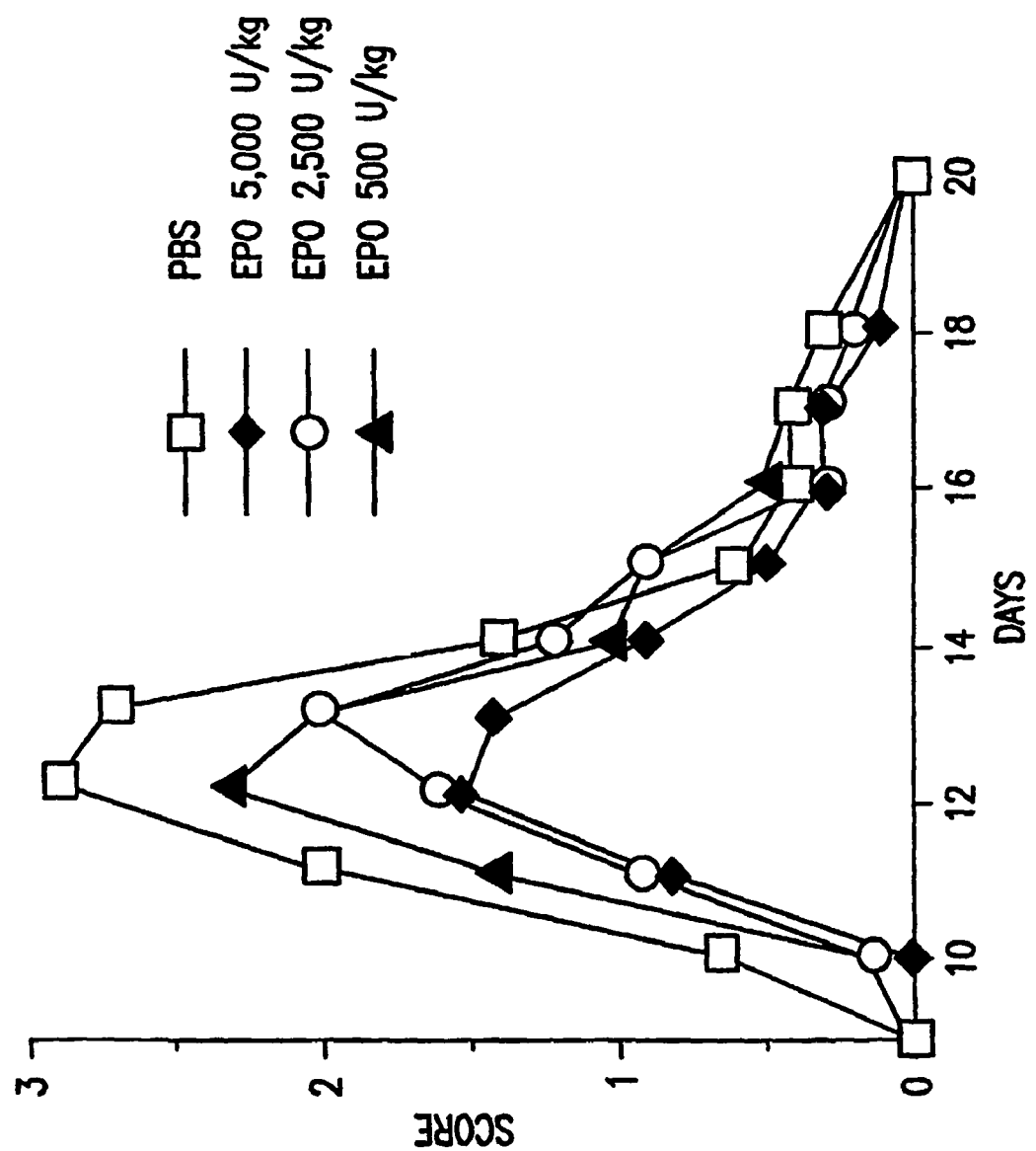
FIG. 27 shows the efficacy of erythropoietin against inflammation in an EAE model.

FIG. 27 shows the protective effect on the clinical signs of EAE of different doses of EPO, given from day 3 after immunization with MBP until day 18. EPO, in a dose-dependent fashion, delayed the onset of disease and decreased disease severity. But, EPO did not delay the time to greatest severity.

Figure 28:
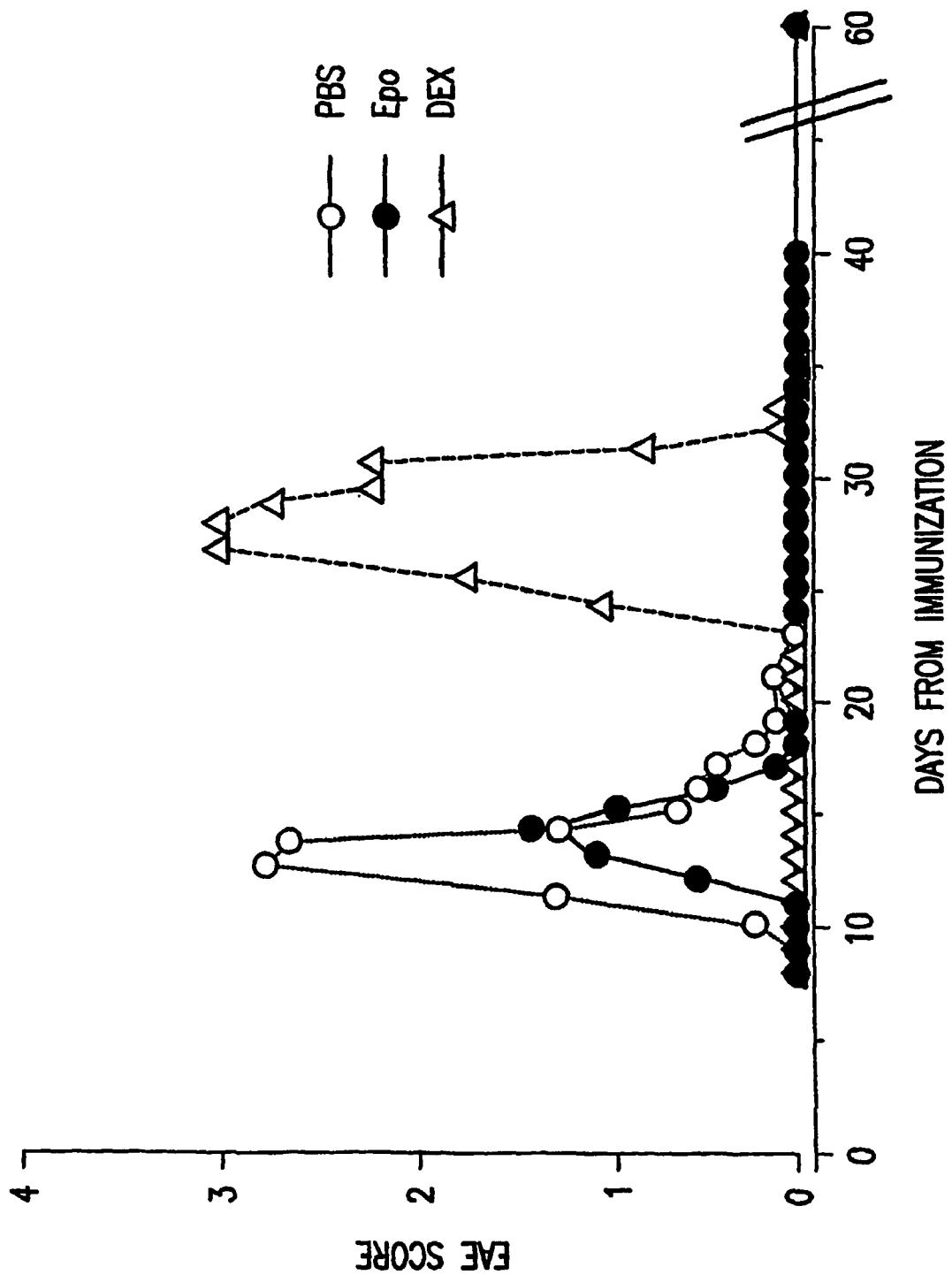
FIG. 28 compares the affects of dexamethasone and erythropoietin on inflammation in the EAE model.

In experiments where treatment of EPO was discontinued after the disease regressed and the rats were monitored up to two months, no relapse was observed, in contrast with DEX which induces an exacerbation of disease after suspending its administration (FIG. 28). Similar results would be expected from the therapeutic treatment with the tissue protective cytokines of the present invention.

In Vitro Studies:

Primary cultures of glial cells were prepared from new born Sprague-Dawley rats 1-2 days old. Cerebral hemispheres were freed from the meninges and mechanically disrupted. Cells were dispersed in a solution of trypsin 2.5% and DNAase 1%, filtered through a 100 µm nylon mesh and plated (140,000 cells per 35 mm dish) in Eagle's minimum essential medium supplemented with 10% fecal calf serum, 0.6% glucose, streptomycin (0.1 mg/ml) and penicillin (100 Ul/ml). Glial cultures were fed twice a week and grown at 37° C. in a humidified incubator with 5% $CO_2$. All experiments were performed on 2-3 week-old glial cell cultures with 97% astrocytes and 3% microglia, as assessed by immunochemistry of GFAP and *Griffonia simplicifolia* isolectin $B_4$. Neuronal cultures were established from the hippocampus of 18-day rat fetuses. Brains were removed and freed from meninges and the hippocampus was isolated. Cells were dispersed by incubation for 15-20 min at 37° C. in a 2.5% trypsin solution followed by tituration. The cell suspension was diluted in the medium used for glial cells and plated onto polyornithine-coated coverslips at a density of 160,000 cells per coverslip. The day after plating, coverslips were transferred to dishes containing a glial monolayer in neuron maintenance medium (DULBECCO'S modified Eagle's medium and Ham's nutrient mix F12 supplemented with 5 µg/ml insulin, 100 µg/ml transferrin, 100 µg/ml putrescin, 30 nM Na selenite, 20 nM progesterone and penicillin 100 U/ml) supplemented with cytosine arabinoside 5 µM. Coverslips were inverted so that the hippocampal neurons faced the glia monolayer. Paraffin dots adhering to the coverslips supported them above the glia, creating a narrow gap that prevented the two cell types from contacting each other but allowed the diffusion of soluble substances. These culture conditions allowed the growth of differentiated neuronal cultures with >98% homogeneity, as assessed by immunochemistry of microtubule-associated protein 2 and GFAP. Cells were then treated for 24 hours with 1 µM Trimethyl tin (TMT), in the presence or absence of rhEPO (10 U (80 ng)/ml), the supernatants used for TNF assay and cellular viability evaluated as described below. When indicated, glial cells were cultured in the presence of LPS for 24 hours, with or without rhEPO, and TNF measured in the cultured supernatants. Cell viability was measured by the 3-(4,5-dimethyl-thiazol-2-yl)-2,5-diphenyltetrazolium bromide (MTT) assay. Denizot, F., and Lang, R. 1986. Rapid colorimetric assay for cell growth and survival. Modifications to the tetrazolium dye procedure giving improved sensitivity and reliability. *J Immunol Methods* 89:271-277. Briefly, MTT tetrazolium salt was dissolved in serum-free medium to a final concentration of 0.75 mg/ml and added to the cells at the end of the treatment for 3 h at 37° C. The medium was then removed and the formazan was extracted with IN HCl:isopropanol (1:24). Absorbance at 560 nm was read on a microplate reader.

Figure 29B:
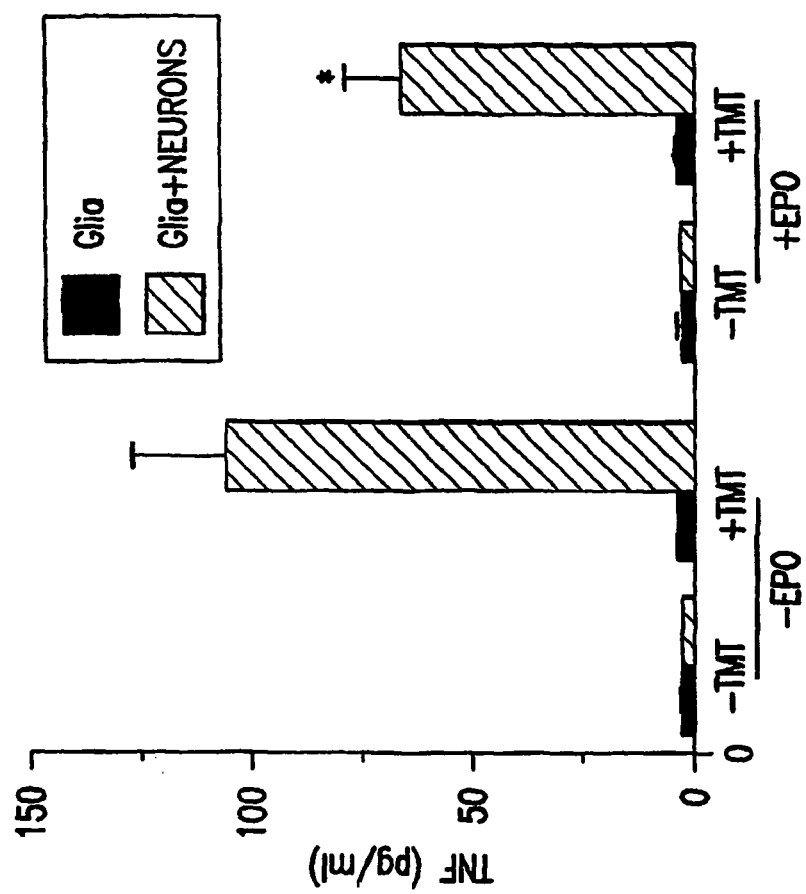
FIGS. 29A and 29B shows that erythropoietin suppresses inflammation associated with neuronal death.
Figure 29A:
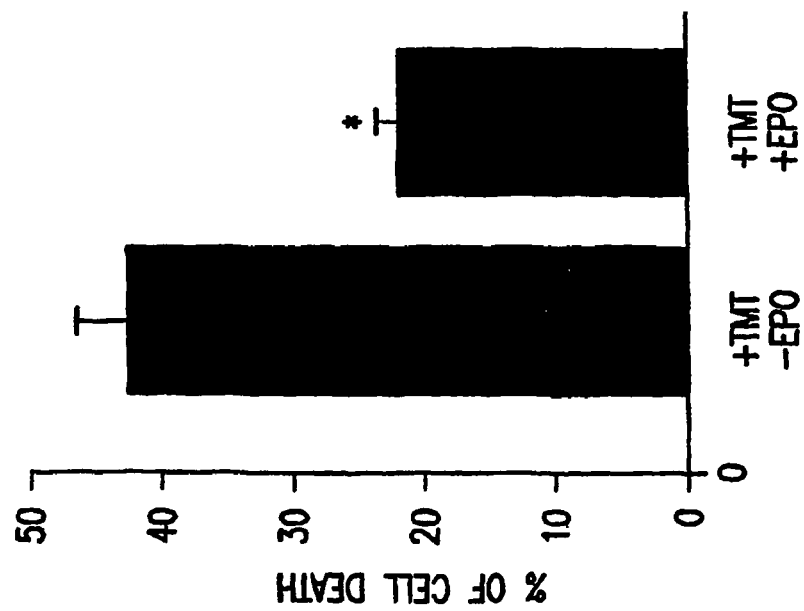

FIG. 29 shows that rhEPO prevents neuronal death-induced TNF production in mixed neuron-glia cultures. Panel A: Percentage of neural cell death induced by TMT 1 µM without or with treatment with rhEPO (10 U/ml). Panel B: Release of TNF from glial cells exposed to TMT 1 µM in the presence (hatched bars) or absence (filled bars) of neurons, with or without rhEPO (10 U/ml). Similar results would be expected from the therapeutic treatment with the tissue protective cytokines of the present invention.

The invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

All references cited herein are incorporated by reference herein in their entireties for all purposes.

What is claimed is:

1. A method for treating an inflammatory disease in a mammal, said method comprising administering to a mammal in need thereof a pharmaceutical composition comprising a prophylactically or therapeutically effective amount of a chemically modified erythropoietin and an anti-inflammatory agent or a prophylactically or therapeutically effective amount of a chemically modified erythropoietin and an immunomodulatory agent, wherein said inflammatory disease is stroke, wherein said chemically modified erythropoietin has a reduced level of in vivo erythropoietic activity compared to native erythropoietin as determined by the exhypoxic polycythemic mouse bioassay, and has tissue protective activity in vivo as determined by the middle cerebral artery occlusion test, and wherein said chemically modified erythropoietin comprises:
 i) a chemically modified arginine residue at position 31, 37, 41, 80, 103, 130, 137, 158, 166, 170, 177, 189, or 193 of SEQ ID NO:5;
 ii) a chemically modified lysine residue at position 47, 72, 79, 124, 143, 167, 179, or 181 of SEQ ID NO:5 or a chemical modified N-terminal amino group;
 iii) a chemically modified tyrosine residue at position 42, 76, 172, or 183 of SEQ ID NO:5;
 iv) a chemically modified aspartic acid or a glutamic acid residue at position 35, 70, 123, 150, 163, 192, 40, 45, 48, 50, 58, 64, 82, 89, 99, 116, 144, or 186 of SEQ ID NO:5; and
 v) a chemically modified tryptophan residue at position 78, 91, or 115 of SEQ ID NO:5, wherein the chemical modification results from one of the following chemical reactions: acetylation; carbamylation; succinylation; carboxymethyllysination; alkylation; nitration; iodination; biotinylation; a reaction with n-bromosuccinimide, chlorosuccinimide, vicinal diketone, or glyoxal; a reaction with R-glyoxal, wherein R is selected from the group consisting of aryl, heteroaryl, lower alkyl, lower alkoxy, cycloalkyl group, and alpha-deoxyglycitolyl; or a reaction with carbodiimide followed by reaction with an amine.

2. The method of claim 1, wherein the anti-inflammatory agent is selected from the group consisting of a steroid, a non-steroidal anti-inflammatory drug, a beta-agonist, an anti-cholinergic agent, a methyl xanthine, gold injection, a sulphasalazine, penicillamine, an anti-angiogenic agent, dapsone, psoralen, an anti-malarial agent, an anti-viral agent, and an antibiotic.

3. The method of claim 1, wherein the immunomodulatory agent is selected from the group consisting of a proteinaceous agent, a peptide mimetic, an antibody, a nucleic acid molecule, a small molecule, an organic compound, an inorganic compound, methothrexate, leflunomide, cyclophosphamide, cytoxan, Immuran, cyclosporine A, minocycline, azathioprine, an antibiotic, methylprednisolone (MP), a corticosteroid, a steroid, mycophenolate mofetil, rapamycin, mizoribine, deoxyspergualin, brequinar, a malononitriloaminde, a T cell receptor modulator, and a cytokine receptor modulator.

4. The method of claim 1, wherein said chemically modified erythropoietin is asialoerythropoietin or phenylglyoxal-erythropoietin.

5. The method of claim 1, wherein said chemically modified erythropoietin is an erythropoietin comprising a R-glyoxal moiety on the one or more arginine residues, wherein R is aryl or alkyl moiety.

6. The method of claim 5, wherein said chemically modified erythropoietin is phenylglyoxal-erythropoietin.

7. The method of claim 1, wherein said chemically modified erythropoietin is an erythropoietin in which at least one arginine residue is modified by reaction with a vicinal diketone selected from the group consisting of 2,3-butanedione and cyclohexanedione.

8. The method of claim 1, wherein said chemically modified erythropoietin is an erythropoietin in which at least one arginine residue is reacted with 3-deoxyglucosone.

9. The method of claim 1, wherein said chemically modified erythropoietin is an erythropoietin molecule comprising at least one biotinylated lysine or biotinylated N-terminal amino group.

10. The method of claim 1, wherein said chemically modified erythropoietin molecule is biotinylated.

11. The method of claim 1, wherein said chemically modified erythropoietin is a glucitolyl lysine erythropoietin or a fructosyl lysine erythropoietin.

12. The method of claim 1, wherein said chemically modified erythropoietin is an erythropoietin having at least one carbamylated lysine residue.

13. The method of claim 12, wherein said carbamylated erythropoietin is selected from the group consisting of alpha-N-carbamoylerythropoietin; N-epsilon-carbamoylerythropoietin; alpha-N-carbamoyl, N-epsilon-carbamoylerythropoietin; alpha-N-carbamoylasialoerythropoietin; N-epsilon-carbamoylasialoerythropoietin; alpha-N-carbamoyl, N-epsilon-carbamoylasialoerythropoietin; alpha-N-carbamoylhyposialoerythropoietin; N-epsilon-carbamoylhyposialoerythropoietin; and alpha-N-carbamoyl, N-epsilon-carbamoylhyposialoerythropoietin.

14. The method of claim 1, wherein said chemically modified erythropoietin is an erythropoietin in which at least one lysine residue is acylated.

15. The method of claim 14, wherein a lysine residue of said chemically modified erythropoietin is acetylated.

16. The method of claim 15, wherein said acetylated erythropoietin is selected from the group consisting of alpha-N-acetylerythropoietin; N-epsilon-acetylerythropoietin; alpha-N-acetyl, N-epsilon-acetylerythropoietin; alpha-N-acetylasialoerythropoietin; N-epsilon-acetylasialoerythropoietin; alpha-N-acetyl, N-epsilon-acetylasialoerythropoietin; alpha-N-acetylhyposialoerythropoietin; N-epsilon-acetylhyposialoerythropoietin; and alpha-N-acetyl, N-epsilon-acetylhyposialoerythropoietin.

17. The method of claim 1, wherein said chemically modified erythropoietin is an erythropoietin comprising a succinylated lysine residue.

18. The method of claim 17, where said succinylated erythropoietin is selected from the group consisting of alpha-N-succinylerythropoietin; N-epsilon-succinylerythropoietin; alpha-N-succinyl, N-epsilon-succinylerythropoietin: alpha-N-succinylasialoerythropoietin; N-epsilon-succinylasialoerythropoietin; alpha-N-succinyl. N-epsilon-succinylasialoerythropoietin; alpha-N-succinylhyposialoerythropoietin; N-epsilon-succinylhyposialoerythropoietin; and alpha-N-succinyl, N-epsilon-succinylhyposialoerythropoietin.

19. The method of claim 1, wherein said chemically modified erythropoietin is an erythropoietin with at least one lysine residue modified by a 2, 4, 6-trinitrobenzenesulfonic acid salt.

20. The method of claim 19, wherein the salt is 2, 4, 6-trinitrobenzenesulfonate sodium.

21. The method of claim 1, wherein said chemically modified erythropoietin is an erythropoietin in which at least one tyrosine residue is nitrated and/or iodinated.

22. The method of claim 1, wherein said chemically modified erythropoietin is an erythropoietin in which an aspartic acid and/or glutamic acid residue is reacted with a carbodiimide followed by reaction with an amine.

23. The method of claim 22, wherein said amine is glycinamide.

24. The method of claim 1, wherein said chemically modified erythropoietin is an alpha-N-carbamoyl, N-epsilon-carbamoylerythropoietin.

25. The method of claim 1, wherein said chemically modified erythropoietin is non-erythropoietic.

26. The method of claim 1, wherein said chemically modified erythropoietin and the anti-inflammatory agent or immunomodulatory agent are administered to the mammal concurrently.

27. A method for treating an inflammatory disease in a mammal comprising administering to a mammal in need thereof a prophylactically or therapeutically effective amount of a chemically modified erythropoietin,
wherein said inflammatory disease is stroke,
wherein said chemically modified erythropoietin has a reduced level of in vivo erythropoietic activity compared to native erythropoietin as determined by the exhypoxic polycythemic mouse bioassay, and has tissue protective activity in vivo as determined by the middle cerebral artery occlusion test,
and wherein said chemically modified erythropoietin comprises:
  i) a chemically modified arginine residue at position 31, 37, 41, 80, 103, 130, 137, 158, 166, 170, 177, 189, or 193 of SEQ ID NO:5;
  ii) a chemically modified lysine residue at position 47, 72, 79, 124, 143, 167, 179, or 181 of SEQ ID NO:5 or a chemically modified N-terminal amino group;
  iii) a chemically modified tyrosine residue at position 42, 76, 172, or 183 of SEQ ID NO:5;
  iv) a chemically modified aspartic acid residue at position 35, 70, 123, 150, 163, or 192 of SEQ ID NO:5;
  v) a chemically modified glutamic acid residue at position 40, 45, 48, 50, 58, 64, 82, 89, 99, 116, 144, or 186 of SEQ ID NO:5; or
  vi) a chemically modified tryptophan residue at position 78, 91, or 115 of SEQ ID NO:5,
wherein the chemical modification results from one of the following chemical reactions: acetylation; carbamylation; succinylation; carboxymethyllysination; alkylation; nitration; iodination; biotinylation; a reaction with n-bromosuccinimide, chlorosuccinimide, vicinal diketone, or glyoxal; a reaction with R-glyoxal wherein R is selected from the group consisting of aryl, heteroaryl, lower alkyl, lower alkoxy, cycloalkyl group, and alpha-deoxyglycitolyl; or a reaction with carbodiimide followed by reaction with an amine.

28. The method of claim 27, wherein said chemically modified erythropoietin is an erythropoietin having at least one carbamylated lysine residue.

29. The method of claim 28, wherein said carbamylated erythropoietin is selected from the group consisting of alpha-N-carbamoylerythropoietin; N-epsilon-carbamoylerythropoietin; alpha-N-carbamoyl, N-epsilon-carbamoylerythropoietin; alpha-N-carbamoylasialoerythropoietin; N-epsilon-carbamoylasialoerythropoietin; alpha-N-carbamoyl, N-epsilon-carbamoylasialoerythropoietin; alpha-N-carbamoylhyposialoerythropoietin; N-epsilon-carbamoylhyposialoerythropoietin; and alpha-N-carbamoyl, N-epsilon-carbamoylhyposialoerythropoietin.

30. The method of claim 27, wherein said chemically modified erythropoietin is non-erythropoietic.

31. The method of claim 29, wherein said chemically modified erythropoietin is an alpha-N-carbamoyl, N-epsilon-carbamoylerythropoietin.

* * * * *